US008686221B2

(12) United States Patent
Sanz Molinero

(10) Patent No.: US 8,686,221 B2
(45) Date of Patent: *Apr. 1, 2014

(54) PLANTS HAVING IMPROVED GROWTH CHARACTERISTICS UNDER REDUCED NUTRIENT AVAILABILITY AND A METHOD FOR MAKING THE SAME

(75) Inventor: Ana Isabel Sanz Molinero, Gentbrugge (BE)

(73) Assignee: CropDesign N.V., Zwijnaarde (BE)

( * ) Notice: Subject to any disclaimer, the term of this patent is extended or adjusted under 35 U.S.C. 154(b) by 754 days.

This patent is subject to a terminal disclaimer.

(21) Appl. No.: 12/598,071

(22) PCT Filed: Apr. 30, 2008

(86) PCT No.: PCT/EP2008/055359
§ 371 (c)(1),
(2), (4) Date: May 28, 2010

(87) PCT Pub. No.: WO2008/132231
PCT Pub. Date: Nov. 6, 2008

(65) Prior Publication Data
US 2010/0251423 A1    Sep. 30, 2010

Related U.S. Application Data

(63) Continuation-in-part of application No. 11/799,083, filed on Apr. 30, 2007.

(51) Int. Cl.
C12N 15/82    (2006.01)
C12N 15/10    (2006.01)
C12N 15/00    (2006.01)

(52) U.S. Cl.
USPC .......... 800/278; 800/290; 435/468; 435/419; 536/23.1; 536/24.1

(58) Field of Classification Search
None
See application file for complete search history.

(56) References Cited

U.S. PATENT DOCUMENTS

| | | | |
|---|---|---|---|
| 5,981,729 | A | 11/1999 | Chun et al. |
| 6,696,623 | B1 | 2/2004 | Doerner et al. |
| 7,235,710 | B2 | 6/2007 | Hatzfield et al. |
| 2005/0044585 | A1 | 2/2005 | Good et al. |
| 2007/0022495 | A1 | 1/2007 | Reuber et al. |
| 2007/0186308 | A1 | 8/2007 | Reuber et al. |
| 2007/0192889 | A1* | 8/2007 | La Rosa et al. ............... 800/278 |
| 2007/0234439 | A1 | 10/2007 | Chan et al. |
| 2008/0127365 | A1 | 5/2008 | Sanz Molinero et al. |
| 2010/0251423 | A1 | 9/2010 | Sanz Molinero |

FOREIGN PATENT DOCUMENTS

| | | | |
|---|---|---|---|
| EP | 1586652 A1 | 10/2005 | |
| WO | WO-03/007699 A2 | 1/2003 | |
| WO | WO-03/014327 A2 | 2/2003 | |
| WO | WO-03/100054 A1 | 12/2003 | |
| WO | WO-2004/065596 A2 | 8/2004 | |
| WO | WO-2004/099365 A2 | 11/2004 | |
| WO | WO-2007/051866 A2 | 5/2007 | |
| WO | WO 2007051866 A2 * | 5/2007 | |

OTHER PUBLICATIONS

Henriksson et al. Plant Phys 139:509-18 (2005).*
de Pater et al., Plant J 2:837 (1992).*
Tittonell et al., Ag Ecosys Environ 105:213-220 (2005).*
(Chan et al., BBA 1442:1-19 (1998).*
Palena et al., J Mol Biol 308:39-47 (2001).*
Lazar et al., Mol Cell Biol 8(3):1247-52 (1988).*
Accession No. AED92122.*
Blast SEQ ID No. 33 pp. 1-4.*
Blast SEQ ID No. 33 pp. 1-4, 2012.*
Accession No. AED092122, 2000.*
Sreenivasulu, N., et al., "Deciphering the Regulatory Mechanisms of Abiotic Stress Tolerance in Plants by Genomic Approaches", Gene, vol. 388, (2007), pp. 1-13.
"*Arabidopsis thaliana* cDNA clone:RAFL06-11-C05, 3'-end", EMBL Database, Accession No. AV785059, Mar. 19, 2002.
"*Arabidopsis thaliana* clone 11036 mRNA, complete sequence", EMBL Database, Accession No. AY084518, Jun. 14, 2002.
"Hypothetical protein", UniProt Database, Accession No. Q8W481, Mar. 1, 2002.
"*Oryza sativa* Nrt2 mRNA for high affinity nitrate transporter, complete cds", EMBL Database, Accession No. AB008519, Sep. 23, 1998.
Mori, M. et al., "Analysis of Nitrate Uptake Ability in Transgenic Rice Plants Over-Expressing High Affinity Nitrate Transporter", Plant Cell Physiol., vol. 46, Suppl., (2005), pp. S150.
Fraisier, V., et al., "Constitutive Expression of a Putative High-Affinity Nitrate Transporter in *Nicotiana plumbaginifolia*: Evidence for Post-Transcriptional Regulation by a Reduced Nitrogen Source", The Plant Journal, vol. 23, No. 4, (2000), pp. 489-496.
Forde, B.G., "Nitrate Transporters in Plants: Structure, Function and Regulation", Biochimica et Biophysica Acta, vol. 1465, No. 1-2, (2000), pp. 219-235.
Orsel, M., et al., "Disruption of the Nitrate Transporter Genes *AtNRT2.1* and *AtNRT2.2* Restricts Growth at Low External Nitrate Concentration", Planta, vol. 219, No. 4, (2004), pp. 714-721.
Tong, Y, et al., "A Two-Component High-Affinity Nitrate Uptake System in Barley", The Plant Journal, vol. 41, No. 3, (2005), pp. 442-450.
Crawford, N.M., et al., "Molecular and Physiological Aspects of Nitrate Uptake in Plants", Trends in Plant Science, vol. 3, No. 10, (1998), pp. 389-395.
Deng, X., et al., "Characterization of Five Novel Dehydration-responsive Homeodomain Leucine Zipper Genes from the Resurrection Plant *Craterostigma plantagineum* , Plant Molecular Biology", vol. 49, No. 6, (2002), pp. 601-610.

(Continued)

*Primary Examiner* — Brent T Page
*Assistant Examiner* — Russell Boggs
(74) *Attorney, Agent, or Firm* — Novak Druce Connolly Bove + Quigg LLP

(57) ABSTRACT

The present invention relates generally to the field of molecular biology and concerns a method for improving plant growth characteristics relative to wild type plants. More specifically, the present invention concerns a method for increasing yield in plants grown under reduced nutrient availability, relative to corresponding wild type plants, comprising modulating expression in a plant of a nucleic acid sequence encoding a class I homeodomain leucine zipper (HDZip) hox5 polypeptide or a homologue thereof.

19 Claims, 23 Drawing Sheets

(56) References Cited

OTHER PUBLICATIONS

Meijer, A.H., et al., "HD-Zip Proteins of Families I and II From Rice: Interactions and Functional Properties", Mol. Gen. Genet., vol. 263, No. 1, (2000), pp. 12-21.

"Homeodomain leucine zipper protein (Os08g0416000 protein)", UniProt Database, Accession No. Q6ZA74, Jul. 5, 2004.

Henriksson, E., et al., "Homeodomain Leucine Zipper Class I Genes in Arabidopsis. Expression Patterns and Phylogenetic Relationships", Plant Physiology, vol. 139, (2005), pp. 509-518.

Hanson, J. et al., "Sugar-dependent Alterations in Cotyledon and Leaf Development in Transgenic Plants Expressing the HDZhdip Gene *ATHB13*", Plant Molecular Biology, vol. 45, (2001), pp. 247-262.

"*Oryza sativa* homeodomain leucine zipper protein (Oshox5) mRNA, complete cds", EMBL Database, Accession No. AF145729, Jun. 9, 1999.

Aoyama, et al., "Ectopic Expression of the *Arabidopsis* Transcriptional Activator Athb-1 Alters Leaf Cell Fate in Tobacco," The Plant Cell (Nov. 1995), vol. 7, pp. 1773-1785.

Li, J., et al., "Variation for Thermal Properties of Starch in Tropical Maize Germ Plasm," Cereal Chem., vol. 71, No. 1, (1994), pp. 87-90.

\* cited by examiner

Class I homeodomain of HDZip

|  | Helix 1 | Helix 2 | Helix 3 |
| --- | --- | --- | --- |
| | 1 | | 60 |

| | | |
| --- | --- | --- |
| Zeama_hox5 | (SEQ ID NO 06) | APEKKRRLTAEQVQILERSFEEENKLEPERKTELARRLGMAPRQVAVWFQNRRARWKTKQ |
| Glyma_HD157 | (SEQ ID NO 20) | QPGKKRRLTSEQVQFLERNFEVENKLEPERKVQLAKELGLQPRQVAIWFQNRRARFKTKQ |
| Lyces_VaHOX1 | (SEQ ID NO 28) | QAEKKRRLTDNQVQFLEKSFGEENKLEPERKVQLAKELGLQPRQIAIWFQNRRARWKTKQ |
| Dauca_CHB3 | (SEQ ID NO 18) | QPEKKRRLKADIQFLEKSFETDNKLEPERKVQLAKELGLQPRQVAIWFQNRRARWKTKT |
| Medtr_hox16 | (SEQ ID NO 30) | QSEKKRRLSVDQVQFLEKSFEEDNKLEPERKTKLAKDLGLQPRQVAIWFQNRRARWKTKQ |
| Triae_hox16 | (SEQ ID NO 14) | LPEKKRRLITPEQVHILERSFEEENKLEPERKTELARKLGLQPRQVAVWFQNRRARWKTKT |
| Goshi_hox5 | (SEQ ID NO 24) | LPEKKRRLTSEQVYILEKSFEAENKLEPERKSQLAKKLGLQPRQVAVWFQNRRARWKTKT |
| Sorbi_hox5 | (SEQ ID NO 12) | APEKKRRLTAEQVQILERSFEEENKLEPERKTELARRLGMAPRQVAVWFQNRRARWKTKQ |
| Sacof_hox5 | (SEQ ID NO 10) | APEKKRRLTAEQVQILERSFEEENKLEPERKTELARRLGMAPRQVAVWFQNRRARWKTKQ |
| Aqufo_hox5 | (SEQ ID NO 32) | LPEKKRRLTSEQVHILEKSFETENKLEPDRKTQLAKKLGLQPRQVAVWFQNRRARWKTKQ |
| Orysa_hox5 | (SEQ ID NO 02) | APEKKRRLTAEQVQMLERSFEEENKLEPERKTELARRLGMAPRQVAVWFQNRRARWKTKQ |
| Zeama_hox16 | (SEQ ID NO 08) | LPEKKRRLITPEQVLILERSFEEENKLEPERKTELARKLGLQPRQVAVWFQNRRARWKTKQ |
| Orysa_hox16 | (SEQ ID NO 04) | LPEKKRRLITPEQVHILEKSFEEENKLEPERKTELARKLGLQPRQVAVWFQNRRARWKTKQ |
| Lyces_hox5 | (SEQ ID NO 26) | SPEKKRRLITPEQVHILEKSFETENKLEPERKTQLAXKLGLQPRQVAVWFQNRRARWKTKQ |
| Arath_ATHB1 | (SEQ ID NO 16) | LPEKKRRLITTEQVHILEKSFEEENKLEPERKTQLAKKLGLQPRQVAVWFQNRRARWKTKQ |
| Crapl_CPHB-5 | (SEQ ID NO 22) | LPEKKRRLTAEQVHILEKSFEAENKLEPERKAELAKKLGLQPRQVAIWFQNRRARWKTKQ |
| Orysa_hox6 | (SEQ ID NO 39) | AADRKKRFSEEQIKSLESMFATQTKLEPRQKLQLARELGLQPRQVAIWFQNRRARWKSKQ |
| Orysa_hox4 | (SEQ ID NO 37) | GGEKKRRLSVEQVRALERSFEVENKLEPERKARLARDLGLQPRQVAVWFQNRRARWKTKQ |

| Consensus | PEKKRRLTAEQV I LERSFEEENKLEPERKT LARKLGLQPRQVAVWFQNRRARWKTKQ |
| --- | --- |
| Homeodomain invariant amino acids | $L_{16}$ ; $W_{48}F_{49}N_{51}R_{53}$ ; $W_{56}$ |
| HDZip Class I preferred amino acids | $A_{46}$ |

FIGURE 1

Class I leucine zipper of HDZip

| | | | | | | |
|---|---|---|---|---|---|---|
| Zeama_hox5 (SEQ ID NO 06) | TKQLETDYDRL | KAAYDALAADHQGL | LADNDL | RAQVISL | TEK | |
| Glyma_HD157 (SEQ ID NO 20) | TKQLEKDYGVL | KASYDRLKSDYESL | VQENDKL | KAEVNSL | ESK | |
| Lyces_VaHOX1 (SEQ ID NO 28) | TKQLEKDYDEL | RNRYDTLKSNYNNL | KEKEDL | RTEVFRL | TGK | |
| Dauca_CHB3 (SEQ ID NO 18) | TKTLEKDYDVL | QNSYNSLKADYDNL | LAEKEKL | KAEVLDL | TDK | |
| Medtr_hox16 (SEQ ID NO 30) | TKQLEKDYDSL | NDGYESLKTEYDNL | LKEKDRL | QSEVASL | TEK | |
| Triae_hox16 (SEQ ID NO 14) | TKTLERDFDRL | KASFDALRADHDAL | QDNHRL | RSQVVTL | TEK | |
| Goshi_hox5 (SEQ ID NO 24) | TKTLERDYDLL | KSSFDSLQSNYDTI | LKENEKL | KSEVASL | TEK | |
| Sorbi_hox5 (SEQ ID NO 12) | TKQLERDYDRL | KAAYDALAADHQGL | LADNDSL | RAQVISL | TDK | |
| Sacof_hox5 (SEQ ID NO 10) | TKQLETDYDHL | KAAYDALAADHQGL | LADNDSL | RAQVVSL | TEK | |
| Aqufo_hox5 (SEQ ID NO 32) | TKQLETDYDIL | KASYDSLRSDYDDI | VKENEKL | KSEVVSL | TGK | |
| Orysa_hox5 (SEQ ID NO 02) | TKQLEHDFDRL | KAAYDALAADHHAL | LSDNDRL | RAQVISL | TEK | |
| Zeama_hox16 (SEQ ID NO 08) | TKQLERDFDRL | KASFDALRADHDAL | QDNNRL | RSQVVSL | TEK | |
| Orysa_hox16 (SEQ ID NO 04) | TKQLERDYDQL | KSSYDSLLSDFDSV | RKDNDKL | KSEVVSL | MEK* | |
| Lyces_hox5 (SEQ ID NO 26) | TKQLERDYDLL | KSTYDQLSNYDSI | VMDNDKL | RSEVTSL | TEK | |
| Arath_ATHB1 (SEQ ID NO 16) | TKQLERDYDKL | KSSYDSLLSTYDSI | RQENDKL | KAELLSL | NEK | |
| Crap1_CPHB-5 (SEQ ID NO 22) | SKQLEREYSAL | RDDYDALLCSYESL | KKEKLAL | IKQLEKL | AEM | |
| Orysa_hox6 (SEQ ID NO 39) | TKQLERDYAAL | RHSYDSLRLDHDAL | RRDKDAL | LAEIKEL | KAK | |
| Orysa_hox4 (SEQ ID NO 37) | | | | | | |
| Consensus | TKQLERDYD L | KASYDALRADYDAL | DNDKLRAE | VVSL | TEK | |
| | abcdefg | abcdefgabcdefg | abcdefg | abcdefg | abcdefg | |
| | heptad1 | heptad2heptad3 | heptad4 | heptad5 | heptad6 | |

FIGURE 1 (continued)

```
                         1                                                50
       Zeama_hox5    (1) ---MDPSAVSFDSGGARRGGG----------------AQMLLFGGGGSAN
       Aqufo_hox5    (1) --MDSTTSRLFFDGSCHGN------------------MLLLGSGDPV
      Arath_ATHB1    (1) ---MESNSFFFDPSASHGNS-----------------MFFLGNLNPV
       Orysa_hox5    (1) ---MDPGRVVFDSGVARRACPGG--------------AQMLLFGGGGSAN
      Crapl_CPHB-5   (1) ---MNSARIFFDPSSHGNMLQ----------------FLGNAGGDSSV
       Dauca_CHB3    (1) ---MAGRRVFYG---EGANTTSAS-------LLFHSQRPEPFFLSAPSPS
       Glyma_HD157   (1) ---MASGKLYAGSNMSLLLQNER-------LPCSSEVLESLWAQTSNPAS
       Goshi_Hox5    (1) ---MESGRLFFNPSTTHRN------------------MLLLGNTEPI
       Lyces_hox5    (1) ---MGSGHIFFDPSSCHGN------------------MLFLGSGDPV
       Lyces_VaHOX1  (1) ---MAPGILYGGSSNFDGVFTQKQRDVFSSSTAPKGHLGSLFAPASSSSN
       Medtr_HOX16_1 (1) ---MAGGKLFGGSNMSLLLQNER-------LPCTSEVLESLWVHT--PAS
       Orysa_hox16   (1) ---MESGRLIFSTAGS---GAGQ-------------MLFLDCGAGGGGVG
       Sacof_hox5    (1) ---MDPSAVSFNSGGARRGGGG--------------TQMLLFGGGGSAN
       Sorbi_hox5    (1) ---MDPSAVSFDSGGARRGGGGG-------------GAQMLLFGGGGSAN
       Triae_hox16   (1) ---MEPGRLIFNTSGS---GNGQ-------------MLFMDCGAGGIA-G
       Zeama_hox16   (1) ---MESGRLIFNAPGS---GAGQ-------------MLFLDCGAGGG--P
       Poptr_HOX16_1 (1) ---MAGGTGGSNSNLSVLLQSQRG------PCAASQPLESFFLSGS-SPS
       Poptr_HOX16_2 (1) MAACGGGGGGSNPNLSVLVQSQRG------PCAASQPLEAFFLSGS-SPS
       Poptr_HOX16_3 (1) ---MAGDKDCGSSKMTIFLRNGR----------LPPCESLCILTS-FST
       Phavu_hox16   (1) ---MAGGKLHPGSNMSLLLQNDR-------LPCSSEVLESLWAHTSNAAS
       Lotco_HOX16   (1) ---MAGGRVFSGGSAAPANVSDTS-------LLLQNQPPDSSLFLSTSAS
      Medtr_HOX unknown (1) MHEMAFFQANFMLQTPHHHDDHHQ--------------PSSLNSILPQD
      Piclg_hox unknown (1) ---MACDRSALYTSSVIMNTEDN-------SSAHAIAAMIASSCTPPAT
       Orysa_hox4    (1) ------------------------------------MKRPGGAGG
      Medtr_HOX unknown2 (1) -----------------------------------MKRLNNTSDS
       Orysa_hox6    (1) ---------------------------------
       Consensus     (1)     M   G   F                                    G RPFF  acidic
                                                                  box    box
                         51                                               100
       Zeama_hox5   (32) SNGFFRGVPMAVLGMDDATRVG-------KRPFFTTHE--ELLEEEYYDE
       Aqufo_hox5   (28) LRGSR-----SFINMEDSL---------KRRPFYSST--DELIEEEFYDE
      Arath_ATHB1   (28) VQGGGAR---SMMNMEETS---------KRRPFFSSH--EDLYDDDFYDD
       Orysa_hox5   (34) SGGFFRGVPAAVLGMDESRSSSSAAGAGAKRPFFTTHE--ELLEEEYYDE
      Crapl_CPHB-5  (30) FRGTRSS---SVLNMEESS---------LKRQIFSGGGGDEFYDEEYYDE
       Dauca_CHB3   (38) LIGS-----KSMVSFQDAKRKNP------YDGFFMRSYDEEEIGDEEYDE
       Glyma_HD157  (41) FQGS-----KPVVDFENVSGSR-----MTIRPFFQAIEKEENC-DEDYEG
       Goshi_Hox5   (27) FRGAR-----TMVSMEENP---------KKRLFFSSH--EDLYDEEYYDE
       Lyces_hox5   (27) FRGPRS----TMMKMEDSS---------KRRPFFSSH--EDLYDEEYYDE
       Lyces_VaHOX1 (48) FLGS-----SSMVSFRGVNGG--------KRSFFDSHD-QDDNEADELGE
       Medtr_HOX16_1(39) FQGS-----NSVVNFENGGGSNRV---VTIRPFFQQIEKEENCGDEDYEA
       Orysa_hox16  (32) GGAMFHRGARPVLGMEEGG-------RGVKRPFFITHD--ELLEEEYYDE
       Sacof_hox5   (33) SNGFFRGVPMAVLGMDDATRVG-------KRPFFTTHE--ELLEEEYYDE
       Sorbi_hox5   (35) SNGFFRGVPMAVLGMDDATRVG-------KRPFFTTHE--ELLEEEYYDE
       Triae_hox16  (31) AAGMFHRGVRPVLGGMEEG-------RGVKRPFFTSHD--DMLEEEYYDE
       Zeama_hox16  (30) GGGLFHRGGRPMLGLEEG--------RGVKRPFFTSHD--ELLEEEYYDE
       Poptr_HOX16_1(41) FLGS-----RSMMSFEDVHQANG-----STRPFFRSHDHEDNG-DDDLDE
       Poptr_HOX16_2(44) FLGS-----RSMMSFADVHQANG-----STRPFFRPYDHEDNG-DDDLDE
       Poptr_HOX16_3(36) LHGA-----KSMVNFRNDGGDT------VDMSFFQPHVKEESS-DEDYDA
       Phavu_hox16  (41) FQGS-----KSMVDFENVSGGR-----VTIRPFFQAIEKEDNC-DDDYEG
       Lotco_HOX16  (41) FLGS-----RSMVSFADNKLGQ------TRSFFSAHDLDENG-DEVMDE
      Medtr_HOX unknown (36) YHGG-----PSFLGKRCMS---------FSSGIELGEEANIPEEDLSDD
      Piclg_hox unknown (40) FQGTR-----SISVFETGNERKRP----AQNSYSALELSDDIGDEDGSDD
       Orysa_hox4   (10) GGGS-----PSLVTMANSS---------DDGYGGVGMEAEGDVEEEMMA
      Medtr_HOX unknown2 (11) FSTP-------LITISPSTEEHSPRNKHVYGMEFQSMMLDGFEEEGCVEE
       Orysa_hox6    (1) -----------MDGEEDS---------EWMMMDVG--GKGG---KGGG
       Consensus    (51)          G         S      E     RPFF  E  EE YDE
                                                                conserved domain
```

FIGURE 2

Class I homeodomain

```
                          101                                                      150
Zeama_hox5      (73)  QAP--EKKRRLTAEQVQLLERSFEEENKLEPERKTELARRLGMAPRQVAV
Aqufo_hox5      (62)  QLP--EKKRRLTSEQVHLLEKSFETENKLEPDRKTQLAKKLGLQPRQVAV
Arath_ATHB1     (64)  QLP--EKKRRLTTEQVHLLEKSFETENKLEPERKTQLAKKLGLQPRQVAV
Orysa_hox5      (82)  QAP--EKKRRLTAEQVQMLERSFEEENKLEPERKTELARRLGMAPRQVAV
Crapl_CPHB-5    (68)  QLLP-EKKRRLTAEQVHLLEKSFEAENKLEPERKAELAKKLGLQPRQVAI
Dauca_CHB3      (77)  YFQQPEKKRRLKADQIQFLEKSFETDNKLEPERKVQLAKELGLQPRQVAI
Glyma_HD157     (80)  QFHQPGKKRRLTSEQVQFLERNFEVENKLEPERKVQLAKELGLQPRQVAI
Goshi_Hox5      (61)  QLP--EKKRRLTSEQVYLLEKSFEAENKLEPERKSQLAKKLGLQPRQVAV
Lyces_hox5      (62)  QSP--EKKRRLTPEQVHLLEKSFETENKLEPERKTQLAXKLGLQPRQVAV
Lyces_VaHOX1    (84)  YLHQAEKKRRLTDNQVQFLEKSFGEENKLEPERKVQLAKELGLQPRQIAI
Medtr_HOX16_1   (81)  QYHQQGKKRRLSSEQVQFLEKSFEVENKLEPDRKVQLAKELGLQPRQVAI
Orysa_hox16     (73)  QLP--EKKRRLTPEQVHLLERSFEEENKLEPERKTELARKLGLQPRQVAV
Sacof_hox5      (74)  QAP--EKKRRLTAEQVQLLERSFEEENKLEPERKTELARRLGMAPRQVAV
Sorbi_hox5      (76)  QAP--EKKRRLTAEQVQLLERSFEEENKLEPERKTELARRLGMAPRQVAV
Triae_hox16     (72)  QLP--EKKRRLTPEQVHLLERSFEEENKLEPERKTELARKLGLQPRQVAV
Zeama_hox16     (70)  QLP--EKKRRLTPEQVLLLERSFEEENKLEPERKTELARKLGLQPRQVAV
Poptr_HOX16_1   (80)  YFHQPEKKRRLTVDQVQFLEKSFELENKLEPERKIQLAKDLGLQPRQVAI
Poptr_HOX16_2   (83)  YFHQPEKKRRLTVDQVQFLERSFEVENKLEPERKIQLAKDLGLQPRQVAI
Poptr_HOX16_3   (74)  HLKPSEKKRRLTAAQVQFLEKSFEAENKLEPERKMQLAKELGLQPRQVAI
Phavu_hox16     (80)  QFHQPGKKRRLTSEQVQFLERNFEVENKLEPERKVQLAKELGLQPRQVAI
Lotco_HOX16     (78)  YFHQSEKKRRLSVDQVQFLEKSFEVDNKLEPDRKTKIAKDLGLQPRQVAI
Medtr_HOX unknown  (71)  GSQAGEKKRRLNMEQVKTLEKSFELGNKLEPERKMQLARALNLQPRQVAI
Piclg_hox unknown  (81)  QIHLGEKKRRLTLEQVRALEKNFEMANKLEPEKKMQLAKALGLQPRQIAV
Orysa_hox4      (45)  QGGGGEKKRRLSVEQVRALERSFEVENKLEPERKARLARDLGLQPRQVAV
Medtr_HOX unknown2 (54)  TGHHSEKKRRLRVDQVKALEKNFEVENKLEPERKEKLAIELGLQPRQVAV
Orysa_hox6      (24)  GGGAADRKKRFSEEQIKSLESMFATQTKLEPRQKLQLARELGLQPRQVAI
Consensus      (101)         EKKRRLT EQVQ LEKSFE ENKLEPERK QLAK LGLQPRQVAV
```
conserved domain

Class I Homeodomain    Leucine zipper

```
                          151                                                      200
Zeama_hox5     (121)  WFQNRRARWKTKQLETDYDRLKAAYDALAADHQGLLADNDNLRAQVISLT
Aqufo_hox5     (110)  WFQNRRARWKTKQLERDYDLLKASYDSLRSDYDDIVKENEKLKSEVVSLT
Arath_ATHB1    (112)  WFQNRRARWKTKQLERDYDLLKSTYDQLLSNYDSIVMDNDKLRSEVTSLT
Orysa_hox5     (130)  WFQNRRARWKTKQLEHDFDRLKAAYDALAADHHALLSDNDRLRAQVISLT
Crapl_CPHB-5   (117)  WFQNRRARWKTKQLERDYDKLKSSYDSLLSTYDSIRQENDKLKAELLSLN
Dauca_CHB3     (127)  WFQNRRARWKTKTLEKDYDVLQNSYNSLKADYDNLLAEKEKLKAEVLDLT
Glyma_HD157    (130)  WFQNRRAREKTKQLEKDYGVLKASYDRLKSDYESLVQENDKLKAEVNSLE
Goshi_Hox5     (109)  WFQNRRARWKTKQLERDYDLLKSSFDSLQSNYDTILKENEKLKSEVASLT
Lyces_hox5     (110)  WFQNRRARWKTKQLERDYDQLKSSYDSLLSDFDSVRKDNDKLKSEVVSLM
Lyces_VaHOX1   (134)  WFQNRRARWKTKQLEKDYDELRNRYDTLKSNYNNLLKEKEDLRTEVFRLT
Medtr_HOX16_1  (131)  WFQNRRAREKTKQLEKDYGTLKASFDSLKDDYDNLLQENDKLKEEVNSLK
Orysa_hox16    (121)  WFQNRRARWKTKQLERDFDRLKASFDALRADHDALLQDNHRLHSQVMSLT
Sacof_hox5     (122)  WFQNRRARWKTKQLETDYDHLKAAYDALAADHQGLLADNDSLRAQVVSLT
Sorbi_hox5     (124)  WFQNRRARWKTKQLETDYDRLKAAYDALAADHQGLLADNDSLRAQVISLT
Triae_hox16    (120)  WFQNRRARWKTKTLERDFDRLKASFDALRADHDALLQDNHRLRSQVVTLT
Zeama_hox16    (118)  WFQNRRARWKTKQLERDFDRLKASFDALRADHDALLQDNNRLRSQVVSLT
Poptr_HOX16_1  (130)  WFQNRRARWKTKQLEKDYDVLQSSYNSLKADYDNLLKEKEKLKAEVNLLT
Poptr_HOX16_2  (133)  WFQNRRARWKTKQLEKDYEVLQSSYNGLKADYDNLFKEKEKLKAEVNLLT
Poptr_HOX16_3  (124)  WFQNRRAREKNKQLERDYDSLRISFDKLKADYDKLLLEKQNLKNELLSLK
Phavu_hox16    (130)  WFQNRRAREKTKQLEKDYGTLKASYDRLKGDYESLLQENDKLKAEVNSLE
Lotco_HOX16    (128)  WFQNRRARWKTKQLEKDYDSLHSSFESLKSNYDNLLKEKDMLKAEVASLT
Medtr_HOX unknown (121)  WFQNRRARWKTKQLEKDYDVLKRQYDAIKLDNDALQAQNQKLQAEILALK
Piclg_hox unknown (131)  WFQNRRARWKTKQLEKDFNVLKQDYDALKQDYDNLMEENNNLQAMIERMS
Orysa_hox4     (95)   WFQNRRARWKTKQLERDYAALRHSYDSLRLDHDALRRDKDALLAEIKELK
Medtr_HOX unknown2 (104) WFQNRRARWKTKQLERDYGVLKANYDALKLKFDAIAQDNKAFHKEIKELK
Orysa_hox6     (74)   WFQNKRARWKSKQLEREYSALRDDYDALLCSYESLKKEKLALIKQLEKLA
Consensus     (151)   WFQNRRARWKTKQLE DYD LK SYD L  DYD LL EN  L AEV SLT
```
conserved domain

FIGURE 2 (continued)

```
                              201                                              250
Zeama_hox5      (171) EKLQGKETSPS---------------ATTAAQEVDQPDEHTAVSGTEELL
Aqufo_hox5      (160) GKLQVKEGAGM----------------ELNQISDPPLS--TEENVDVTT
Arath_ATHB1     (162) EKLQGKQETAN----------------EPPGQVPEP-----NQLDPVYI
Orysa_hox5      (180) EKLQDKETSPS-----------SATITTAAQEVDQPDEHTEAASTTGFA
Crapl_CPHB-5    (167) EKLQPKDDDDP----------------SAEIGRNLSSSSPPVDAAEPPC
Dauca_CHB3      (177) DKLLLKEDKGS---------------KTVVFDKQKVSAAFQQERVSNDIS
Glyma_HD157     (180) SKLILRDKEKEE---------NSDDKSSPDDAVNSSSPHNNKEPMDLLI
Goshi_Hox5      (159) EKLQAKDVATE----------------AIAGEKDEG-----LAAEMASA
Lyces_hox5      (160) EKLQGKVVGGA----------------GGNEKSD------ILEVDAMTI
Lyces_VaHOX1    (184) GKLFIKEKGNG-------------QLDLRDEHKHSNALAKETVVDPMS
Medtr_HOX16_1   (181) NKLIPRDKEKV----------NSEDKSS-PEAINSP--HNNIDPMDIIS
Orysa_hox16     (171) EKLQEKETTTEGSAGAAVDVPGL-PAAADVKVAVPDAEEPALEEAAAAFE
Sacof_hox5      (172) EKLQGKETSPS--------------ATTAAQEVDQPDEHTAASGTEKLL
Sorbi_hox5      (174) DKLQRKETSPS--------------ATTAAQEVDQPDEHTAASGTEKLL
Triae_hox16     (170) EKMQDKEAPEGSFGAAADASEPE-QAAAEAKASLADAEEQAAAAEAFEVV
Zeama_hox16     (168) EKLQEKEDATEGGATADTAAP-----AVDVEASLADDVEEPAEPAATFEV
Poptr_HOX16_1   (180) DKLLLKEKEKG---------------ISELSDKDALSQEPPKRAIADSAS
Poptr_HOX16_2   (183) NELLLKEKEKG---------------SSELSDKDALSQEPPKKAIADSAS
Poptr_HOX16_3   (174) EKLLSREESME---------------SSEPFDVIHS-PDAELEPIPDTVS
Phavu_hox16     (180) SKLILRDKEKE----------NSDDKSS-PDAVNSP----HKEPMDLIS
Lotco_HOX16     (178) EKVLARENLKQ----------------VESETKGLVEPPQRPLLDSVS
Medtr_HOX unknown  (171) NREPTESINLN---------------KETEGSSSNRSENSSEIKLDMS
Piclg_hox unknown  (181) SKSQSCNDQKFQAN-----------SSKLQKDDQDLQLLMMSATKVDCA
Orysa_hox4      (145) AKLGDEEAAAS---------------FTSVKEEPAASDGPPAAGFGSSDS
Medtr_HOX unknown2 (154) SKLGEEEKSTIN--------------VLVKEELTMLESCDEDKHNPSSE
Orysa_hox6      (124) EMLQEPRGKYG---------------DNAGDDARSGGVAGMKKEEFVG
Consensus       (201) EKLQ KE
                      conserved
                      domain 251                                              300
Zeama_hox5      (206) AQQ---------------------------LKDNLHSSG----------
Aqufo_hox5      (191) MQFN----------------------VKVEDRLSSGSGVSAVVDEEC
Arath_ATHB1     (190) NAAA----------------------IKTEDRLSSGSVGSAVLDDDA
Orysa_hox5      (218) TVDGALA------------APPPGHQQPPHKDDLVSSGGTNDDGDGGAA
Crapl_CPHB-5    (200) LKLT----------------------VKVEDRLSTGSNGSAVMDGDG
Dauca_CHB3      (212) VGE----------------VLSNSVMDCKQEDHNSVK---SDAVDSDS
Glyma_HD157     (220) ISKNATTTTTSENGTKVLSPLPLPIMVTCCKQEDANSAK---SDVLDSDS
Goshi_Hox5      (187) LQFS----------------------MKVEDRLSSGSVGSAVVDEDA
Lyces_hox5      (187) LQVK----------------------VKAGDRLSSGSGGSAVVDEHS
Lyces_VaHOX1    (219) NVP--------------------ALVVKHQQEDLSSAK---SDVFDSES
Medtr_HOX16_1   (217) ITN-------SENGSKMS----LPNMVLKCKQEDANSAK---SDVLDSDS
Orysa_hox16     (220) EQQE----------------------QQVKAEDRLSTGSGGSAVVDTDA
Sacof_hox5      (207) AQQ---------------------------LKDDLHSSG----------
Sorbi_hox5      (209) VQQ---------------------------LKDDLHSSG----------
Triae_hox16     (219) QQQ-----------------------LHVKDEERLSPGSGGSAVLDARD
Zeama_hox16     (213) LQ------------------------EVKSEDRLSTGSGGSAVVDADA
Poptr_HOX16_1   (215) EGE-----------------VSKISTVACKQEDISSAK---SDIFDSDS
Poptr_HOX16_2   (218) EGE-----------------VSKTSTVACQQEDISSAK---SDMFDSDS
Poptr_HOX16_3   (208) EN-------------------VSAIVPMVTPKQEESSAK---NDVFNSDS
Phavu_hox16     (214) N-------STSENGTKVS----LPIMVT-CKQEDANSAK---SDVLDSDS
Lotco_HOX16     (210) EGEE----------------SKVSVGACKHEDISSAR---SESLDSDS
Medtr_HOX unknown  (204) RTP-------------------------ASDSPLSTHQHTTSRTFFPPS
Piclg_hox unknown  (219) DKEN---------------------NNEGPSSIGSEGSSVLDMDS
Orysa_hox4      (180) DSS-----------------------AVLNDVDAAGAAPAATDALAPEA
Medtr_HOX unknown2 (189) TSNP-----------------------SSESKDHLDYDCIINNNDVGIG
Orysa_hox6      (157) AGG-----------------------AATLYSSAEGGGTTTTTTAKL
Consensus       (251)                              K ED   SG    S VDD
```

FIGURE 2 (continued)

```
                        301                                                350
     Zeama_hox5  (218)  ----------------------------------------DCTGHGTLS--SE
     Aqufo_hox5  (216)  RQ----------LVDSVDSYFPGD----DYGQCIG-------PVDGVQS
    Arath_ATHB1  (215)  PQ----------LLDSCDSYFP--------------------SIVPI
     Orysa_hox5  (255)  VVVF-------DVTEGANDRLSCESAYFADAAEAYERDCAGHYALS--SE
    Crapl_CPHB-5 (225)  PQQL---------LDDSGDSYFEND----EEYDCAA--------ASLAAA
     Dauca_CHB3  (241)  PHYSD---EVYSSFMEPVDRSYVFEPAQS----------------DISQD
    Glyma_HD157  (267)  PHCTS--------FVEPADSSHAFEPEDHSE--------------DFSQD
     Goshi_Hox5  (212)  PQ----------LVDSGNSYFPSD----EYSRGIG-------PFDGVQS
     Lyces_hox5  (212)  SQ----------LVDSGDSYFHTD----HEEYPGPGGCNVPPPMDGLQS
    Lyces_VaHOX1 (245)  PRYTSR---MHSSVVDQDDSARAFETDQS----------------DSSQD
    Medtr_HOX16_1(253)  PHCNDG--NNLSSFIEPTDSDFS----------------------QD
    Orysa_hox16  (247)  QLVVGCGRQHLAAVDSSVESYFPGG----DEYHDC-VMGPMDHAAGGIQS
    Sacof_hox5   (219)  ----------------------------------------DCTGHGALS--SE
    Sorbi_hox5   (221)  ----------------------------------DFTGHGALS--SE
    Triae_hox16  (245)  ALLG-SGCGLAGVVDSSVDSYCFPGGAGGDEYHEC---VVGPVAGG-IQS
    Zeama_hox16  (237)  LLYG----RFAAAVDSSVESYFPGGE---DHYHDCGTMGPVNHGAGGGIQ
   Poptr_HOX16_1 (244)  PHYAD---GVHSSLLEAGDSSYVFEPDQS----------------DLSQD
   Poptr_HOX16_2 (247)  PHFAD---GVHSSLLEAGDSSHVFEPDQS----------------DLSQD
   Poptr_HOX16_3 (236)  PRSFL---------EPRDCYRVFESDQP----------------DFSQV
    Phavu_hox16  (249)  PHCTDG--NHPSSFVEPADSSHAFEPDHS----------------DFSQD
    Lotco_HOX16  (239)  PRYRDG-YGVNSAVLETCDSSYVVEPDQS----------------DMSQD
  Medtr_HOX unknown (228) ARPS-------SGIAQLFQTSSRPE--------------------IQC
  Piclg_hox unknown (243) PGTIDS--------QQNIDSIGFSN--------------------VKA
    Orysa_hox4   (206)  CTFLGAPPAAGAGAGAAAAASHEEVFFHG---------------NFLKV
  Medtr_HOX unknown2(215) ETSSLFPVDLKDGSSDSDSSAISSSGVLQSQ-------------QHLLL
    Orysa_hox6   (181)  MPHFG--------SDDVDAGLFLRPS-----------------SQHHP
     Consensus   (301)  P             DS                              Q 351                                                400
     Zeama_hox5  (229)  EDDGGVVSDEGCS------FALPDAMFAAGFTHHG----------AEEVQ
     Aqufo_hox5  (244)  EEDDISDDS---R------SYFSDVFPAAPEQNHQ----------ES-E
    Arath_ATHB1  (232)  QDNSNASDHDNDR------SCFADVFVPTTSPSHD----------HHGE
     Orysa_hox5  (296)  EEDGGAVSDEGCS------FDLPDAAAAAAMFGAAGVVHHDAADDEEAQ
    Crapl_CPHB-5 (254)  KEDDGSDEGG---------CYFTEALAAEEEE---------------A
     Dauca_CHB3  (272)  EEDDMGNNLFLPS--YHVFSKTEDGSYSDQPSNSSYF--------GFPVE
    Glyma_HD157  (295)  EEDNLSENLLMTFPSSCCLPKVEEHCYDGPPENSCNF--------GFQVE
     Goshi_Hox5  (240)  EDEDGSDNCG--------SYFSDVFATTEQG-----------------
     Lyces_hox5  (247)  EEDDGSDDGSCH------GYFSNVFVAEEQHHEQ----------GE-E
    Lyces_VaHOX1 (276)  DDENFSKNMLSTAN---LLGKDADDDYPATSSNLSYFG--------FPVE
    Medtr_HOX16_1(276)  EEDNDNLSHNLLTLP---CLPKVEEDVCYDDPHENSCNF--------GFPVE
    Orysa_hox16  (292)  EEDDGAGSDEGCS------YYADDAGVLFADHGHHHHHQHADDDEEDGQQ
    Sacof_hox5   (230)  EEDGGVVSDEG-S------FDLPDAMFAAGVTHHGA--------DAEEAQ
    Sorbi_hox5   (232)  EEDGGVVSDEGCS------FDLPDAMFAAGVTHHG----------AEEAQ
    Triae_hox16  (290)  EEDDGAGSDEGCS------YYPDDAAVFFAAAQGHGHHRTDDDDQQDDGQ
    Zeama_hox16  (280)  SDDDGAGSDEGCS------YYADEAAAAAAAFFAGHATHHHADEDEDAGQ
   Poptr_HOX16_1 (275)  EEDNFSKSLLPP----YVFPKLEDDDYSDPPAS--------------FE
   Poptr_HOX16_2 (278)  EEDNLSKSLLPP----YVFPKLEDGDYSDPPAS--------------FE
   Poptr_HOX16_3 (260)  EEDNLTRSFLPP--------PYFPKLYREPPASSRNF--------EFSAE
    Phavu_hox16  (281)  EEDNLSESLLTLP----CLPKVEEACYDDPPENPCNF--------GFHVE
    Lotco_HOX16  (272)  EEDNLTKTLLPPY----MFSKLGDMDYSDPPESSCNF--------GFPEE
  Medtr_HOX unknown (249) QKIDQMVKEES---------LSNMFCGMDDQAG---------------
  Piclg_hox unknown (263) RDLRLECNFRP--------KVEENVSQADEPCNYLFYN------NLETGP
    Orysa_hox4   (240)  EEDETGFLDDDEP--------CGGFFADDQPPP----------LSSWW
  Medtr_HOX unknown2(251) SPESSSMNCFQYQKSYHVKMEEHNFLSADEACN----------FFSDE
    Orysa_hox6   (204)  PPPHAGAGFTSSE------PAADHQSFNFHSSWPSS--------TEQTCS
     Consensus   (351)  EED             D                              E
```

FIGURE 2 (continued)

```
                              Trp tail
                              ┌─────────────┐
                              │401       414│
      Zeama_hox5    (263)     │LANWTSMFWN----│
      Aqufo_hox5    (273)     │TLGWWDWA------│
      Arath_ATHB1   (265)     │SLAFWGWP------│
      Orysa_hox5    (340)     │LGSWTAWFWS----│
      Crapl_CPHB-5  (278)     │HFAWCIWS------│
      Dauca_CHB3    (312)     │DHTFGFWGTEL---│
      Glyma_HD157   (337)     │DQTFCFWPY-----│
      Goshi_Hox5    (263)     │ALGLWAWX------│
      Lyces_hox5    (279)     │HIGWFWS-------│
      Lyces_VaHOX1  (315)     │DQGFGFWTY-----│
      Medtr_HOX16_1 (316)     │DQTFCFWPY-----│
      Orysa_hox16   (336)     │ISCWWMWN------│
      Sacof_hox5    (265)     │LANWTSWFWN----│
      Sorbi_hox5    (266)     │LANWTSWFWN----│
      Triae_hox16   (334)     │IS-YWMWN------│
      Zeama_hox16   (324)     │IS-WWMWN------│
      Poptr_HOX16_1 (306)     │DHAFWSWSY-----│
      Poptr_HOX16_2 (309)     │DHAFWCWSY-----│
      Poptr_HOX16_3 (294)     │DQPFWSWIY-----│
      Phavu_hox16   (319)     │DQTFCFWPY-----│
      Lotco_HOX16   (310)     │DHALWSWSY-----│
 Medtr_HOX unknown  (273)     │---FWPWLEQQHFN│
 Piclg_hox unknown  (299)     │ILWDYNWSSGL---│
      Orysa_hox4    (270)     │AEPTEHWN------│
 Medtr_HOX unknown2 (289)     │QAPTLQWYCPDQWS│
      Orysa_hox6    (240)     │STPWWEFESE----│
      Consensus     (401)     │      W       │
                              └─────────────┘
```

FIGURE 2 (continued)

SEQ ID NO: 1 Oryza sativa Orysa_hox5 cDNA sequence XM_482406.1
ATGGATCCCGGCCGCGTCGTGTTCGACTCCGGCGTGGCGCGGCGGGCGTGCCCCGGCGGCGCGCAG
ATGCTTCTCTTCGGCGGCGGCGGCAGCGCCAACAGCGGCGGCTTCTTCCGAGGCGTGCCGGCGGCG
GTGCTGGGGATGGATGAATCGCGGTCGTCGTCGTCGGCGGCGGGGGCGGGGGCGAAGCGGCCGTTC
TTCACGACGCACGAGGAGCTCCTGGAGGAGGAGTACTACGACGAGCAGGCGCCGGAGAAGAAGCGG
CGGCTGACGGCGGAGCAGGTGCAGATGCTGGAGCGGAGCTTCGAGGAGGAGAACAAGCTGGAGCCG
GAGCGGAAGACGGAGCTCGCCCGCCGCCTCGGCATGGCCCCCGGCAGGTCGCCGTCTGGTTCCAG
AACCGCCGCGCCCGCTGGAAGACCAAGCAGCTCGAGCACGACTTCGACCGCCTCAAGGCCGCCTAC
GACGCCCTCGCCGCCGACCACCATGCCCTCCTCTCCGACAACGACCGCCTCCGCGCGCAGGTAATC
TCATTAACCGAGAAGCTGCAAGACAAGGAGACGTCGCCGTCGTCGGCGACCATCACCACCGCGGCG
CAGGAGGTCGACCAGCCGGACGAACACACGGAGGCCGCGTCAACCACCGGCTTCGCCACCGTCGAC
GGCGCATTGGCGGCGCCACCGCCCGGCCACCAGCAGCCGCCGCATAAAGATGATCTTGTGAGCAGC
GGCGGCACCAACGACGACGGCGATGGCGGCGCGGCCGTGGTGGTCTTCGACGTCACCGAGGGCGCC
AACGACCGCCTCAGCTGCGAGTCGGCGTACTTCGCCGACGCCGCGGAGGCGTACGAGCGCGACTGC
GCCGGGCACTACGCCCTCTCGTCGGAGGAGGAGGACGGCGGCGCGGTCAGCGACGAGGGCTGCAGC
TTCGACCTCCCCGACGCCGCCGCCGCCGCCGCCGCCATGTTCGGCGCCGCCGGAGTTGTGCACCAC
GACGCCGCGGACGACGAGGAGGCGCAGCTCGGCAGCTGGACCGCCTGGTTCTGGAGCTGA

SEQ ID NO: 2 Oryza sativa Orysa_hox5 translated amino acid sequence
MDPGRVVFDSGVARRACPGGAQMLLFGGGGSANSGGFFRGVPAAVLGMDESRSSSSAAGAGAKRPF
FTTHEELLEEEYYDEQAPEKKRRLTAEQVQMLERSFEEENKLEPERKTELARRLGMAPRQVAVWFQ
NRRARWKTKQLEHDFDRLKAAYDALAADHHALLSDNDRLRAQVISLTEKLQDKETSPSSATITTAA
QEVDQPDEHTEAASTTGFATVDGALAAPPPGHQQPPHKDDLVSSGGTNDDGDGGAAVVVFDVTEGA
NDRLSCESAYFADAAEAYERDCAGHYALSSEEEDGGAVSDEGCSFDLPDAAAAAAAMFGAAGVVHH
DAADDEEAQLGSWTAWFWS SEQ ID NO: 3 Oryza sativa Orysa_hox16 cDNA sequence XM_467603.1
ATGGAGTCCGGCCGGCTCATCTTCAGCACGGCGGGCTCCGGCGCCGGGCAGATGCTCTTCTTGGAC
TGCGGCGCTGGCGGCGGCGGCGTCGGCGGCGGGGCCATGTTCCATCGAGGGGCGAGACCGGTGCTC
GGCATGGAGGAAGGAGGGCGCGGCGTCAAGCGGCCCTTCTTCACCACCCCCGACGAGCTCCTCGAA
GAGGAGTACTACGACGAGCAGCTCCCGGAGAAGAAGCGGCGCCTCACGCCGGAGCAGGTGCATCTG
CTGGAGAGGAGCTTCGAGGAGGAGAACAAGCTGGAGCCGGAGCGGAAGACGGAGCTGGCGCGGAAG
CTAGGGCTGCAGCCGCGGCAGGTCGCCGTGTGGTTCCAGAACCGCCGCGCGCGCTGGAAGACCAAG
CAGCTCGAGCGCGACTTCGACCGCCTCAAGGCGTCGTTCGACGCCCTCCGCGCCGACCACGACGCC
CTCCTCCAGGACAACCACCGCCTCCACTCTCAGGTCATGTCGTTGACCGAGAAGCTGCAAGAGAAG
GAGACGACGACCGAGGGCAGCGCCGGCGCGGCCGTTGACGTCCCGGGCTTGCCTGCGGCGGCCGAC
GTGAAGGTCGCCGTCCCGGACGCCGAGGAACCGGCGCTGGAGGAGGCGGCGGCGGCGTTCGAGGAG
CAGCAGGAGCAGCAGGTGAAGGCCGAGGACAGGCTGAGCACGGGCAGCGGCGGGAGCGCGGTGGTG
GACACGGACGCGCAACTGGTGGTCGGGTGCGGCCGGCAAGCATCTCGCCGCCGTGGACAGCAGCGT
GGAGTCGTACTTCCCGGGCGGCGACGAGTACCACGACTGCGTGATGGGCCCCATGGACCACGCCGC
GGGGGGCATCCAGTCGGAGGAGGACGACGGCGCCGGCAGCGACGAGGGCTGCAGCTACTACGCCGA
CGACGCCGGCGTCCTCTTCGCCGACCACGGCCACCACCACCACCACCAACACGCGGACGACGACGA
GGAGGACGGCCAGCAGATCAGCTGCTGGTGGATGTGGAACTAGATTTCTCGCGCGCGCGTCGTC
GTGCATTCAATTCTCGTGTTAAAAAAATCGTTCTCTTTTTCATTTTTCCGCTTCTTTGTCTGTAAT
GTTGAGTTTCGATCGGCTATGAGAAGGAAGGAGGTGTATGCATGTGCATGGTATGGTAGGGTAACA
CATCGGTGA

FIGURE 4 (continued)

SEQ ID NO: 4 Oryza sativa Orysa_hox16 translated amino acid sequence
MESGRLIFSTAGSGAGQMLFLDCGAGGGVGGGAMFHRGARPVLGMEEGGRGVKRPFFTTPDELLE
EEYYDEQLPEKKRRLTPEQVHLLERSFEEENKLEPERKTELARKLGLQPRQVAVWFQNRRARWKTK
QLERDFDRLKASFDALRADHDALLQDNHRLHSQVMSLTEKLQEKETTEGSAGAAVDVPGLPAAAD
VKVAVPDAEEPALEEAAAAFEEQQEQQVKAEDRLSTGSGGSAVVDTDAQLVVGCGRQHLAAVDSSV
ESYFPGGDEYHDCVMGPMDHAAGGIQSEEDDGAGSDEGCSYYADDAGVLFADHGHHHHHQHADDDE
EDGQQISCWWMWN SEQ ID NO: 5 Zea mays Zeama_hox5 cDNA sequence contig from essentially CO458693 & DV024016
ATGGATCCGAGCGCGGTCAGTTTCGACTCTGGCGGCGCGCGGCGGGGCGGCGGCGCGCAGATGCTG
CTCTTCGGCGGCGGAGGCAGCGCCAACAGCAACGGCTTCTTCCGAGGTGTTCCGATGGCGGTCCTG
GGCATGGACGACGCGACGCGCGTGGGCAAGCGGCCCTTCTTCACGACACACGAGGAGCTCCTAGAG
GAGGAGTACTACGACGAGCAGGCGCCGGAGAAGAAGCGCCGACTGACGGCGGAGCAGGTGCAGCTG
CTGGAGCGGAGCTTCGAAGAAGAGAACAAGCTGGAGCCGGAGCGCAAGACCGAGCTGGCTCGCCGC
CTGGGGATGGCGCCCCGCCAGGTAGCTGTTTGGTTCCAGAACCGCCGCGCGCGCTGGAAGACCAAG
CAACTCGAGACCGACTATGACCGCCTCAAGGCTGCTTACGACGCACTCGCCGCCGACCACCAGGGC
CTCCTGGCCGACAACGATAACCTCCGGGCACAGGTGATCTCCCTGACGGAGAAGCTGCAAGGCAAG
GAGACATCCCCGTCGGCAACCACTGCTGCCCAAGAGGTCGACCAGCCAGACGAACACACCGCTGTG
TCAGGCACGGAAGAACTGCTGGCGCAGCAGCTCAAGGACAACCTCCACAGCAGCGGCGACTGCACT
GGCCATGGCACCCTCTCTTCGGAAGAAGACGACGGTGGCGTGGTCAGTGACGAGGGCTGCAGCTTC
GCTCTCCCGGATGCCATGTTCGCTGCCGGGTTCACCCACCATGGCGCCGAGGAGGTGCAGCTGGCC
AACTGGACATCCATGTTCTGGAACTGA

SEQ ID NO: 6 Zea mays Zeama_hox5 translated amino acid sequence
MDPSAVSFDSGGARRGGGAQMLLFGGGGSANSNGFFRGVPMAVLGMDDATRVGKRPFFTTHEELLE
EEYYDEQAPEKKRRLTAEQVQLLERSFEEENKLEPERKTELARRLGMAPRQVAVWFQNRRARWKTK
QLETDYDRLKAAYDALAADHQGLLADNDNLRAQVISLTEKLQGKETSPSATTAAQEVDQPDEHTAV
SGTEELLAQQLKDNLHSSGDCTGHGTLSSEEDDGGVVSDEGCSFALPDAMFAAGFTHHGAEEVQLA
NWTSMFWN SEQ ID NO: 7 Zea mays Zeama_hox16 cDNA sequence AY105265
ATGGAGTCTGGACGGCTCATCTTCAACGCGCCGGGCTCTGGCGCCGGGCAGATGCTCTTCCTCGAC
TGCGGCGCAGGCGGCGGTCCCGGCGGCGGCTTGTTCCATCGAGGCGGGAGACCGATGCTTGGCCTT
GAAGAAGGGCGCGGCGTAAAACGGCCCTTCTTCACCTCGCCCGACGAGCTCCTCGAGGAAGAGTAC
TACGACGAGCAGCTGCCGGAGAAGAAGCGCCGCCTCACCCCAGAGCAGGTGCTTCTGCTGGAGAGG
AGCTTCGAGGAGGAGAACAAGCTGGAGCCGGAGCGCAAGACGGAGCTGGCGCGCAAGCTGGGCCTG
CAGCCTCGCCAGGTGGCCGTCTGGTTCCAGAACCGCCGCGCCCGGTGGAAGACCAAGCAGCTCGAG
CGCGACTTCGACCGCCTCAAGGCCTCCTTCGACGCTCTCCGAGCGGACCACGACGCCCTCCTCCAG
GACAACAACCGCCTCCGCTCACAGGTTGTGTCGTTGACCGAGAAGCTGCAAGAGAAGGAGGATGCG
ACGGAGGCGGCGCCACCGCTGACACCGCCGCCGGCGGTGGACGTCGAGGCTTCCCTGGCCGAC
GACGTCGAGGAGCCAGCAGAGCCTGCGGCGACGTTCGAGGTGCTGCAGGAGGTGAAGTCCGAGGAC
AGGCTGAGCACCGGCAGCGGCGGGAGCGCGGTGGTGGACGCGGACGCGCTGCTGTACGGCAGGTTC
GCCGCGGCAGTTGATAGCAGCGTGGAGTCGTACTTCCCCGGCGGCGAGGACCACTACCACGACTGC
GGGACGATGGGCCCCGTGAATCATGGCGCCGGAGGAGGCATCCAGTCGGACGACGACGGCGCCGGC
AGCGACGAGGGGTGCAGCTACTACGCCGACGAAGCCGCCGCCGCCGCCGCCGTTCTTCGCCGGA
CACGCCACCCACCACCACGCGGACGAGGACGAGGACGCCGGCCAGATCAGCTGGTGGATGTGGAAC
TAG

FIGURE 4 (continued)

SEQ ID NO: 8 Zea mays Zeama_hox16 translated amino acid sequence
MESGRLIFNAPGSGAGQMLFLDCGAGGGPGGGLFHRGGRPMLGLEEGRGVKRPFFTSPDELLEEEY
YDEQLPEKKRRLTPEQVLLLERSFEEENKLEPERKTELARKLGLQPRQVAVWFQNRRARWKTKQLE
RDFDRLKASFDALRADHDALLQDNNRLRSQVVSLTEKLQEKEDATEGGATADTAAPAVDVEASLAD
DVEEPAEPAATFEVLQEVKSEDRLSTGSGGSAVVDADALLYGRFAAAVDSSVESYFPGGEDHYHDC
GTMGPVNHGAGGGIQSDDDGAGSDEGCSYYADEAAAAAAAFFAGHATHHHADEDEDAGQISWWMWN

SEQ ID NO: 9 Saccharum officinarum Sacof_hox5 cDNA sequence contig from essentially CA088615, CA115362 & CA142506
ATGGATCCGAGCGCGGTCAGTTTCAACTCCGGCGGCGCGCGGCGGGGCGGCGGCGGCACGCAGATG
CTGCTCTTCGGCGGCGGAGGCAGCGCCAACAGCAACGGCTTCTTCCGAGGTGTTCCGATGGCGGTC
CTGGGCATGGACGACGCGACGCGCGTGGGCAAGCGGCCCTTCTTCACCACACACGAGGAGCTCCTG
GAGGAGGAGTACTACGACGAGCAGGCGCCCGAGAAGAAGCGCCGTCTGACGGCGGAGCAGGTGCAG
CTGCTGGAGCGGAGCTTCGAGGAAGAGAACAAGCTGGAGCCCGAGCGCAAGACCGAGCTGGCTCGC
CGCCTCGGGATGGCGCCCGCCAGGTGGCCGTCTGGTTCCAGAACCGCCGCGCGCTGGAAGACC
AAGCAGCTCGAGACCGACTATGACCACCTCAAGGCTGCCTACGACGCGCTCGCCGCCGACCACCAG
GGCCTCCTGGCCGACAACGATAGCCTCCGGGCACAGGTGGTCTCCCTAACAGAGAAGCTGCAAGGC
AAGGAGACATCCCCGTCGGCCACCACTGCTGCCCAAGAGGTCGACCAGCCAGACGAACACACCGCG
GCGTCAGGCACTGAGAAACTGCTGGCGCAGCAGCTCAAGGACGACCTCCACAGCAGCGGCGACTGC
ACTGGCCATGGTGCCCTCCTCAGAGGAAGAAGATGGTGGTGTGGTCAGTGACGAGGGCAGCTTT
GATCTCCCGGATGCCATGTTTGCTGCCGGGGTCACCCACCATGGCGCCGACGCCGAGGAGGCACAG
CTGGCCAACTGGACATCCTGGTTCTGGAACTGA

SEQ ID NO: 10 Saccharum officinarum Sacof_hox5 translated amino acid sequence
MDPSAVSFNSGGARRGGGGTQMLLFGGGGSANSNGFFRGVPMAVLGMDDATRVGKRPFFTTHEELL
EEEYYDEQAPEKKRRLTAEQVQLLERSFEEENKLEPERKTELARRLGMAPRQVAVWFQNRRARWKT
KQLETDYDHLKAAYDALAADHQGLLADNDSLRAQVVSLTEKLQGKETSPSATTAAQEVDQPDEHTA
ASGTEKLLAQQLKDDLHSSGDCTGHGALSSEEEDGGVVSDEGSFDLPDAMFAAGVTHHGADAEEAQ
LANWTSWFWN

SEQ ID NO: 11 Sorghum bicolor Sorbi_hox5 BE363386,CD432381
ATGGATCCGAGCGCGGTCAGTTTCGACTCCGGCGGCGCGCGGCGGGGCGGCGGCGGCGGCGCG
CAGATGCTGCTCTTCGGCGGCGGAGGCAGCGCCAACAGCAACGGCTTCTTCCGAGGTGTTCCGATG
GCGGTCCTGGGCATGGACGACGCGACGCGCGTGGGCAAGCGGCCTTTCTTCACCACGCACGAGGAG
CTCCTGGAGGAGGAGTACTACGACGAGCAGGCGCCCGAGAAGAAGCGCCGTCTGACGGCGGAGCAG
GTGCAGCTGCTGGAGCGGAGCTTCGAGGAAGAGAACAAGCTGGAGCCGGAGCGCAAGACCGAGCTG
GCTCGCCGCCTCGGGATGGCGCCTCGCCAGGTGGCCGTCTGGTTCCAGAACCGCCGCGCGCTGG
AAGACTAAGCAGCTCGAGACCGACTATGACCGCCTCAAGGCTGCCTACGACGCGCTCGCCGCCGAC
CACCAGGGCCTCCTGGCCGACAACGATAGCCTCCGGGCACAGGTGATCTCCCTAACGGATAAGCTG
CAACGCAAGGAGACATCCCCGTCGGCGACCACTGCTGCCCAAGAGGTCGACCAGCCAGACGAACAC
ACCGCTGCGTCAGGCACTGAGAAACTGCTGGTGCAGCAGCTCAAGGACGACCTCCACAGCAGCGGC
GACTTCACTGGCCATGGTGCCCTCTCTTCAGAGGAAGAGGATGGTGGTGTGGTCAGCGACGAGGGC
TGCAGCTTTGATCTCCCGGATGCCATGTTCGCTGCCGGGGTCACCCACCATGGCGCCGAGGAGGCG
CAGCTGGCCAACTGGACATCCTGGTTCTGGAACTGA

FIGURE 4 (continued)

SEQ ID NO: 12 Sorghum bicolor Sorbi_hox5 translated amino acid sequence
MDPSAVSFDSGGARRGGGGGGAQMLLFGGGGSANSNGFFRGVPMAVLGMDDATRVGKRPFFTTHEE
LLEEEYYDEQAPEKKRRLTAEQVQLLERSFEEENKLEPERKTELARRLGMAPRQVAVWFQNRRARW
KTKQLETDYDRLKAAYDALAADHQGLLADNDSLRAQVISLTDKLQRKETSPSATTAAQEVDQPDEH
TAASGTEKLLVQQLKDDLHSSGDFTGHGALSSEEEDGGVVSDEGCSFDLPDAMFAAGVTHHGAEEA
QLANWTSWFWN SEQ ID NO: 13 Triticum aestivum Triae_hox16 DR735359,DR741379, CD916488
ATGGAGCCCGGCCGGCTCATCTTCAACACGTCGGGCTCCGGCAACGGACAGATGCTCTTCATGGAC
TGCGGCGCGGGCGGCATCGCCGGCGCGGCCGGCATGTTCCATCGAGGGGTGAGACCGGTCCTCGGC
GGCATGGAAGAAGGGCGCGGCGTGAAGCGGCCCTTCTTCACCTCGCCGGATGACATGCTCGAGGAG
GAGTACTACGACGAGCAGCTCCCGGAGAAGAAGCGGCGCCTCACCCCGGAGCAGGTCCACCTGCTG
GAGAGGAGCTTCGAGGAGGAGAACAAGCTGGAGCCGGAGAGGAAGACGGAGCTGGCCCGCAAGCTC
GGGCTGCAGCCACGCCAGGTGGCCGTCTGGTTCCAGAACCGCCGCGCCCGGTGGAAGACAAAGACG
CTGGAGCGCGACTTCGACCGCCTCAAGGCGTCCTTCGACGCCCTCCGGGCCGACCACGACGCCCTC
CTCCAGGACAACCACCGGCTCCGGTCACAGGTGGTAACGTTGACCGAGAAGATGCAAGATAAGGAG
GCGCCGGAAGGCAGCTTCGGTGCAGCCGCCGACGCCTCGGAGCCGGAGCAGGCGGCGGCGGAGGCG
AAGGCTTCCTTGGCCGACGCCGAGGAGCAGGCCGCGGCAGCGGAGGCGTTCGAGGTGGTGCAGCAG
CAGCTGCACGTGAAGGACGAGGAGAGGCTGAGCCCGGGGAGCGGCGGGAGCGCGGTGCTGGACGCG
AGGGACGCGCTGCTCGGGAGCGGATGCGGCCTCGCCGGCGTGGTGGACAGCAGCGTGGACTCGTAC
TGCTTCCCGGGGGGCGCCGGCGGCGACGAGTACCACGAGTGCGTGGTGGGCCCCGTGGCGGGCGGC
ATCCAGTCGGAGGAGGACGACGGCGCGGGCAGCGACGAGGGCTGCAGCTACTACCCCGACGACGCC
GCCGTCTTCTTCGCCGCCGCGCAAGGGCACGGCCACCATCGCACGGACGACGACGATCAGCAGGAC
GACGGCCAGATCAGCTACTGGATGTGGAACTAG

SEQ ID NO: 14 Triticum aestivum Triae_hox16 translated amino acid sequence
MEPGRLIFNTSGSGNGQMLFMDCGAGGIAGAAGMFHRGVRPVLGGMEEGRGVKRPFFTSPDDMLEE
EYYDEQLPEKKRRLTPEQVHLLERSFEEENKLEPERKTELARKLGLQPRQVAVWFQNRRARWKTKT
LERDFDRLKASFDALRADHDALLQDNHRLRSQVVTLTEKMQDKEAPEGSFGAAADASEPEQAAAEA
KASLADAEEQAAAAEAFEVVQQQLHVKDEERLSPGSGGSAVLDARDALLGSGCGLAGVVDSSVDSY
CFPGGAGGDEYHECVVGPVAGGIQSEEDDGAGSDEGCSYYPDDAAVFFAAAQGHGHHRTDDDQQD
DGQISYWMWN SEQ ID NO: 15 Arabidopsis thaliana Arath_ATHB1 cDNA sequence X58821
ATGGAATCCAATTCGTTTTTCTTCGATCCATCTGCTTCACACGGCAACAGCATGTTCTTCCTTGGG
AATCTCAATCCCGTCGTCCAAGGAGGAGGAGCAAGATCGATGATGAACATGGAGGAAACTTCGAAG
CGAAGGCCCTTCTTTAGCTCCCCTGAGGATCTCTACGACGATGACTTTTACGACGACCAGTTGCCT
GAAAAGAAGCGTCGCCTCACTACCGAACAAGTGCATCTGCTGGAGAAAAGCTTCGAGACAGAGAAC
AAGCTAGAGCCTGAACGCAAGACTCAGCTTGCCAAGAAGCTTGGTCTACAGCCAAGGCAAGTGGCT
GTCTGGTTTCAGAATCGCCGAGCTCGTTGGAAAACAAAACAGCTTGAGAGAGACTACGATCTTCTC
AAGTCCACTTACGACCAACTTCTTTCTAACTACGACTCCATCGTCATGGACAACGATAAGCTCAGA
TCCGAGGTTACTTCCCTGACCGAAAAGCTTCAGGGCAAACAAGAGACAGCTAATGAACCACCTGGT
CAAGTGCCCGAACCAAACCAACTTGATCCGGTTTACATTAATGCGGCAGCAATCAAAACCGAGGAC
CGGTTAAGTTCAGGGAGCGTTGGGAGCGCGGTACTAGACGACGACGCACCTCAACTACTAGACAGC FIGURE 4 (continued)

```
TGTGACTCTTACTTCCCAAGCATCGTACCCATCCAAGACAACAGCAACGCCAGTGATCATGACAAT
GACCGGAGCTGTTTCGCCGACGTCTTTGTGCCCACCACTTCACCGTCGCACGATCATCACGGTGAA
TCATTGGCTTTCTGGGGATGGCCTTAG
```

SEQ ID NO: 16 Arabidopsis thaliana Arath_ATHB1 translated amino acid sequence
```
MESNSFFFDPSASHGNSMFFLGNLNPVVQGGGARSMMNMEETSKRRPFFSSPEDLYDDDFYDDQLP
EKKRRLTTEQVHLLEKSFETENKLEPERKTQLAKKLGLQPRQVAVWFQNRRARWKTKQLERDYDLL
KSTYDQLLSNYDSIVMDNDKLRSEVTSLTEKLQGKQETANEPPGQVPEPNQLDPVYINAAAIKTED
RLSSGSVGSAVLDDDAPQLLDSCDSYFPSIVPIQDNSNASDHDNDRSCFADVFVPTTSPSHDHHGE
SLAFWGWP
```

SEQ ID NO: 17 Daucus carota Dauca_CHB3 cDNA sequence D26575
```
ATGGCGGGTCGGAGGGTGTTCTATGGGGAGGGAGCCAATACGACGTCGGCTAGCCTGTTGTTTCAT
AGTCAAAGACCTGAGCCTTTCTTTCTTTCTGCACCTTCTCCTTCTCTAATTGGTTCAAAATCCATG
GTTAGCTTTCAAGATGCTAAGCGAAAAAATCCCTACGATGGGTTCTTTATGCGGTCATATGATGAA
GAAGAAATTGGGGATGAAGAATATGATGAATACTTTCAGCAGCCTGAGAAGAAGAGGAGGCTCAAG
GCTGATCAAATCCAGTTTCTTGAGAAAAGTTTTGAGACTGATAACAAGCTTGAGCCTGAAAGAAAA
GTTCAGCTTGCAAAAGAACTCGGCTTGCAGCCAAGACAGGTTGCGATATGGTTTCAGAACCGTCGA
GCACGGTGGAAGACCAAAACACTAGAAAAAGATTATGATGTATTGCAAAATAGCTACAACAGCCTC
AAGGCTGACTATGACAATCTACTTGCCGAGAAGAAAAACTTAAAGCCGAGGTTCTCGACCTGACA
GACAAGCTACTTCTCAAAGAAGATAAGGGGAGCAAGACAGTAGTTTTTGATAAGCAAAAGGTGTCT
GCAGCATTCCAACAAGAACGTGTTAGTAATGACATATCTGTGGGTGAAGTACTCAGTAACTCAGTT
ATGGACTGCAAGCAAGAAGATCATAACTCTGTGAAAAGTGATGCAGTTGATTCTGACAGTCCACAC
TACAGTGATGAAGTCTACTCCAGTTTTATGGAGCCAGTGGATCGCTCTTATGTTTTTGAACCTGCT
CAGTCGGATATATCTCAAGATGAAGAAGATGACATGGGGAACAACTTATTTCTCCCATCATATCAT
GTTTTCTCAAAGACTGAAGACGGTAGTTACTCCGACCAGCCTTCGAACTCTTCGTACTTTGGCTTC
CCAGTTGAAGATCATACGTTTGGCTTTTGGGGTACTGAATTATAA
```

SEQ ID NO: 18 Daucus carota Dauca_CHB3 translated amino acid sequence
```
MAGRRVFYGEGANTTSASLLFHSQRPEPFFLSAPSPSLIGSKSMVSFQDAKRKNPYDGFFMRSYDE
EEIGDEEYDEYFQQPEKKRRLKADQIQFLEKSFETDNKLEPERKVQLAKELGLQPRQV
AIWFQNRRARWKTKTLEKDYDVLQNSYNSLKADYDNLLAEKEKLKAEVLDLTDKLLLKEDKG
SKTVVFDKQKVSAAFQQERVSNDISVGEVLSNSVMDCKQEDHNSVKSDAVDSDSPHYSDEVYSSFM
EPVDRSYVFEPAQSDISQDEEDDMGNNLFLPSYHVFSKTEDGSYSDQPSNSSYFGFPVEDHTFGFW
GTEL
```

SEQ ID NO: 19 Glycine max Glyma_HD157 cDNA sequence AF184278
```
ATGGCGAGTGGCAAGCTTTATGCGGGTTCAAACATGTCACTTCTCCTCCAAAACGAAAGGCTCCCT
TGCTCCTCTGAAGTCCTTGAGTCTCTTTGGGCTCAGACCTCTAACCCTGCTTCCTTCCAAGGTTCA
AAACCCGTGGTTGATTTTGAGAATGTAAGTGGGAGCAGGATGACGGATAGGCCTTTCTTTCAAGCG
TTGGAGAAGGAAGAGAACTGTGATGAGGATTACGAGGGTGTTCCACCAACCGGGGAAGAAAAGG
AGGCTCACAAGCGAACAAGTTCAGTTCCTTGAAAGGAACTTTGAGGTAGAGAACAAGCTTGAACCC
GAAAGGAAAGTCCAACTTGCAAAAGAGCTTGGCTTGCAGCCAAGGCAAGTTGCTATATGGTTCCAA
AACCGAAGGGCAAGGTTCAAGACCAAGCAGCTAGAAAAAGACTATGGCGTGTTGAAAGCTAGTTAT
GACAGACTCAAAAGTGACTATGAAAGTCTTGTTCAAGAGAATGACAAGTTAAAAGCAGAGGTGAAT
```

FIGURE 4 (continued)

```
TCTCTGGAGAGCAAATTGATTCTTAGAGATAAAGAGAAGGAGGAGAATTCGGATGACAAGTCATCT
CCTGATGATGCTGTCAATTCTTCTTCACCCCACAACAACAAGGAGCCTATGGATTTATTAATTATT
TCAAAAAATGCAACAACAACAACAACATCTGAAAATGGGACCAAAGTGTTGTCACCACTCCCACTC
CCTATTATGGTAACATGCTGCAAGCAAGAAGATGCCAACTCAGCCAAAAGTGATGTCCTTGATTCG
GATAGCCCACATTGCACTTCATTCGTGGAGCCTGCTGATTCCTCTCATGCCTTTGAACCAGAAGAC
CACTCAGAAGACTTCTCCCAAGATGAAGAGGATAACCTTAGTGAAAACCTTTTGATGACCTTCCCT
TCTTCTTGTTGCTTACCTAAGGTTGAAGAACACTGCTATGACGGCCCTCCTGAAAACTCTTGTAAT
TTTGGCTTCCAGGTTGAGGATCAAACCTTCTGTTTCTGGCCCTATTGA
```

SEQ ID NO: 20 Glycine max Glyma_HD157 translated amino acid sequence
```
MASGKLYAGSNMSLLLQNERLPCSSEVLESLWAQTSNPASFQGSKPVVDFENVSGSRMTDRPFFQA
LEKEENCDEDYEGCFHQPGKKRRLTSEQVQFLERNFEVENKLEPERKVQLAKELGLQPRQVAIWFQ
NRRARFKTKQLEKDYGVLKASYDRLKSDYESLVQENDKLKAEVNSLESKLILRDKEKEENSDDKSS
PDDAVNSSSPHNNKEPMDLLIISKNATTTTTSENGTKVLSPLPLPIMVTCCKQEDANSAKSDVLDS
DSPHCTSFVEPADSSHAFEPEDHSEDFSQDEEDNLSENLLMTFPSSCCLPKVEEHCYDGPPENSCN
FGFQVEDQTFCFWPY
```

SEQ ID NO: 21 Craterostigma plantagineum CPHB-5 AF443621
```
ATGAACTCTGCTCGGATTTTCTTCGACCCATCTTCCCACGGCAACATGCTGCAGTTTCTTGGGAAC
GCCGGCGGCGATTCATCCGTTTTCCGAGGAACAAGATCGTCGTCGGTGCTGAACATGGAGGAGAGC
TCGTTAAAACGACAGATTTTCAGCGGCGGCGGCGGCGATGAATTCTACGACGAGGAATACTACGAC
GAGCAGTTGTTGCCTGAGAAGAAGCGCCGACTCACCGCCGAGCAGGTTCACTTGCTTGAGAAGAGC
TTCGAGGCTGAGAACAAGCTTGAGCCTGAGCGAAAGGCTGAGCTGGCGAAGAAGCTCGGATTGCAG
CCGAGGCAAGTCGCCATTTGGTTCCAAAACCGCCGAGCACGGTGGAAGACTAAGCAGTTAGAGAGG
GACTACGACAAGCTTAAGTCTTCCTATGATTCTCTTCTCTCAACCTACGACTCTATTCGCCAGGAA
AACGACAAGCTCAAAGCCGAGCTCCTTTCCCTGAACGAGAAATTGCAACCCAAAGACGACGACGAC
CCATCGGCCGAAATAGGTCGAAATCTCAGTTCATCGTCGCCGCCTGTCGACGCGGCTGAGCCGCCG
TGCCTGAAGCTGACGGTGAAGGTGGAGGACCGCCTGAGCACGGGGAGCAACGGCAGCGCAGTAATG
GACGGCGACGGACCTCAGCAGCTCCTCGACGACAGCGGCGACTCGTACTTCGAGAACGACGAGGAA
TACGACTGCGCCGCCGCAAGTTTGGCTGCTGCGAAGGAGGACGACGGCAGCGATGAGGCGGGTGT
TACTTCACCGAGGCTCTCGCGGCGGAGGAGGAGGAGGCGCCGTTTGCTTGGTGTATTTGGTCTTAA
```

SEQ ID NO: 22 Craterostigma plantagineum CPHB-5 translated amino acid sequence
```
MNSARIFFDPSSHGNMLQFLGNAGGDSSVFRGTRSSSVLNMEESSLKRQIFSGGGGDEFYDEEYYD
EQLLPEKKRRLTAEQVHLLEKSFEAENKLEPERKAELAKKLGLQPRQVAIWFQNRRARWKTKQLER
DYDKLKSSYDSLLSTYDSIRQENDKLKAELLSLNEKLQPKDDDDPSAEIGRNLSSSSPPVDAAEPP
CLKLTVKVEDRLSTGSNGSAVMDGDGPQQLLDDSGDSYFENDEEYDCAAASLAAAKEDDGSDEGGC
YFTEALAAEEEEAPFAWCIWS
```

SEQ ID NO: 23 Gossypium hirsutum Goshi_hox5 cDNA sequence DT465649, CD486134
```
ATGGAGTCTGGCCGTCTTTTTTTCAATCCCTCCACTACCCACCGCAACATGTTGCTTCTCGGGAAC
ACTGAACCCATCTTTCGAGGGGCAAGAACAATGGTTAGCATGGAGGAAAACCCAAAGAAGCGACTG
TTCTTCAGCTCGCCGGAGGATTTGTACGACGAAGAGTACTACGACGAGCAGTTGCCCGAGAAAAAG
CGTCGCCTTACGTCGGAGCAGGTGTATCTGCTAGAGAAGAGCTTTGAGGCAGAGAACAAGCTGGAG
```

FIGURE 4 (continued)

```
CCGGAGAGGAAGAGCCAGTTGGCCAAGAAGTTAGGACTGCAACCAAGGCAGGTGGCGGTATGGTTC
CAGAACCGCCGTGCAAGGTGGAAGACAAAGCAGCTTGAAAGGGACTATGACCTCCTCAAATCTTCC
TTTGATTCCCTTCAGTCCAATTATGACACTATTCTCAAAGAAAATGAGAAGCTCAAATCTGAGGTA
GCTTCCTTGACTGAAAAACTACAAGCCAAAGATGTGGCAACAGAAGCAATAGCAGGTGAAAAGGAT
GAAGGGTTAGCAGCTGAGATGGCCTCCGCCCTCCAATTCAGTATGAAGGTGGAGGACCGTCTTAGT
AGCGGCAGTGTCGGAAGCGCGGTGGTGGATGAGGATGCCCCACAGCTGGTGGACAGCGGCAATTCC
TACTTTCCAAGCGATGAATACTCCAGAGGCATTGGCCCTTTCGATGGGGTTCAGTCGGAAGATGAG
GATGGCAGTGATAATTGCGGGAGTTACTTCTCCGATGTGTTCGCAACCACAGAGCAGGGAGCATTA
GGATTGTGGGCCTGGNTCTAA
```

SEQ ID NO: 24 Gossypium hirsutum Goshi_hox5 translated amino acid sequence
```
MESGRLFFNPSTTHRNMLLLGNTEPIFRGARTMVSMEENPKKRLFFSSPEDLYDEEYYDEQLPEKK
RRLTSEQVYLLEKSFEAENKLEPERKSQLAKKLGLQPRQVAVWFQNRRARWKTKQLERDYDLLKSS
FDSLQSNYDTILKENEKLKSEVASLTEKLQAKDVATEAIAGEKDEGLAAEMASALQFSMKVEDRLS
SGSVGSAVVDEDAPQLVDSGNSYFPSDEYSRGIGPFDGVQSEDEDGSDNCGSYFSDVFATTEQGAL
GLWAWX
```

SEQ ID NO: 25 Lycopersicon esculentum Lyces_hox5 cDNA sequence BT014213.1
```
ATGGGATCTGGGCATATATTTTTCGACCCGTCGTCGTGTCACGGCAACATGCTGTTCCTTGGGAGC
GGAGATCCTGTTTTCCGAGGACCAAGATCGACGATGATGAAGATGGAGGACTCCTCGAAGAGGCGA
CCCTTCTTTAGCTCGCCGGAGGATCTATATGACGAGGAATACTACGACGAGCAGTCACCGGAGAAG
AAGCGCCGTCTCACTCCTGAGCAGGTGCACTTGTTGGAGAAGAGCTTTGAGACAGAAAACAAGCTG
GAGCCCGAGCGCAAAACCCAGCTGGCCTANAAGCTGGGGCTGCAGCCCAGACAGGTGGCTGTATGG
TTCCAAAACCGCCGTGCCCGGTGGAAGACCAAGCAGCTCGAGAGGGATTATGATCAGCTCAAATCC
TCTTATGACTCCCTTCTCTCTGATTTTGACTCCGTTCGCAAGATAACGATAAGCTCAAATCTGAG
GTTGTTTCATTGATGGAAAAGTTACAGGGGAAAGTGGTTGGAGGAGCAGGGGGAAATGAAAAATCT
GACATCTTGGAGGTGGATGCTATGACGATCCTTCAAGTGAAGGTGAAGGCTGGGGACCGGTTGAGC
AGTGGCAGTGGTGGGAGCGCGGTGGTAGATGAGCATAGTTCACAGCTGGTGGACAGTGGGGACTCA
TATTTTCACACTGATCATGAGGAGTATCCAGGGCCTGGAGGATGCAATGTTCCTCCACCCATGGAT
GGTTTACAATCGGAGGAAGATGATGGTAGTGATGATCATGGCAGTTGCCATGGCTACTTCTCTAAC
GTCTTTGTGGCAGAAGAGCAGCACCATGAACAAGGAGAAGAGCCTATTGGATGGTTCTGGTCTTAA
```

SEQ ID NO: 26 Lycopersicon esculentum Lyces_hox5 translated amino acid sequence
```
MGSGHIFFDPSSCHGNMLFLGSGDPVFRGPRSTMMKMEDSSKRRPFFSSPEDLYDEEYYDEQSPEK
KRRLTPEQVHLLEKSFETENKLEPERKTQLAXKLGLQPRQVAVWFQNRRARWKTKQLERDYDQLKS
SYDSLLSDFDSVRKDNDKLKSEVVSLMEKLQGKVVGGAGGNEKSDILEVDAMTILQVKVKAGDRLS
SGSGGSAVVDEHSSQLVDSGDSYFHTDHEEYPGPGGCNVPPPMDGLQSEEDDGSDDHGSCHGYFSN
VFVAEEQHHEQGEEPIGWFWS
```

SEQ ID NO: 27 Lycopersicon esculentum VaHOX1 cDNA sequence X94947
```
ATGGCTCCAGGGATTCTCTATGGTGGTTCTTCTAATTTCGATGGCGTTTTTACTCAAAAACAGAGA
GACGTGTTTCTTCATCTACTGCACCGAAGGGCATCTTGGTTCCCTTTTTGCCCCTGCCTCTTCT
TCTTCTAATTTCTTGGGATCCAGTTCTATGGTGAGTTTTCGCGGTGTTAATGGAGGGAAGAGATCA
TTCTTTGATTCGTTCGATCAGGATGACAATGAAGCTGATGAATTGGGGGAATATCTTCATCAAGCG
GAGAAGAAGAGGCGACTTACTGACAACCAAGTTCAGTTTCTTGAAGAGTTTTGGGGAAGAGAAC
```

FIGURE 4 (continued)

```
AAACTTGAACCAGAAAGAAAAGTTCAGCTTGCTAAAGAACTTGGTCTGCAGCCTCGCCAAATTGCA
ATTTGGTTTCAGAATCGTCGTGCGCGATGGAAGACTAAGCAGCTCGAGAAAGATTATGATGAATTG
AGGAATAGATACGATACTCTGAAATCAAATTACAATAATCTTCTCAAGGAAAAAGAAGATCTTCGA
ACTGAAGTTTTCCGTCTCACCGGTAAGCTGTTTATCAAAGAGAAAGGAAATGGGCAATTGGATTTG
CGCGATGAACACAAACACTCCAATGCATTGGCAAAAGAAACCGTGGTTGATCCAATGTCCAATGTA
CCAGCTCTGGTTGTTAAGCACCAGCAGGAAGATTTAAGCTCTGCTAAGAGTGATGTTTTCGACTCA
GAAAGCCCACGTTACACCAGTAGAATGCATTCCTCAGTCGTAGATCAGGATGATTCTGCTCGCGCA
TTTGAAACTGATCAGTCGGATTCATCTCAGGATGATGATGAAAACTTCAGCAAGAATATGCTTTCT
ACTGCCAACCTACTTGGCAAAGACGCGGATGATGATTATCCCGCGACATCATCAAATTTGAGTTAC
TTTGGATTTCCAGTTGAAGACCAAGGTTTTGGTTTCTGGACTTATTAA

SEQ ID NO: 28 Lycopersicon esculentum VaHOX1 translated amino acid
sequence
MAPGILYGGSSNFDGVFTQKQRDVFSSSTAPKGHLGSLFAPASSSSNFLGSSSMVSFRGVNGGKRS
FFDSFDQDDNEADELGEYLHQAEKKRRLTDNQVQFLEKSFGEENKLEPERKVQLAKELGLQPRQIA
IWFQNRRARWKTKQLEKDYDELRNRYDTLKSNYNNLLKEKEDLRTEVFRLTGKLFIKEKGNGQLDL
RDEHKHSNALAKETVVDPMSNVPALVVKHQQEDLSSAKSDVFDSESPRYTSRMHSSVVDQDDSARA
FETDQSDSSQDDDENFSKNMLSTANLLGKDADDDYPATSSNLSYFGFPVEDQGFGFWTY SEQ ID NO: 29 Medicago sativa Medsa_hox16 cDNA sequence CB892061,
CA858059
ATGGCGGGTGGGAGAGTTTTTTCAAATGGTCCTGCAAATATTTCAAATATAAATATGAATATTTTG
CTTCAGAATCAACAACAAACTCCTCGTGGAAACTCTTCTCAACAACCTCTTGATTCTCTTTTCCTT
TCTTCTTCTGCTTCTTTCTTTGGTTCAAGATCTATGGTGAGTTTTGAAGATGTTCAAGGAAGGAAA
AGGCGCAACAGGTCTTTCTTTGGAGGATTTGATCTTGACGAAAACGGAGAGGATGAGATGGATGAG
TACTTTCATCAATCCGAGAAGAAACGGCGTCTCTCAGTGGATCAAGTTCAGTTTCTTGAGAAAAGC
TTTGAGGAGGACAACAAACTTGAACCAGAGAGGAAAACCAAGCTAGCTAAAGACCTTGGTTTGCAG
CCACGGCAAGTTGCTATTTGGTTTCAAAACCGTCGTGCAAGGTGGAAGACTAAACAGCTTGAGAAG
GATTATGATTCTCTTAATGATGGTTATGAGTCTCTTAAGACAGAGTATGACAACCTTCTCAAAGAG
AAAGATAGGTTACAATCTGAGGTGGCAAGCCTAACTGAAAAGGTACTTGAAAGAGAGAAACAAGAG
GGAAAATTCAAACAAGGTGAAAGTGAAACAAAGGAATTCTTGAAGGAACCAACAATTAATAAGCCT
TTGGTTGATTCAGTTTCTGAGGGTGAAGGATCCAAATTGTCAATTGTTGAGGCTTCTAATAATAAT
AATAATAATAACAAACTTGAAGATATTAGTTCAGCAAGGAGTGACATATTGGATTGTGAAAGTCCA
CGCTACACTGATGGAGTGTTAGAGACATGTGATTCTTCCTATGTATTTGAACCTGAATATCAATCG
GACCTATCACAAGATGAAGAAGATCACAATTTATTGCCTCCTTACATCTTTACAAAACTTGAAGAT
GTGAATTACTCCGACCCGCCACATAATTCAACAAGTTATGGATTTCAAGAGGAAGATCATCATCAA
GCTCTTTGGCCTTGGTCTTATTAG

SEQ ID NO: 30 Medicago sativa Medsa_hox16 translated amino acid
sequence
MAGGRVFSNGPANISNINMNILLQNQQQTPRGNSSQQPLDSLFLSSSASFFGSRSMVSFEDVQGRK
RRNRSFFGGFDLDENGEDEMDEYFHQSEKKRRLSVDQVQFLEKSFEEDNKLEPERKTKLAKDLGLQ
PRQVAIWFQNRRARWKTKQLEKDYDSLNDGYESLKTEYDNLLKEKDRLQSEVASLTEKVLEREKQE
GKFKQGESETKEFLKEPTINKPLVDSVSEGEGSKLSIVEASNNNNNNKLEDISSARSDILDCESP
RYTDGVLETCDSSYVFEPEYQSDLSQDEEDHNLLPPYIFTKLEDVNYSDPPHNSTYGFQEEDHHQ
ALWPWSY
```

FIGURE 4 (continued)

SEQ ID NO: 31 Aquilegia formosa x Aquilegia pubescens Aqufo_hox5
cDNA sequence DT758247
ATGGATTCAACAACAAGCCGTCTTTTCTTTGATGGTTCCTGCCATGGGAACATGTTGCTTTTAGGG
AGTGGAGATCCCGTTCTTCGAGGTTCAAGATCATTCATTAATATGGAAGATTCTTTGAAAAGACGT
CCTTTTTATAGTTCAACAGATGAACTAATTGAAGAGGAGTTTTATGATGAACAGCTACCTGAAAAG
AAACGTCGTCTTACTTCTGAGCAGGTTCATCTATTGGAGAAGAGCTTTGAGACAGAGAACAAGCTG
GAACCAGATCGTAAGACCCAGCTTGCTAAGAAGCTTGGGTTGCAACCGAGACAAGTTGCAGTTTGG
TTTCAGAATAGACGAGCTCGTTGGAAGACTAAGCAACTAGAGAGAGATTATGATCTTCTTAAAGCT
TCTTATGATTCCCTTCGTTCTGATTACGATGACATTGTTAAAGAGAATGAGAAGCTCAAATCTGAG
GTGGTTTCCTTAACTGGGAAGTTGCAGGTCAAGGAGGGAGCTGGGATGGAGTTAAATCAGATATCT
GACCCACCACTCTCCACTGAAGAAAATGTTGATGTAACTACGATGCAATTTAATGTTAAGGTTGAG
GATCGCTTGAGCTCTGGCAGTGGGGTAAGTGCTGTGGTTGATGAGGAATGTCGACAGCTTGTTGAC
AGTGTTGATTCCTATTTCCCTGGCGATGACTATGGTCAATGCATAGGCCCAGTAGATGGAGTCCAG
TCAGAAGAAGATGACATTAGTGACGACAGCCGGAGCTATTTCTCAGATGTCTTTCCAGCTGCACCA
GAGCAGAACCACCAGGAGAGTGAGACATTGGGTTGGTGGGACTGGGCTTAA

SEQ ID NO: 32 Aquilegia formosa x Aquilegia pubescens Aqufo_hox5
translated amino acid sequence
MDSTTSRLFFDGSCHGNMLLLGSGDPVLRGSRSFINMEDSLKRRPFYSSTDELIEEEFYDEQLPEK
KRRLTSEQVHLLEKSFETENKLEPDRKTQLAKKLGLQPRQVAVWFQNRRARWKTKQLERDYDLLKA
SYDSLRSDYDDIVKENEKLKSEVVSLTGKLQVKEGAGMELNQISDPPLSTEENVDVTTMQFNVKVE
DRLSSGSGVSAVVDEECRQLVDSVDSYFPGDDYGQCIGPVDGVQSEEDDISDDSRSYFSDVFPAAP
EQNHQESETLGWWDWA SEQ ID NO: 33 Oryza sativa GOS2 promoter
AATCCGAAAAGTTTCTGCACCGTTTTCACCCCCTAACTAACAATATAGGGAACGTGTGCTAAATAT
AAAATGAGACCTTATATATGTAGCGCTGATAACTAGAACTATGCAAGAAAAACTCATCCACCTACT
TTAGTGGCAATCGGGCTAAATAAAAAGAGTCGCTACACTAGTTTCGTTTTCCTTAGTAATTAAGT
GGGAAAATGAAATCATTATTGCTTAGAATATACGTTCACATCTCTGTCATGAAGTTAAATTATTCG
AGGTAGCCATAATTGTCATCAAACTCTTCTTGAATAAAAAAATCTTTCTAGCTGAACTCAATGGGT
AAAGAGAGATTTTTTTAAAAAAATAGAATGAAGATATTCTGAACGTATTGGCAAAGATTTAAA
CATATAATTATATAATTTTATAGTTTGTGCATTCGTCATATCGCACATCATTAAGGACATGTCTTA
CTCCATCCCAATTTTTATTTAGTAATTAAAGACAATTGACTTATTTTTATTATTTATCTTTTTCG
ATTAGATGCAAGGTACTTACGCACACACTTTGTGCTCATGTGCATGTGTGAGTGCACCTCCTCAAT
ACACGTTCAACTAGCAACACATCTCTAATATCACTCGCCTATTTAATACATTTAGGTAGCAATATC
TGAATTCAAGCACTCCACCATCACCAGACCACTTTTAATAATATCTAAAATACAAAAAATAATTTT
ACAGAATAGCATGAAAAGTATGAAACGAACTATTTAGGTTTTTCACATACAAAAAAAAAAAGAATT
TTGCTCGTGCGCGAGCGCCAATCTCCCATATTGGGCACACAGGCAACAACAGAGTGGCTGCCCACA
GAACAACCCACAAAAAACGATGATCTAACGGAGGACAGCAAGTCCGCAACAACCTTTTAACAGCAG
GCTTTGCGGCCAGGAGAGAGGAGGAGAGGCAAAGAAAACCAAGCATCCTCCTCCTCCCATCTATAA
ATTCCTCCCCCTTTTCCCCTCTCTATATAGGAGGCATCCAAGCCAAGAAGAGGGAGAGCACCAAG
GACACGCGACTAGCAGAAGCCGAGCGACCGCCTTCTTCGATCCATATCTTCCGGTCGAGTTCTTGG
TCGATCTCTTCCCTCCTCCACCTCCTCCTCACAGGGTATGTGCCCTTCGGTTGTTCTTGGATTTAT
TGTTCTAGGTTGTGTAGTACGGGCGTTGATGTTAGGAAAGGGGATCTGTATCTGTGATGATTCCTG
TTCTTGGATTTGGGATAGAGGGGTTCTTGATGTTGCATGTTATCGGTTCGGTTTGATTAGTAGTAT
GGTTTTCAATCGTCTGGAGAGCTCTATGGAAATGAAATGGTTTAGGGTACGGAATCTTGCGATTTT
GTGAGTACCTTTTGTTTGAGGTAAAATCAGAGCACCGGTGATTTGCTTGGTGTAATAAAAGTACG
GTTGTTTGGTCCTCGATTCTGGTAGTGATGCTTCTCGATTTGACGAAGCTATCCTTTGTTTATTCC

FIGURE 4 (continued)

```
CTATTGAACAAAAATAATCCAACTTTGAAGACGGTCCCGTTGATGAGATTGAATGATTGATTCTTA
AGCCTGTCCAAAATTTCGCAGCTGGCTTGTTTAGATACAGTAGTCCCCATCACGAAATTCATGGAA
ACAGTTATAATCCTCAGGAACAGGGGATTCCCTGTTCTTCCGATTTGCTTTAGTCCCAGAATTTTT
TTTCCCAAATATCTTAAAAAGTCACTTTCTGGTTCAGTTCAATGAATTGATTGCTACAAATAATGC
TTTTATAGCGTTATCCTAGCTGTAGTTCAGTTAATAGGTAATACCCCTATAGTTTAGTCAGGAGAA
GAACTTATCCGATTTCTGATCTCCATTTTTAATTATATGAAATGAACTGTAGCATAAGCAGTATTC
ATTTGGATTATTTTTTTTATTAGCTCTCACCCCTTCATTATTCTGAGCTGAAAGTCTGGCATGAAC
TGTCCTCAATTTTGTTTTCAAATTCACATCGATTATCTATGCATTATCCTCTTGTATCTACCTGTA
GAAGTTTCTTTTTGGTTATTCCTTGACTGCTTGATTACAGAAAGAAATTTATGAAGCTGTAATCGG
GATAGTTATACTGCTTGTTCTTATGATTCATTTCCTTTGTGCAGTTCTTGGTGTAGCTTGCCACTT
TCACCAGCAAAGTTC

SEQ ID NO: 34 primer prm6000
GGGGACAAGTTTGTACAAAAAAGCAGGCTTAAACAATGGATCCCGGCCG

SEQ ID NO: 35 primer prm6001
GGGGACCACTTTGTACAAGAAAGCTGGGTGATCAGCTCCAGAACCAGG

SEQ ID NO: 36 Oryza sativa Orysa_hox4 cDNA sequence AF145728
ATGAAGCGACCCGGCGGTGCCGGCGGCGGCGGAGGCAGCCCATCGCTCGTCACGATGGCTAATTCT
AGTGATGATGGATATGGAGGGGTTGGGATGGAGGCGGAGGGGGACGTGGAGGAGGAGATGATGGCG
TGCGGCGGCGGCGGGGAGAAGAAGCGGCGGCTGAGCGTGGAGCAGGTTCGCGCGCTGGAGCGGAGC
TTCGAGGTGGAGAACAAGCTTGAGCCTGAGCGGAAGGCGCGGCTGGCGCGCGACCTCGGCCTGCAG
CCGCGCCAGGTCGCCGTCTGGTTCCAGAACCGCCGCGCGCGGTGGAAGACCAAGCAGCTCGAGCGC
GACTACGCCGCGCTCCGCCATTCCTACGACTCCCTGCGCCTCGATCACGACGCGCTCCGCCGCGAC
AAGGACGCCCTCCTCGCCGAGATCAAGGAGCTGAAGGCGAAGCTCGGGGACGAGGAGGCGGCGGCG
AGCTTCACGTCGGTGAAGGAGGAGCCGGCGGCCTCCGACGGGCCACCGGCGGCGGGATTTGGGTCG
TCCGACAGCGACTCAAGCGCGGTGCTGAACGACGTGGACGCGGCCGGCGCCGCGCCCGCGGCGACG
GACGCGCTGGCTCCGGAGGCGTGCACGTTTCTCGGTGCGCCGCCCGCCGCGGGCGCGGGCGCGGGC
GCAGCGGCGGCGGCGAGCCACGAGGAGGTGTTCTTCCACGGCAATTTCCTCAAGGTGGAGGAGGAC
GAGACGGGGTTCCTCGACGACGACGAGCCGTGCGGCGGGTTCTTCGCCGACGATCAGCCCCCGCCG
CTCTCGTCGTGGTGGGCCGAACCCACGGAGCACTGGAACTGA SEQ ID NO: 37 Oryza sativa Orysa_hox4 translated amino acid
sequence
MKRPGGAGGGGGSPSLVTMANSSDDGYGGVGMEAEGDVEEEMMACGGGGEKKRRLSVEQVRALERS
FEVENKLEPERKARLARDLGLQPRQVAVWFQNRRARWKTKQLERDYAALRHSYDSLRLDHDALRRD
KDALLAEIKELKAKLGDEEAAASFTSVKEEPAASDGPPAAGFGSSDSDSSAVLNDVDAAGAAPAAT
DALAPEACTFLGAPPAAGAGAGAAAAASHEEVFFHGNFLKVEEDETGFLDDDEPCGGFFADDQPPP
LSSWWAEPTEHWN SEQ ID NO: 38 Oryza sativa Orysa_hox6 cDNA sequence AK103160
ATGGATGGGGAGGAGGACAGCGAGTGGATGATGATGGACGTTGGAGGGAAGGGCGGGAAGGCGGC
GGCGGCGGCGGCGCGGCGGACAGGAAGAAGCGGTTCAGCGAGGAGCAGATCAAGTCGCTGGAGTCC
ATGTTCGCGACGCAGACCAAGCTGGAGCCGAGGCAGAAGCTGCAGCTCGCCAGGGAGCTCGGCCTG
CAGCCTCGCCAGGTCGCCATCTGGTTCCAGAACAAGCGCGCGCGGTGGAAGTCCAAGCAGCTCGAG
CGCGAGTACTCCGCCCTCCGCGACGACTACGACGCCCTCCTCTGCAGCTACGAGTCCCTCAAGAAG
GAGAAGCTCGCCCTCATCAAGCAGCTGGAGAAGCTGGCGGAGATGCTGCAGGAGCCACGGGGGAAG
```

FIGURE 4 (continued)

```
TACGGCGATAATGCCGGGGACGACGCGCGGTCGGGCGGCGTCGCCGGCATGAAGAAGGAGGAGTTC
GTCGGCGCGGGCGGCGCCGCCACGCTCTACTCGTCGGCCGAGGGTGGCGGGACGACGACGACGACG
ACGGCCAAGTTGATGCCCCACTTCGGCAGCGACGACGTCGACGCGGGGCTCTTCCTCCGGCCGTCG
TCGCAGCATCATCCGCCGCCGCCGCACGCCGGTGCCGGCTTCACGTCCTCCGAGCCGGCCGCCGAC
CACCAGTCCTTCAACTTCCACTCGAGCTGGCCGTCGTCCACGGAGCAGACCTGCAGCAGCACGCCA
TGGGTGGGAATTCGAGAGCGAGTGA
```

SEQ ID NO: 39 Oryza sativa Orysa_hox6 translated amino acid sequence
```
MDGEEDSEWMMMDVGGKGGKGGGGGGAADRKKKRFSEEQIKSLESMFATQTKLEPRQKLQLARELGL
QPRQVAIWFQNKRARWKSKQLEREYSALRDDYDALLCSYESLKKEKLALIKQLEKLAEMLQEPRGK
YGDNAGDDARSGGVAGMKKEEFVGAGGAATLYSSAEGGGTTTTTTAKLMPHFGSDDVDAGLFLRPS
SQHHPPPPHAGAGFTSSEPAADHQSFNFHSSWPSSTEQTCSSTPWWEFESE
```

SEQ ID NO: 40 Populus tremuloides Poptr_HOX16_1 cDNA sequence
```
ATGGCGGGTGGTACCGGTGGTTCTAATTCCAATTTGTCTGTTTTGCTTCAAAGCCAAAGAGGCCCT
TGTGCTGCTTCACAACCTCTTGAATCTTTTTTCCTTTCTGGCTCTTCTCCTTCTTTTCTTGGTTCA
AGATCCATGATGAGTTTTGAAGATGTTCATCAAGCAAACGGATCAACCAGGCCTTTTTTCCGCTCG
TTTGATCACGAAGACAATGGAGACGATGATCTGGATGAATATTTTCATCAACCTGAAAAGAAGAGG
AGACTTACTGTTGATCAAGTTCAGTTTCTTGAAAAGAGTTTTGAGCTTGAGAACAAGCTTGAACCT
GAAAGGAAAATCCAGCTTGCAAAGGATCTTGGCCTTCAGCCGCGTCAGGTTGCTATATGGTTTCAA
AACCGCCGAGCAAGATGGAAGACTAAACAGCTGGAAAAGGATTATGACGTTTTGCAATCTAGCTAC
AATAGCCTTAAGGCTGACTATGACAACCTCCTCAAGGAGAAGGAGAAACTAAAAGCTGAGGTTAAT
CTTCTCACCGACAAGTTGCTCCTCAAAGAGAAAGAGAAGGGAATCTCAGAATTGTCTGATAAAGAT
GCATTATCGCAAGAGCCACCTAAAAGGGCTATAGCTGATTCAGCTTCCGAGGGTGAAGTGTCGAAA
ATCTCAACAGTGGCCTGTAAGCAGGAAGATATCAGCTCAGCCAAAAGCGACATATTTGATTCAGAC
AGCCCACATTACGCTGATGGGGTGCATTCCTCACTCTTAGAGGCAGGAGATTCTTCATATGTTTTC
GAACCCGATCAATCAGATTTGTCACAAGATGAAGAAGATAACTTTAGCAAGAGCTTATTGCCTCCA
TACGTCTTTCCGAAGCTTGAAGATGACGATTACTCTGACCCGCCTGCAAGTTTTGAAGATCATGCC
TTTTGGTCCTGGTCATACTAA
```

SEQ ID NO: 41 Populus tremuloides Poptr_HOX16_1 translated amino acid sequence
```
MAGGTGGSNSNLSVLLQSQRGPCAASQPLESFFLSGSSPSFLGSRSMMSFEDVHQANGSTRPFFRS
FDHEDNGDDDLDEYFHQPEKKRRLTVDQVQFLEKSFELENKLEPERKIQLAKDLGLQPRQVAIWFQ
NRRARWKTKQLEKDYDVLQSSYNSLKADYDNLLKEKEKLKAEVNLLTDKLLLKEKEKGISELSDKD
ALSQEPPKRAIADSASEGEVSKISTVACKQEDISSAKSDIFDSDSPHYADGVHSSLLEAGDSSYVF
EPDQSDLSQDEEDNFSKSLLPPYVFPKLEDDDYSDPPASFEDHAFWSWSY
```

SEQ ID NO: 42 Populus tremuloides Poptr_HOX16_2 cDNA sequence
```
ATGGCGGCTTGTGGTGGTGGTGGTGGTGGTTCTAATCCCAATTTGTCTGTTTTAGTTCAAAGCCAA
AGAGGCCCTTGTGCTGCTTCTCAACCTCTTGAAGCTTTTTCCTTTCTGGCTCTTCTCCTTCTTTT
CTTGGTTCAAGATCCATGATGAGTTTTGCAGATGTTCACCAAGCAAATGGATCAACTAGACCGTTT
TTCCGCCCATATGATCACGAAGACAACGGCGACGATGATTTGGATGAATATTTTCATCAACCTGAA
AAGAAGAGGAGACTTACTGTTGATCAAGTTCAGTTTCTTGAAAGAAGTTTTGAGGTTGAGAACAAG
CTTGAACCCGAAAGGAAAATCCAGCTGGCGAAGGATCTTGGCTTGCAGCCTCGGCAGGTTGCCATA
TGGTTTCAAAACCGCCGGGCAAGATGGAAGACGAAACAGCTTGAAAAAGATTATGAGGTTCTGCAA
```

```
TCTAGCTACAATGGCCTTAAGGCTGACTACGACAACCTCTTCAAGGAGAAGGAGAAACTAAAAGCT
GAGGTTAATCTTCTCACCAACGAGTTGCTCCTTAAAGAGAAAGAGAAAGGAAGCTCAGAATTGTCT
GATAAAGATGCATTATCTCAAGAGCCACCCAAAAAGGCAATAGCCGATTCAGCTTCAGAGGGTGAA
GTGTCGAAAACTTCAACCGTGGCCTGCCAGCAGGAAGATATTAGCTCAGCCAAAAGTGATATGTTT
GATTCAGACAGCCCACATTTTGCGGATGGGGTACATTCCTCACTCTTAGAGGCAGGTGATTCTTCA
CATGTCTTCGAGCCCGACCAATCGGATTTATCACAAGATGAAGAAGATAACTTGAGCAAGAGTCTT
TTGCCTCCGTACGTCTTTCCAAAGCTTGAAGATGGTGATTACTCTGACCCGCCAGCAAGTTTTGAA
GATCATGCCTTTTGGTGCTGGTCATACTAA
```

SEQ ID NO: 43 Populus tremuloides Poptr_HOX16_2 translated amino acid sequence
```
MAACGGGGGGSNPNLSVLVQSQRGPCAASQPLEAFFLSGSSPSFLGSRSMMSFADVHQANGSTRPF
FRPYDHEDNGDDDLDEYFHQPEKKRRLTVDQVQFLERSFEVENKLEPERKIQLAKDLGLQPRQVAI
WFQNRRARWKTKQLEKDYEVLQSSYNGLKADYDNLFKEKEKLKAEVNLLTNELLLKEKEKGSSELS
DKDALSQEPPKKAIADSASEGEVSKTSTVACQQEDISSAKSDMFDSDSPHFADGVHSSLLEAGDSS
HVFEPDQSDLSQDEEDNLSKSLLPPYVFPKLEDGDYSDPPASFEDHAFWCWSY
```

SEQ ID NO: 44 Populus tremuloides Poptr_HOX16_3 cDNA sequence
```
ATGGCGGGTGATAAAGACTGTGGCAGTTCTAAAATGACCATTTTTCTTCGAAACGGCAGGCTCCCT
CCTTGTGAATCTCTCTGTATTCTCACCTCTTTTAGCACTCTTCATGGTGCAAAATCTATGGTTAAT
TTTAGGAATGATGGAGGAGACACTGTAGACATGTCTTTTTTCCAACCACATGTCAAAGAAGAAAGT
AGCGATGAGGATTATGATGCGCACCTTAAGCCATCTGAAAAGAAAAGGCGGCTTACAGCTGCTCAA
GTCCAGTTTCTTGAGAAGAGCTTTGAGGCGGAGAATAAGCTTGAACCAGAGAGGAAGATGCAGCTT
GCTAAAGAACTCGGCTTGCAGCCTCGCCAGGTTGCAATATGGTTTCAAAACCGTAGAGCTCGGTTC
AAGAACAAGCAGCTGGAAAGGGACTACGACTCCTTGAGAATCAGCTTTGACAAACTCAAGGCTGAT
TATGACAAACTCCTCCTCGAGAAGCAGAATTTGAAAAACGAGCTTCTTTCACTGAAAGAAAAATTG
CTTAGCAGAGAGGAAAGTATGGAAAGTTCAGAACCATTTGATGTCATCCATTCACCGGATGCAGAA
CTTGAGCCTATTCCTGATACAGTGTCTGAAAATGTTTCCGCCATTGTGCCAATGGTGACACCCAAA
CAAGAAGAAAGTTCAGCTAAAAATGATGTTTTCAACTCAGACAGCCCACGTTCATTTTTGGAGCCC
CGTGATTGTTATCGTGTTTTCGAGTCAGACCAACCAGATTTTTCCCAAGTTGAAGAAGATAATCTC
ACCAGGAGCTTTCTACCCCCTCCGTACTTTCCAAAACTCTACCGAGAGCCACCTGCAAGTTCACGT
AATTTTGAATTCTCAGCGGAAGATCAGCCCTTTTGGTCCTGGATTTACTGA
```

SEQ ID NO 45: Populus tremuloides Poptr_HOX16_3 translated amino acid sequence
```
MAGDKDCGSSKMTIFLRNGRLPPCESLCILTSFSTLHGAKSMVNFRNDGGDTVDMSFFQPHVKEES
SDEDYDAHLKPSEKKRRLTAAQVQFLEKSFEAENKLEPERKMQLAKELGLQPRQVAIWFQNRRARF
KNKQLERDYDSLRISFDKLKADYDKLLLEKQNLKNELLSLKEKLLSREESMESSEPFDVIHSPDAE
LEPIPDTVSENVSAIVPMVTPKQEESSAKNDVFNSDSPRSFLEPRDCYRVFESDQPDFSQVEEDNL
TRSFLPPPYFPKLYREPPASSRNFEFSAEDQPFWSWIY
```

SEQ ID NO 46: Medicago truncatula Medr_HOX16_1 cDNA sequence
```
ATGGCAGGTGGCAAGCTTTTTGGTGGTTCTAATATGTCACTTTTGCTTCAAAATGAAAGACTCCCT
TGTACTTCTGAAGTCCTTGAATCTCTTTGGGTTCACACCCCTGCTTCTTTTCAAGGTTCAAATTCA
GTGGTTAATTTTGAGAATGGTGGTGGTAGCAACAGAGTGGTAACAGATAGACCCTTCTTTCAACAA
CTTGAGAAAGAAGAGAATTGTGGTGATGAAGATTATGAAGCATGCTACCATCAACAAGGAAAGAAA
AGGAGGCTTTCAAGTGAACAAGTTCAATTTCTTGAAAAGAGTTTTGAGGTAGAAAACAAGCTTGAA
CCTGATAGGAAAGTTCAACTTGCAAAAGAGCTTGGTTTGCAA
```

FIGURE 4 (continued)

```
CCAAGACAAGTTGCTATATGGTTTCAAAACAGAAGGGCAAGGTTCAAAACTAAACAGCTTGAAAAA
GATTATGGCACATTGAAAGCTAGCTTTGATAGTCTCAAAGATGATTATGATAATCTTCTTCAAGAG
AATGACAAGTTAAAAGAAGAGGTGAATTCTCTCAAGAACAAATTGATCCCAAGAGATAAAGAAAAA
GTGAATTCAGAAGACAAATCATCACCAGAAGCAATCAATTCACCTCATAACAACATAGATCCAATG
GATATAATTTCAATTACAAATTCAGAAATGGGTCCAAAATGTCACTCCCTAATATGGTACTAAAA
TGTAAGCAAGAAGATGCCAATTCAGCTAAAAGTGATGTGCTTGATTCTGATAGCCCACATTGCAAT
GATGGGAACAATCTTTCTTCTTTCATAGAGCCTACAGATTCAGATTTCTCACAAGATGAAGAGGAT
AATGATAACTTGAGTCATAATCTTTTGACTCTTCCTTGCTTACCAAAAGTTGAAGATGTTTGCTAT
GATGACCCACATGAAAATTCTTGTAATTTTGGGTTCCCTGTTGAAGATCAAACCTTTTGTTTCTGG
CCTTATTGA
```

**SEQ ID NO 47: Medicago truncatula Medtr_HOX16_1 translated amino
acid sequence**
MAGGKLFGGSNMSLLLQNERLPCTSEVLESLWVHTPASFQGSNSVVNFENGGGSNRVVTDRPFFQQ
LEKEENCGDEDYEACYHQQGKKRRLSSEQVQFLEKSFEVENKLEPDRKVQLAKELGLQPRQVAIWF
QNRRARFKTKQLEKDYGTLKASFDSLKDDYDNLLQENDKLKEEVNSLKNKLIPRDKEKVNSEDKSS
PEAINSPHNNIDPMDIISITNSENGSKMSLPNMVLKCKQEDANSAKSDVLDSDSPHCNDGNNLSSF
IEPTDSDFSQDEEDNDNLSHNLLTLPCLPKVEDVCYDDPHENSCNFGPVEDQTFCFWPY

SEQ ID NO 48: Phaseolus vulgaris Phavu_HOX16 cDNA sequence
```
ATGGCGGGTGGCAAGCTTCATCCTGGTTCAAACATGTCACTTCTCCTCCAAAACGACAGGCTCCCT
TGCTCCTCTGAAGTCCTTGAGTCTCTTTGGGCTCACACCTCTAACGCTGCTTCCTTCCAAGGTTCA
AAATCTATGGTTGATTTTGAGAATGTTAGTGGGGGCAGGGTGACGGATAGGCCCTTTTTTCAAGCG
TTGGAGAAGGAAGATAACTGTGATGATGATTATGAGGGTTGCTTCCATCAACCGGGTAAGAAAAGG
AGGCTCACAAGCGAACAAGTTCAGTTCCTTGAAAGGAACTTTGAGGTCGAGAACAAGCTTGAACCT
GAAAGGAAGGTCCAACTTGCAAAGGAGCTTGGCTTGCAGCCAAGGCAAGTGGCTATATGGTTCCAA
AACCGAAGGGCAAGGTTCAAGACCAAGCAGCTAGAAAAAGATTATGGCACATTGAAAGCTAGCTAT
GACAGACTCAAAGGTGACTATGAAAGTCTTCTTCAAGAGAATGACAAGTTAAAAGCAGAGGTGAAT
TCTCTGGAGAGCAAATTGATTCTTAGAGATAAAGAGAAGGAGAATTCGGACGACAAGTCATCTCCT
GATGCTGTCAATTCACCCCACAAAGAGCCTATGGATTTAATTTCAAATTCAACATCTGAAAATGGG
ACCAAAGTGTCACTCCCTATTATGGTAACATGCAAGCAAGAAGATGCCAATTCAGCCAAAAGTGAT
GTGCTTGATTCGGACAGCCCACATTGCACTGATGGGAACCATCCCTCTTCATTCGTGGAGCCTGCT
GATTCCTCCCATGCTTTTGAACCAGACCACTCCGACTTCTCCCAAGATGAAGAGGATAATCTTAGT
GAAAGCCTTTTGACCCTCCCTTGCTTACCAAAGGTTGAAGAAGCCTGCTATGATGACCCTCCTGAA
AACCCTTGTAATTTTGGCTTCCATGTCGAGGATCAAACCTTCTGTTTCTGGCCCTATTGA
```

**SEQ ID NO 49: Phaseolus vulgaris Phavu_HOX16 translated amino acid
sequence**
MAGGKLHPGSNMSLLLQNDRLPCSSEVLESLWAHTSNAASFQGSKSMVDFENVSGGRVTDRPFFQA
LEKEDNCDDDYEGCFHQPGKKRRLTSEQVQFLERNFEVENKLEPERKVQLAKELGLQPRQVAIWFQ
NRRARFKTKQLEKDYGTLKASYDRLKGDYESLLQENDKLKAEVNSLESKLILRDKEKENSDDKSSP
DAVNSPHKEPMDLISNSTSENGTKVSLPIMVTCKQEDANSAKSDVLDSDSPHCTDGNHPSSFVEPA
DSSHAFEPDHSDFSQDEEDNLSESLLTLPCLPKVEEACYDDPPENPCNFGFHVEDQTFCFWPY

SEQ ID NO 50: Lotus corniculatus Lotco_Hox16 cDNA sequence
```
ATGGCGGGAGGGAGGGTCTTTAGCGGCGGTTCTGCTGCTCCTGCAAATGTTTCCGATACCAGTCTT
TTGCTTCAGAATCAACCTCCTGATTCTTCTCTCTTCCTCTCTACCTCTGCTTCTTTTCTCGGTTCA
AGATCCATGGTGAGCTTCGCAGATAATAAATTAGGGCAAACGCGGTCGTTCTTCTCCGCGTTTGAC
```

FIGURE 4 (continued)

```
CTCGATGAGAACGGCGATGAGGTCATGGACGAGTACTTTCACCAATCGGAGAAGAAGCGCCGTCTC
TCTGTTGACCAAGTTCAGTTTCTGGAGAAGAGCTTCGAGGTGGATAACAAGCTCGAACCTGACAGG
AAAACCAAGATTGCCAAGGACCTTGGTTTGCAGCCACGCCAAGTCGCAATCTGGTTCCAGAACCGC
CGTGCACGGTGGAAGACGAAACAGCTTGAGAAGGATTATGATTCTCTGCATAGTAGCTTTGAGAGT
CTCAAATCCAACTATGATAATCTTCTCAAGGAGAAAGACATGTTAAAAGCTGAGGTGGCAAGTCTC
ACTGAGAAGGTGCTTGCAAGAGAGAATTTGAAACAAGTTGAAAGTGAAACAAAGGGATTGGTTGAA
CCACCCCAAAGGCCTTTACTTGATTCAGTTTCAGAGGGTGAAGAATCTAAAGTCTCTGTTGGGGCT
TGTAAACATGAGGATATCAGTTCAGCCAGGAGTGAGAGTTTGGATTCTGATAGCCCACGTTACAGG
GATGGATATGGAGTTAACTCAGCAGTGCTAGAGACATGTGATTCTTCTTATGTGGTTGAACCTGAT
CAATCGGATATGTCACAGGATGAGGAAGACAACCTGACCAAGACCCTGTTGCCTCCATACATGTTT
TCCAAACTTGGAGATATGGATTACTCCGACCCGCCTGAAAGTTCATGTAATTTCGGATTTCCGGAG
GAAGATCATGCCCTTTGGTCATGGTCTTACTGA
```

SEQ ID NO 51: Lotus corniculatus Lotco_Hox16 translated amino acid sequence

```
MAGGRVFSGGSAAPANVSDTSLLLQNQPPDSSLFLSTSASFLGSRSMVSFADNKLGQTRSFFSAFD
LDENGDEVMDEYFHQSEKKRRLSVDQVQFLEKSFEVDNKLEPDRKTKIAKDLGLQPRQVAIWFQNR
RARWKTKQLEKDYDSLHSSFESLKSNYDNLLKEKDMLKAEVASLTEKVLARENLKQVESETKGLVE
PPQRPLLDSVSEGEESKVSVGACKHEDISSARSESLDSDSPRYRDGYGVNSAVLETCDSSYVVEPD
QSDMSQDEEDNLTKTLLPPYMFSKLGDMDYSDPPESSCNFGFPEEDHALWSWSY
```

SEQ ID NO 52: Oryza sativa GOS2 promoter

```
AATCCGAAAAGTTTCTGCACCGTTTTCACCCCCTAACTAACAATATAGGGAACGTGTGCTAAATAT
AAAATGAGACCTTATATATGTAGCGCTGATAACTAGAACTATGCAAGAAAAACTCATCCACCTACT
TTAGTGGCAATCGGGCTAAATAAAAAAGAGTCGCTACACTAGTTTCGTTTTCCTTAGTAATTAAGT
GGGAAAATGAAATCATTATTGCTTAGAATATACGTTCACATCTCTGTCATGAAGTTAAATTATTCG
AGGTAGCCATAATTGTCATCAAACTCTTCTTGAATAAAAAAATCTTTCTAGCTGAACTCAATGGGT
AAAGAGAGAGATTTTTTTTAAAAAAATAGAATGAAGATATTCTGAACGTATTGGCAAAGATTTAAA
CATATAATTATATAATTTTATAGTTTGTGCATTCGTCATATCGCACATCATTAAGGACATGTCTTA
CTCCATCCCAATTTTTATTTAGTAATTAAAGACAATTGACTTATTTTTATTATTTATCTTTTTTCG
ATTAGATGCAAGGTACTTACGCACACACTTTGTGCTCATGTGCATGTGTGAGTGCACCTCCTCAAT
ACACGTTCAACTAGCAACACATCTCTAATATCACTCGCCTATTTAATACATTTAGGTAGCAATATC
TGAATTCAAGCACTCCACCATCACCAGACCACTTTTAATAATATCTAAAATACAAAAAATAATTTT
ACAGAATAGCATGAAAAGTATGAAACGAACTATTTAGGTTTTTCACATACAAAAAAAAAAGAATT
TTGCTCGTGCGCGAGCGCCAATCTCCCATATTGGGCACACAGGCAACAACAGAGTGGCTGCCCACA
GAACAACCCACAAAAAACGATGATCTAACGGAGGACAGCAAGTCCGCAACAACCTTTTAACAGCAG
GCTTTGCGGCCAGGAGAGAGGAGGAGAGGCAAAGAAAACCAAGCATCCTCCTTCTCCCATCTATAA
ATTCCTCCCCCCTTTTCCCCTCTCTATATAGGAGGCATCCAAGCCAAGAAGAGGGAGAGCACCAAG
GACACGCGACTAGCAGAAGCCGAGCGACCGCCTTCTCGATCCATATCTTCCGGTCGAGTTCTTGGT
CGATCTCTTCCCTCCTCCACCTCCTCCTCACAGGGTATGTGCCTCCCTTCGGTTGTTCTTGGATTT
ATTGTTCTAGGTTGTGTAGTACGGGCGTTGATGTTAGGAAAGGGGATCTGTATCTGTGATGATTCC
TGTTCTTGGATTTGGGATAGAGGGGTTCTTGATGTTGCATGTTATCGGTTCGGTTTGATTAGTAGT
ATGGTTTTCAATCGTCTGGAGAGCTCTATGGAAATGAAATGGTTTAGGGATCGGAATCTTGCGATT
TTGTGAGTACCTTTTGTTTGAGGTAAAATCAGAGCACCGGTGATTTTGCTTGGTGTAATAAAGTAC
GGTTGTTTGGTCCTCGATTCTGGTAGTGATGCTTCTCGATTTGACGAAGCTATCCTTTGTTTATTC
CCTATTGAACAAAAATAATCCAACTTTGAAGACGGTCCCGTTGATGAGATTGAATGATTGATTCTT
AAGCCTGTCCAAAATTTCGCAGCTGGCTTGTTTAGATACAGTAGTCCCCATCACGAAATTCATGGA
```

FIGURE 4 (continued)

```
AACAGTTATAATCCTCAGGAACAGGGGATTCCCTGTTCTTCCGATTTGCTTTAGTCCCAGAATTTT
TTTTCCCAAATATCTTAAAAAGTCACTTTCTGGTTCAGTTCAATGAATTGATTGCTACAAATAATG
CTTTTATAGCGTTATCCTAGCTGTAGTTCAGTTAATAGGTAATACCCCTATAGTTTAGTCAGGAGA
AGAACTTATCCGATTTCTGATCTCCATTTTTAATTATATGAAATGAACTGTAGCATAAGCAGTATT
CATTTGGATTATTTTTTTATTAGCTCTCACCCCTTCATTATTCTGAGCTGAAAGTCTGGCATGAA
CTGTCCTCAATTTTGTTTTCAAATTCACATCGATTATCTATGCATTATCCTCTTGTATCTACCTGT
AGAAGTTTCTTTTTGGTTATTCCTTGACTGCTTGATTACAGAAAGAAATTTATGAAGCTGTAATCG
GGATAGTTATACTGCTTGTTCTTATGATTCATTTCCTTTGTGCAGTTCTTGGTGTAGCTTGCCACT
TTCACCAGCAAAGTTC
```

FIGURE 4 (continued)

```
                        SEQUENCE LISTING

<160> NUMBER OF SEQ ID NOS: 57

<210> SEQ ID NO 1
<211> LENGTH: 1050
<212> TYPE: DNA
<213> ORGANISM: Oryza sativa

<400> SEQUENCE: 1
atggatcccg gccgcgtcgt gttcgactcc ggcgtggcgc ggcgggcgtg ccccggcggc      60
gcgcagatgc ttctcttcgg cggcggcggc agcgccaaca gcgcgcggctt cttccgaggc     120 gtgccggcgg cggtgctggg gatggatgaa tcgcggtcgt cgtcgtcggc ggcggggggcg     180 ggggcgaagc ggccgttctt cacgacgcac gaggagctcc tggaggagga gtactacgac     240
gagcaggcgc cggagaagaa gcggcggctg acggcggagc aggtgcagat gctggagcgg     300
agcttcgagg aggagaacaa gctggagccg gagcggaaga cggagctcgc ccgccgcctc     360
ggcatggccc cccggcaggt cgccgtctgg ttccagaacc gccgcgcccg ctggaagacc     420
aagcagctcg agcacgactt cgaccgcctc aaggccgcct acgacgccct cgccgccgac     480
caccatgccc tcctctccga caacgaccgc ctccgcgcgc aggtaatctc attaaccgag     540
aagctgcaag acaaggagac gtcgccgtcg tcggcgacca tcaccaccgc ggcgcaggag     600
gtcgaccagc cggacgaaca cacggaggcc gcgtcaacca ccggcttcgc caccgtcgac     660
ggcgcattgg cggcgccacc gcccggccac cagcagccgc cgcataaaga tgatcttgtg     720
agcagcggcg gcaccaacga cgacggcgat ggcggcgcgg ccgtggtggt cttcgacgtc     780
accgagggcg ccaacgaccg cctcagctgc gagtcggcgt acttcgccga cgccgcggag     840
gcgtacgagc gcgactgcgc cggcactac gccctctcgt cggaggagga ggacggcggc     900
gcggtcagcg acgagggctg cagcttcgac ctccccgacg ccgccgccgc cgccgccgcc     960
atgttcggcg ccgccggagt tgtgcaccac gacgccgcgg acgacgagga ggcgcagctc    1020
ggcagctgga ccgcctggtt ctggagctga                                      1050
```

```
<210> SEQ ID NO 2
<211> LENGTH: 349
<212> TYPE: PRT
<213> ORGANISM: Oryza sativa

<400> SEQUENCE: 2

Met Asp Pro Gly Arg Val Val Phe Asp Ser Gly Val Ala Arg Arg Ala
 1               5                  10                  15

Cys Pro Gly Gly Ala Gln Met Leu Leu Phe Gly Gly Gly Gly Ser Ala
             20                  25                  30

Asn Ser Gly Gly Phe Phe Arg Gly Val Pro Ala Ala Val Leu Gly Met
         35                  40                  45

Asp Glu Ser Arg Ser Ser Ser Ala Ala Gly Ala Gly Ala Lys Arg
     50                  55                  60

Pro Phe Phe Thr Thr His Glu Glu Leu Leu Glu Glu Tyr Tyr Asp
 65                  70                  75                  80

Glu Gln Ala Pro Glu Lys Lys Arg Arg Leu Thr Ala Glu Gln Val Gln
                 85                  90                  95

Met Leu Glu Arg Ser Phe Glu Glu Glu Asn Lys Leu Glu Pro Glu Arg
            100                 105                 110

Lys Thr Glu Leu Ala Arg Arg Leu Gly Met Ala Pro Arg Gln Val Ala
            115                 120                 125

Val Trp Phe Gln Asn Arg Arg Ala Arg Trp Lys Thr Lys Gln Leu Glu
130                 135                 140

His Asp Phe Asp Arg Leu Lys Ala Ala Tyr Asp Ala Leu Ala Ala Asp
145                 150                 155                 160

His His Ala Leu Leu Ser Asp Asn Asp Arg Leu Arg Ala Gln Val Ile
                165                 170                 175

Ser Leu Thr Glu Lys Leu Gln Asp Lys Glu Thr Ser Pro Ser Ser Ala
            180                 185                 190

Thr Ile Thr Thr Ala Ala Gln Glu Val Asp Gln Pro Asp Glu His Thr
            195                 200                 205

Glu Ala Ala Ser Thr Thr Gly Phe Ala Thr Val Asp Gly Ala Leu Ala
    210                 215                 220

Ala Pro Pro Gly His Gln Gln Pro Pro His Lys Asp Asp Leu Val
225                 230                 235                 240

Ser Ser Gly Gly Thr Asn Asp Asp Gly Asp Gly Ala Ala Val Val
                245                 250                 255

Val Phe Asp Val Thr Glu Gly Ala Asn Asp Arg Leu Ser Cys Glu Ser
            260                 265                 270

Ala Tyr Phe Ala Asp Ala Ala Glu Ala Tyr Glu Arg Asp Cys Ala Gly
            275                 280                 285

His Tyr Ala Leu Ser Ser Glu Glu Glu Asp Gly Gly Ala Val Ser Asp
    290                 295                 300

Glu Gly Cys Ser Phe Asp Leu Pro Asp Ala Ala Ala Ala Ala Ala
305                 310                 315                 320

Met Phe Gly Ala Ala Gly Val Val His His Asp Ala Ala Asp Asp Glu
                325                 330                 335

Glu Ala Gln Leu Gly Ser Trp Thr Ala Trp Phe Trp Ser
            340                 345

<210> SEQ ID NO 3
<211> LENGTH: 1197
<212> TYPE: DNA
<213> ORGANISM: Oryza sativa
```

<400> SEQUENCE: 3

```
atggagtccg gccggctcat cttcagcacg gcgggctccg gcgccgggca gatgctcttc      60
ttggactgcg gcgctggcgg cggcggcgtc ggcggcgggg ccatgttcca tcgaggggcg     120
agaccggtgc tcggcatgga ggaaggaggg cgcggcgtca gcggcccctt cttcaccacc     180
cccgacgagc tcctcgaaga ggagtactac gacgagcagc tcccggagaa gaagcggcgc     240
ctcacgccgg agcaggtgca tctgctggag aggagcttcg aggaggagaa caagctggag     300
ccggagcgga agacggagct ggcgcggaag ctagggctgc agccgcggca ggtcgccgtg     360
tggttccaga accgccgcgc gcgctggaag accaagcagc tcgagcgcga cttcgaccgc     420
ctcaaggcgt cgttcgacgc cctccgcgcc gaccacgacg ccctcctcca ggacaaccac     480
cgcctccact ctcaggtcat gtcgttgacc gagaagctgc aagagaagga gacgacgacc     540
gagggcagcg ccggcgcggc cgttgacgtc ccgggcttgc ctgcggcggc cgacgtgaag     600
gtcgccgtcc cggacgccga ggaaccggcg ctggaggagg cggcggcggc gttcgaggag     660
cagcaggagc agcaggtgaa ggccgaggac aggctgagca cgggcagcgg cgggagcgcg     720
gtggtggaca cggacgcgca actggtggtc ggtgcggcc ggcaagcatc tcgccgccgt     780
ggacagcagc gtggagtcgt acttcccggg cggcgacgag taccacgact gcgtgatggg     840
ccccatggac cacgccgcgg ggggcatcca gtcggaggag gacgacgcg ccggcagcga     900
cgagggctgc agctactacg ccgacgacgc cggcgtcctc ttcgccgacc acggccacca     960
ccaccaccac caacacgcgg acgacgacga ggaggacggc cagcagatca gctgctggtg    1020
gatgtggaac tagatttctc gcgcgcgcgc gtcgtcgtgc attcaattct cgtgttaaaa    1080
aaatcgttct ctttttcatt tttccgcttc tttgtctgta atgttgagtt tcgatcggct    1140
atgagaagga aggaggtgta tgcatgtgca tggtatggta gggtaacaca tcggtga      1197
```

<210> SEQ ID NO 4
<211> LENGTH: 343
<212> TYPE: PRT
<213> ORGANISM: Oryza sativa

<400> SEQUENCE: 4

```
Met Glu Ser Gly Arg Leu Ile Phe Ser Thr Ala Gly Ser Gly Ala Gly
1               5                   10                  15

Gln Met Leu Phe Leu Asp Cys Gly Ala Gly Gly Gly Val Gly Gly
            20                  25                  30

Gly Ala Met Phe His Arg Gly Ala Arg Pro Val Leu Gly Met Glu Glu
        35                  40                  45

Gly Gly Arg Gly Val Lys Arg Pro Phe Phe Thr Thr Pro Asp Glu Leu
    50                  55                  60

Leu Glu Glu Glu Tyr Tyr Asp Glu Gln Leu Pro Glu Lys Lys Arg Arg
65                  70                  75                  80

Leu Thr Pro Glu Gln Val His Leu Leu Glu Arg Ser Phe Glu Glu Glu
                85                  90                  95

Asn Lys Leu Glu Pro Glu Arg Lys Thr Glu Leu Ala Arg Lys Leu Gly
            100                 105                 110

Leu Gln Pro Arg Gln Val Ala Val Trp Phe Gln Asn Arg Arg Ala Arg
        115                 120                 125

Trp Lys Thr Lys Gln Leu Glu Arg Asp Phe Asp Arg Leu Lys Ala Ser
    130                 135                 140

Phe Asp Ala Leu Arg Ala Asp His Asp Ala Leu Leu Gln Asp Asn His
145                 150                 155                 160
```

```
Arg Leu His Ser Gln Val Met Ser Leu Thr Glu Lys Leu Gln Glu Lys
                165                 170                 175

Glu Thr Thr Thr Glu Gly Ser Ala Gly Ala Ala Val Asp Val Pro Gly
            180                 185                 190

Leu Pro Ala Ala Ala Asp Val Lys Val Ala Val Pro Asp Ala Glu Glu
        195                 200                 205

Pro Ala Leu Glu Glu Ala Ala Ala Phe Glu Glu Gln Gln Glu Gln
    210                 215                 220

Gln Val Lys Ala Glu Asp Arg Leu Ser Thr Gly Ser Gly Gly Ser Ala
225                 230                 235                 240

Val Val Asp Thr Asp Ala Gln Leu Val Val Gly Cys Gly Arg Gln His
                245                 250                 255

Leu Ala Ala Val Asp Ser Ser Val Glu Ser Tyr Phe Pro Gly Gly Asp
            260                 265                 270

Glu Tyr His Asp Cys Val Met Gly Pro Met Asp His Ala Ala Gly Gly
        275                 280                 285

Ile Gln Ser Glu Glu Asp Asp Gly Ala Gly Ser Asp Glu Gly Cys Ser
    290                 295                 300

Tyr Tyr Ala Asp Asp Ala Gly Val Leu Phe Ala Asp His Gly His His
305                 310                 315                 320

His His His Gln His Ala Asp Asp Asp Glu Glu Asp Gly Gln Gln Ile
                325                 330                 335

Ser Cys Trp Trp Met Trp Asn
            340

<210> SEQ ID NO 5
<211> LENGTH: 819
<212> TYPE: DNA
<213> ORGANISM: Zea mays

<400> SEQUENCE: 5
atggatccga gcgcggtcag tttcgactct ggcggcgcgc ggcggggcgg cggcgcgcag      60
atgctgctct cggcggcgg aggcagcgcc aacagcaacg gcttcttccg aggtgttccg      120
atggcggtcc tgggcatgga cgacgcgacg cgcgtgggca gcggcccctt cttcacgaca      180
cacgaggagc tcctagagga ggagtactac gacgagcagg cgccggagaa gaagcgccga      240
ctgacggcgg agcaggtgca gctgctggag cggagcttcg aagaagagaa caagctggag      300
ccggagcgca agaccgagct ggctcgccgc ctggggatgg cgccccgcca ggtagctgtt      360
tggttccaga accgccgcgc gcgctggaag accaagcaac tcgagaccga ctatgaccgc      420
ctcaaggctg cttacgacgc actcgccgcc gaccaccagg gcctcctggc cgacaacgat      480
aacctccggg cacaggtgat ctccctgacg gagaagctgc aaggcaagga gacatccccg      540
tcggcaacca ctgctgccca gaggtcgac cagccagacg aacacaccgc tgtgtcaggc      600
acggaagaac tgctggcgca gcagctcaag gacaacctcc acagcagcgg cgactgcact      660
ggccatggca ccctctcttc ggaagaagac gacggtggcg tggtcagtga cgagggctgc      720
agcttcgctc tcccggatgc catgttcgct gccgggttca cccaccatgg cgccgaggag      780
gtgcagctgg ccaactggac atccatgttc tggaactga                            819

<210> SEQ ID NO 6
<211> LENGTH: 272
<212> TYPE: PRT
<213> ORGANISM: Zea mays

<400> SEQUENCE: 6
```

```
Met Asp Pro Ser Ala Val Ser Phe Asp Ser Gly Gly Ala Arg Arg Gly
1               5                   10                  15

Gly Gly Ala Gln Met Leu Leu Phe Gly Gly Gly Ser Ala Asn Ser
            20                  25                  30

Asn Gly Phe Phe Arg Gly Val Pro Met Ala Val Leu Gly Met Asp Asp
                35                  40                  45

Ala Thr Arg Val Gly Lys Arg Pro Phe Phe Thr Thr His Glu Glu Leu
    50                  55                  60

Leu Glu Glu Glu Tyr Tyr Asp Glu Gln Ala Pro Glu Lys Lys Arg Arg
65              70                  75                  80

Leu Thr Ala Glu Gln Val Gln Leu Leu Glu Arg Ser Phe Glu Glu Glu
                85                  90                  95

Asn Lys Leu Glu Pro Glu Arg Lys Thr Glu Leu Ala Arg Arg Leu Gly
                100                 105                 110

Met Ala Pro Arg Gln Val Ala Val Trp Phe Gln Asn Arg Arg Ala Arg
            115                 120                 125

Trp Lys Thr Lys Gln Leu Glu Thr Asp Tyr Asp Arg Leu Lys Ala Ala
    130                 135                 140

Tyr Asp Ala Leu Ala Ala Asp His Gln Gly Leu Leu Asp Asn Asp
145                 150                 155                 160

Asn Leu Arg Ala Gln Val Ile Ser Leu Thr Glu Lys Leu Gln Gly Lys
                165                 170                 175

Glu Thr Ser Pro Ser Ala Thr Ala Ala Gln Glu Val Asp Gln Pro
                180                 185                 190

Asp Glu His Thr Ala Val Ser Gly Thr Glu Glu Leu Leu Ala Gln Gln
            195                 200                 205

Leu Lys Asp Asn Leu His Ser Ser Gly Asp Cys Thr Gly His Gly Thr
    210                 215                 220

Leu Ser Ser Glu Glu Asp Asp Gly Gly Val Val Ser Asp Glu Gly Cys
225                 230                 235                 240

Ser Phe Ala Leu Pro Asp Ala Met Phe Ala Ala Gly Phe Thr His His
                245                 250                 255

Gly Ala Glu Glu Val Gln Leu Ala Asn Trp Thr Ser Met Phe Trp Asn
            260                 265                 270
```

<210> SEQ ID NO 7
<211> LENGTH: 993
<212> TYPE: DNA
<213> ORGANISM: Zea mays

<400> SEQUENCE: 7

```
atggagtctg  acggctcat  cttcaacgcg  ccgggctctg  cgccgggca   gatgctcttc      60
ctcgactgcg  gcgcaggcgg  cggtcccggc  ggcggcttgt  tccatcgagg  cgggagaccg    120
atgcttggcc  ttgaagaagg  gcgcggcgta  aaacggccct  tcttcacctc  gcccgacgag    180
ctcctcgagg  aagagtacta  cgacgagcag  ctgccggaga  gaagcgccg   cctcaccccca   240
gagcaggtgc  ttctgctgga  gaggagcttc  gaggaggaga  acaagctgga  gccggagcgc    300
aagacggagc  tggcgcgcaa  gctgggcctg  cagcctcgcc  aggtggccgt  ctggttccag    360
aaccgccgcg  cccggtggaa  gaccaagcag  ctcgagcgcg  acttcgaccg  cctcaaggcc    420
tccttcgacg  ctctccgagc  ggaccacgac  gccctcctcc  aggacaacaa  ccgcctccgc    480
tcacaggttg  tgtcgttgac  cgagaagctg  caagagaagg  aggatgcgac  ggagggcggc    540
gccaccgctg  acaccgccgc  gccggcggtg  gacgtcgagg  cttccctggc  cgacgacgtc    600
gaggagccag  cagagcctgc  ggcgacgttc  gaggtgctgc  aggaggtgaa  gtccgaggac    660
```

```
aggctgagca ccggcagcgg cgggagcgcg gtggtggacg cggacgcgct gctgtacggc    720
aggttcgccg cggcagttga tagcagcgtg gagtcgtact tccccggcgg cgaggaccac    780
taccacgact gcgggacgat gggccccgtg aatcatggcg ccggaggagg catccagtcg    840
gacgacgacg gcgccggcag cgacgagggg tgcagctact acgccgacga agccgccgcc    900
gccgccgccg cgttcttcgc cggacacgcc acccaccacc acgcggacga ggacgaggac    960
gccggccaga tcagctggtg gatgtggaac tag                                 993
```

<210> SEQ ID NO 8
<211> LENGTH: 330
<212> TYPE: PRT
<213> ORGANISM: Zea mays

<400> SEQUENCE: 8

```
Met Glu Ser Gly Arg Leu Ile Phe Asn Ala Pro Gly Ser Gly Ala Gly
1               5                   10                  15

Gln Met Leu Phe Leu Asp Cys Gly Ala Gly Gly Gly Pro Gly Gly Gly
            20                  25                  30

Leu Phe His Arg Gly Gly Arg Pro Met Leu Gly Leu Glu Glu Gly Arg
        35                  40                  45

Gly Val Lys Arg Pro Phe Phe Thr Ser Pro Asp Glu Leu Leu Glu Glu
    50                  55                  60

Glu Tyr Tyr Asp Glu Gln Leu Pro Glu Lys Lys Arg Arg Leu Thr Pro
65                  70                  75                  80

Glu Gln Val Leu Leu Leu Glu Arg Ser Phe Glu Glu Asn Lys Leu
                85                  90                  95

Glu Pro Glu Arg Lys Thr Glu Leu Ala Arg Lys Leu Gly Leu Gln Pro
            100                 105                 110

Arg Gln Val Ala Val Trp Phe Gln Asn Arg Arg Ala Arg Trp Lys Thr
        115                 120                 125

Lys Gln Leu Glu Arg Asp Phe Asp Arg Leu Lys Ala Ser Phe Asp Ala
    130                 135                 140

Leu Arg Ala Asp His Asp Ala Leu Leu Gln Asp Asn Asn Arg Leu Arg
145                 150                 155                 160

Ser Gln Val Val Ser Leu Thr Glu Lys Leu Gln Glu Lys Glu Asp Ala
                165                 170                 175

Thr Glu Gly Gly Ala Thr Ala Asp Thr Ala Ala Pro Ala Val Asp Val
            180                 185                 190

Glu Ala Ser Leu Ala Asp Asp Val Glu Glu Pro Ala Glu Pro Ala Ala
        195                 200                 205

Thr Phe Glu Val Leu Gln Glu Val Lys Ser Glu Asp Arg Leu Ser Thr
    210                 215                 220

Gly Ser Gly Gly Ser Ala Val Val Asp Ala Asp Ala Leu Leu Tyr Gly
225                 230                 235                 240

Arg Phe Ala Ala Ala Val Asp Ser Ser Val Glu Ser Tyr Phe Pro Gly
                245                 250                 255

Gly Glu Asp His Tyr His Asp Cys Gly Thr Met Gly Pro Val Asn His
            260                 265                 270

Gly Ala Gly Gly Gly Ile Gln Ser Asp Asp Asp Gly Ala Gly Ser Asp
        275                 280                 285

Glu Gly Cys Ser Tyr Tyr Ala Asp Glu Ala Ala Ala Ala Ala Ala Ala
    290                 295                 300

Phe Phe Ala Gly His Ala Thr His His His Ala Asp Glu Asp Glu Asp
305                 310                 315                 320
```

```
Ala Gly Gln Ile Ser Trp Trp Met Trp Asn
                325             330
```

<210> SEQ ID NO 9
<211> LENGTH: 825
<212> TYPE: DNA
<213> ORGANISM: Saccharum officinarum

<400> SEQUENCE: 9

```
atggatccga gcgcggtcag tttcaactcc ggcggcgcgc ggcggggcgg cggcggcacg    60
cagatgctgc tcttcggcgg cggaggcagc gccaacagca acggcttctt ccgaggtgtt   120
ccgatggcgg tcctgggcat ggacgacgcg acgcgcgtgg gcaagcggcc cttcttcacc   180
acacacgagg agctcctgga ggaggagtac tacgacgagc aggcgcccga gaagaagcgc   240
cgtctgacgg cggagcaggt gcagctgctg agcggagct  tcgaggaaga gaacaagctg   300
gagcccgagc gcaagaccga gctggctcgc gcctcggga  tggcgccccg ccaggtggcc   360
gtctggttcc agaaccgccg cgcgcgctgg aagaccaagc agctcgagac cgactatgac   420
cacctcaagg ctgcctacga cgcgctcgcc gccgaccacc agggcctcct ggccgacaac   480
gatagcctcc gggcacaggt ggtctcccta acagagaagc tgcaaggcaa ggagacatcc   540
ccgtcggcca ccactgctgc caagaggtc  gaccagccag acgaacacac cgcggcgtca   600
ggcactgaga aactgctggc gcagcagctc aaggacgacc tccacagcag cggcgactgc   660
actggccatg gtgccctctc ctcagaggaa gaagatggtg gtgtggtcag tgacgagggc   720
agctttgatc tcccggatgc catgtttgct gccggggtca cccaccatgg cgccgacgcc   780
gaggaggcac agctggccaa ctggacatcc tggttctgga actga              825
```

<210> SEQ ID NO 10
<211> LENGTH: 274
<212> TYPE: PRT
<213> ORGANISM: Saccharum officinarum

<400> SEQUENCE: 10

```
Met Asp Pro Ser Ala Val Ser Phe Asn Ser Gly Gly Ala Arg Arg Gly
 1               5                  10                  15

Gly Gly Gly Thr Gln Met Leu Leu Phe Gly Gly Gly Gly Ser Ala Asn
            20                  25                  30

Ser Asn Gly Phe Phe Arg Gly Val Pro Met Ala Val Leu Gly Met Asp
        35                  40                  45

Asp Ala Thr Arg Val Gly Lys Arg Pro Phe Phe Thr Thr His Glu Glu
    50                  55                  60

Leu Leu Glu Glu Glu Tyr Tyr Asp Glu Gln Ala Pro Glu Lys Lys Arg
65                  70                  75                  80

Arg Leu Thr Ala Glu Gln Val Gln Leu Leu Glu Arg Ser Phe Glu Glu
                85                  90                  95

Glu Asn Lys Leu Glu Pro Glu Arg Lys Thr Glu Leu Ala Arg Arg Leu
            100                 105                 110

Gly Met Ala Pro Arg Gln Val Ala Val Trp Phe Gln Asn Arg Arg Ala
        115                 120                 125

Arg Trp Lys Thr Lys Gln Leu Glu Thr Asp Tyr Asp His Leu Lys Ala
    130                 135                 140

Ala Tyr Asp Ala Leu Ala Ala Asp His Gln Gly Leu Leu Ala Asp Asn
145                 150                 155                 160

Asp Ser Leu Arg Ala Gln Val Val Ser Leu Thr Glu Lys Leu Gln Gly
                165                 170                 175
```

```
Lys Glu Thr Ser Pro Ser Ala Thr Ala Ala Gln Glu Val Asp Gln
                180                 185                 190

Pro Asp Glu His Thr Ala Ala Ser Gly Thr Glu Lys Leu Leu Ala Gln
        195                 200                 205

Gln Leu Lys Asp Asp Leu His Ser Ser Gly Asp Cys Thr Gly His Gly
    210                 215                 220

Ala Leu Ser Ser Glu Glu Asp Gly Gly Val Val Ser Asp Glu Gly
225                 230                 235                 240

Ser Phe Asp Leu Pro Asp Ala Met Phe Ala Ala Gly Val Thr His His
                245                 250                 255

Gly Ala Asp Ala Glu Glu Ala Gln Leu Ala Asn Trp Thr Ser Trp Phe
        260                 265                 270

Trp Asn

<210> SEQ ID NO 11
<211> LENGTH: 828
<212> TYPE: DNA
<213> ORGANISM: Sorghum bicolor

<400> SEQUENCE: 11
atggatccga gcgcggtcag tttcgactcc ggcggcgcgc ggcggggcgg cggcggcggc      60
ggcgcgcaga tgctgctctt cggcggcgga ggcagcgcca acagcaacgg cttcttccga     120
ggtgttccga tggcggtcct gggcatggac gacgcgacgc gcgtgggcaa gcggcctttc     180
ttcaccacgc acgaggagct cctggaggag gagtactacg acgagcaggc gcccgagaag     240
aagcgccgtc tgacggcgga gcaggtgcag ctgctggagc ggagcttcga ggaagagaac     300
aagctggagc ggagcgcaa gaccgagctg gctcgccgcc tcgggatggc gcctcgccag     360
gtggccgtct ggttccagaa ccgccgcgcg cgctggaaga ctaagcagct cgagaccgac     420
tatgaccgcc tcaaggctgc ctacgacgcg ctcgccgccg accaccaggg cctcctggcc     480
gacaacgata gcctccgggc acaggtgatc tccctaacgg ataagctgca acgcaaggag     540
acatccccgt cggcgaccac tgctgcccaa gaggtcgacc agccagacga acacaccgct     600
gcgtcaggca ctgagaaact gctggtgcag cagctcaagg acgacctcca cagcagcggc     660
gacttcactg ccatggtgc cctctcttca gaggaagagg atggtggtgt ggtcagcgac     720
gagggctgca gctttgatct cccggatgcc atgttcgctg ccggggtcac ccaccatggc     780
gccgaggagg cgcagctggc caactggaca tcctggttct ggaactga                 828

<210> SEQ ID NO 12
<211> LENGTH: 275
<212> TYPE: PRT
<213> ORGANISM: Sorghum bicolor

<400> SEQUENCE: 12

Met Asp Pro Ser Ala Val Ser Phe Asp Ser Gly Gly Ala Arg Arg Gly
1               5                   10                  15

Gly Gly Gly Gly Ala Gln Met Leu Leu Phe Gly Gly Gly Ser
            20                  25                  30

Ala Asn Ser Asn Gly Phe Phe Arg Gly Val Pro Met Ala Val Leu Gly
            35                  40                  45

Met Asp Asp Ala Thr Arg Val Gly Lys Arg Pro Phe Phe Thr Thr His
    50                  55                  60

Glu Glu Leu Leu Glu Glu Glu Tyr Tyr Asp Glu Gln Ala Pro Glu Lys
65                  70                  75                  80
```

```
Lys Arg Arg Leu Thr Ala Glu Gln Val Gln Leu Glu Arg Ser Phe
                85                  90                  95
Glu Glu Glu Asn Lys Leu Glu Pro Glu Arg Lys Thr Glu Leu Ala Arg
            100                 105                 110
Arg Leu Gly Met Ala Pro Arg Gln Val Ala Val Trp Phe Gln Asn Arg
        115                 120                 125
Arg Ala Arg Trp Lys Thr Lys Gln Leu Glu Thr Asp Tyr Asp Arg Leu
    130                 135                 140
Lys Ala Ala Tyr Asp Ala Leu Ala Ala Asp His Gln Gly Leu Leu Ala
145                 150                 155                 160
Asp Asn Asp Ser Leu Arg Ala Gln Val Ile Ser Leu Thr Asp Lys Leu
                165                 170                 175
Gln Arg Lys Glu Thr Ser Pro Ser Ala Thr Thr Ala Ala Gln Glu Val
            180                 185                 190
Asp Gln Pro Asp Glu His Thr Ala Ala Ser Gly Thr Glu Lys Leu Leu
        195                 200                 205
Val Gln Gln Leu Lys Asp Asp Leu His Ser Ser Gly Asp Phe Thr Gly
    210                 215                 220
His Gly Ala Leu Ser Ser Glu Glu Glu Asp Gly Gly Val Val Ser Asp
225                 230                 235                 240
Glu Gly Cys Ser Phe Asp Leu Pro Asp Ala Met Phe Ala Ala Gly Val
                245                 250                 255
Thr His His Gly Ala Glu Glu Ala Gln Leu Ala Asn Trp Thr Ser Trp
            260                 265                 270
Phe Trp Asn
        275

<210> SEQ ID NO 13
<211> LENGTH: 1023
<212> TYPE: DNA
<213> ORGANISM: Triticum aestivum

<400> SEQUENCE: 13
atggagcccg gccggctcat cttcaacacg tcgggctccg gcaacggaca gatgctcttc        60
atggactgcg gcgcgggcgg catcgccggc gcggccggca tgttccatcg aggggtgaga       120
ccggtcctcg gcggcatgga agaagggcgc ggcgtgaagc ggcccttctt cacctcgccg       180
gatgacatgc tcgaggagga gtactacgac gagcagctcc ggagaagaa gcggcgcctc        240
accccggagc aggtccacct gctggagagg agcttcgagg aggagaacaa gctggagccg       300
gagaggaaga cggagctggc ccgcaagctc gggctgcagc acgccaggt ggccgtctgg        360
ttccagaacc gccgcgcccg gtggaagaca aagacgctgg agcgcgactt cgaccgcctc       420
aaggcgtcct tcgacgccct ccgggccgac cacgacgccc cctccaggga caaccaccgg       480
ctccggtcac aggtggtaac gttgaccgag aagatgcaag ataaggaggc gccgaaggc       540
agcttcggtg cagccgccga cgcctcggag ccggagcagg cggcggcgga ggcgaaggct       600
tccttggccg acgccgagga gcaggccgcg cagcggagg cgttcgaggt ggtgcagcag        660
cagctgcacg tgaaggacga ggagaggctg agcccgggga cggcgggag cgcggtgctg       720
gacgcgaggg acgcgctgct cgggagcgga tgcggcctcg ccggcgtggt ggacagcagc       780
gtggactcgt actgcttccc gggggcgcc ggcggcgacg agtaccacga gtgcgtggtg        840
ggccccgtgg cgggcggcat ccagtcggag gaggacgacg gcgcgggcag cgacgagggc       900
tgcagctact acccccgacga cgccgccgtc ttcttcgccg ccgcgcaagg gcacggccac       960
catcgcacgg acgacgacga tcagcaggac gacggccaga tcagctactg gatgtggaac      1020
``` tag                                                                1023

<210> SEQ ID NO 14
<211> LENGTH: 340
<212> TYPE: PRT
<213> ORGANISM: Triticum aestivum

<400> SEQUENCE: 14

Met Glu Pro Gly Arg Leu Ile Phe Asn Thr Ser Gly Ser Gly Asn Gly
1               5                   10                  15

Gln Met Leu Phe Met Asp Cys Gly Ala Gly Gly Ile Ala Gly Ala Ala
            20                  25                  30

Gly Met Phe His Arg Gly Val Arg Pro Val Leu Gly Gly Met Glu Glu
        35                  40                  45

Gly Arg Gly Val Lys Arg Pro Phe Phe Thr Ser Pro Asp Asp Met Leu
    50                  55                  60

Glu Glu Glu Tyr Tyr Asp Glu Gln Leu Pro Glu Lys Lys Arg Arg Leu
65                  70                  75                  80

Thr Pro Glu Gln Val His Leu Leu Glu Arg Ser Phe Glu Glu Glu Asn
                85                  90                  95

Lys Leu Glu Pro Glu Arg Lys Thr Glu Leu Ala Arg Lys Leu Gly Leu
            100                 105                 110

Gln Pro Arg Gln Val Ala Val Trp Phe Gln Asn Arg Arg Ala Arg Trp
        115                 120                 125

Lys Thr Lys Thr Leu Glu Arg Asp Phe Asp Arg Leu Lys Ala Ser Phe
    130                 135                 140

Asp Ala Leu Arg Ala Asp His Asp Ala Leu Leu Gln Asp Asn His Arg
145                 150                 155                 160

Leu Arg Ser Gln Val Val Thr Leu Thr Glu Lys Met Gln Asp Lys Glu
                165                 170                 175

Ala Pro Glu Gly Ser Phe Gly Ala Ala Ala Asp Ala Ser Glu Pro Glu
            180                 185                 190

Gln Ala Ala Ala Glu Ala Lys Ala Ser Leu Ala Asp Ala Glu Glu Gln
        195                 200                 205

Ala Ala Ala Ala Glu Ala Phe Glu Val Val Gln Gln Gln Leu His Val
    210                 215                 220

Lys Asp Glu Glu Arg Leu Ser Pro Gly Ser Gly Ser Ala Val Leu
225                 230                 235                 240

Asp Ala Arg Asp Ala Leu Leu Gly Ser Gly Cys Gly Leu Ala Gly Val
                245                 250                 255

Val Asp Ser Ser Val Asp Ser Tyr Cys Phe Pro Gly Gly Ala Gly Gly
            260                 265                 270

Asp Glu Tyr His Glu Cys Val Val Gly Pro Val Ala Gly Gly Ile Gln
        275                 280                 285

Ser Glu Glu Asp Asp Gly Ala Gly Ser Asp Glu Gly Cys Ser Tyr Tyr
    290                 295                 300

Pro Asp Asp Ala Ala Val Phe Phe Ala Ala Gln Gly His Gly His
305                 310                 315                 320

His Arg Thr Asp Asp Asp Gln Gln Asp Asp Gly Gln Ile Ser Tyr
                325                 330                 335

Trp Met Trp Asn
            340

<210> SEQ ID NO 15
<211> LENGTH: 819

```
<212> TYPE: DNA
<213> ORGANISM: Arabidopsis thaliana

<400> SEQUENCE: 15
atggaatcca attcgttttt cttcgatcca tctgcttcac acggcaacag catgttcttc      60
cttgggaatc tcaatcccgt cgtccaagga ggaggagcaa gatcgatgat gaacatggag     120
gaaacttcga agcgaaggcc cttctttagc tcccctgagg atctctacga cgatgacttt     180
tacgacgacc agttgcctga aaagaagcgt cgcctcacta ccgaacaagt gcatctgctg     240
gagaaaagct tcgagacaga gaacaagcta gagcctgaac gcaagactca gcttgccaag     300
aagcttggtc tacagccaag gcaagtggct gtctggtttc agaatcgccg agctcgttgg     360
aaaacaaaac agcttgagag agactacgat cttctcaagt ccacttacga ccaacttctt     420
tctaactacg actccatcgt catggacaac gataagctca gatccgaggt tacttccctg     480
accgaaaagc ttcagggcaa acaagagaca gctaatgaac cacctggtca agtgcccgaa     540
ccaaaccaac ttgatccggt ttacattaat gcggcagcaa tcaaaaccga ggaccggtta     600
agttcaggga gcgttgggag cgcggtacta gacgacgacg cacctcaact actagacagc     660
tgtgactctt acttcccaag catcgtaccc atccaagaca cagcaacgc cagtgatcat      720
gacaatgacc ggagctgttt cgccgacgtc tttgtgccca ccacttcacc gtcgcacgat     780
catcacggtg aatcattggc tttctgggga tggccttag                            819

<210> SEQ ID NO 16
<211> LENGTH: 272
<212> TYPE: PRT
<213> ORGANISM: Arabidopsis thaliana

<400> SEQUENCE: 16

Met Glu Ser Asn Ser Phe Phe Asp Pro Ser Ala Ser His Gly Asn
1               5                   10                  15

Ser Met Phe Phe Leu Gly Asn Leu Asn Pro Val Val Gln Gly Gly
            20                  25                  30

Ala Arg Ser Met Met Asn Met Glu Glu Thr Ser Lys Arg Arg Pro Phe
        35                  40                  45

Phe Ser Ser Pro Glu Asp Leu Tyr Asp Asp Phe Tyr Asp Asp Gln
    50                  55                  60

Leu Pro Glu Lys Lys Arg Arg Leu Thr Thr Glu Gln Val His Leu Leu
65                  70                  75                  80

Glu Lys Ser Phe Glu Thr Glu Asn Lys Leu Glu Pro Glu Arg Lys Thr
                85                  90                  95

Gln Leu Ala Lys Lys Leu Gly Leu Gln Pro Arg Gln Val Ala Val Trp
            100                 105                 110

Phe Gln Asn Arg Arg Ala Arg Trp Lys Thr Lys Gln Leu Glu Arg Asp
        115                 120                 125

Tyr Asp Leu Leu Lys Ser Thr Tyr Asp Gln Leu Ser Asn Tyr Asp
    130                 135                 140

Ser Ile Val Met Asp Asn Asp Lys Leu Arg Ser Glu Val Thr Ser Leu
145                 150                 155                 160

Thr Glu Lys Leu Gln Gly Lys Gln Glu Thr Ala Asn Glu Pro Pro Gly
                165                 170                 175

Gln Val Pro Glu Pro Asn Gln Leu Asp Pro Val Tyr Ile Asn Ala Ala
            180                 185                 190

Ala Ile Lys Thr Glu Asp Arg Leu Ser Ser Gly Ser Val Gly Ser Ala
        195                 200                 205
```

Val Leu Asp Asp Ala Pro Gln Leu Leu Asp Ser Cys Asp Ser Tyr
    210                 215                 220

Phe Pro Ser Ile Val Pro Ile Gln Asp Asn Ser Asn Ala Ser Asp His
225                 230                 235                 240

Asp Asn Asp Arg Ser Cys Phe Ala Asp Val Phe Val Pro Thr Thr Ser
                245                 250                 255

Pro Ser His Asp His His Gly Glu Ser Leu Ala Phe Trp Gly Trp Pro
            260                 265                 270

<210> SEQ ID NO 17
<211> LENGTH: 969
<212> TYPE: DNA
<213> ORGANISM: Daucus carota

<400> SEQUENCE: 17

```
atggcgggtc ggagggtgtt ctatggggag ggagccaata cgacgtcggc tagcctgttg      60
tttcatagtc aaagacctga gcctttcttt ctttctgcac cttctccttc tctaattggt     120
tcaaaatcca tggttagctt tcaagatgct aagcgaaaaa atccctacga tgggttcttt     180
atgcggtcat atgatgaaga agaaattggg gatgaagaat atgatgaata ctttcagcag     240
cctgagaaga gaggaggct caaggctgat caaatccagt ttcttgagaa agttttgag      300
actgataaca gcttgagcc tgaaagaaaa gttcagcttg caaagaact cggcttgcag      360
ccaagacagg ttgcgatatg gtttcagaac cgtcgagcac ggtggaagac caaaacacta     420
gaaaagatt atgatgtatt gcaaaatagc tacaacagcc tcaaggctga ctatgacaat     480
ctacttgccg agaaagaaaa acttaaagcc gaggttctcg acctgacaga caagctactt     540
ctcaaagaag ataaggggag caagacagta gttttgata agcaaaaggt gtctgcagca     600
ttccaacaag aacgtgttag taatgacata tctgtgggtg aagtactcag taactcagtt     660
atggactgca agcaagaaga tcataactct gtgaaaagtg atgcagttga ttctgacagt     720
ccacactaca gtgatgaagt ctactccagt tttatggagc cagtggatcg ctcttatgtt     780
tttgaacctg ctcagtcgga tatatctcaa gatgaagaag atgacatggg gaacaactta     840
tttctcccat catatcatgt tttctcaaag actgaagacg gtagttactc cgaccagcct     900
tcgaactctt cgtactttgg cttcccagtt gaagatcata cgtttggctt ttggggtact     960
gaattataa                                                             969
```

<210> SEQ ID NO 18
<211> LENGTH: 322
<212> TYPE: PRT
<213> ORGANISM: Daucus carota

<400> SEQUENCE: 18

Met Ala Gly Arg Arg Val Phe Tyr Gly Glu Gly Ala Asn Thr Thr Ser
1               5                   10                  15

Ala Ser Leu Leu Phe His Ser Gln Arg Pro Pro Phe Phe Leu Ser
            20                  25                  30

Ala Pro Ser Pro Ser Leu Ile Gly Ser Lys Ser Met Val Ser Phe Gln
        35                  40                  45

Asp Ala Lys Arg Lys Asn Pro Tyr Asp Gly Phe Phe Met Arg Ser Tyr
    50                  55                  60

Asp Glu Glu Glu Ile Gly Asp Glu Glu Tyr Asp Glu Tyr Phe Gln Gln
65                  70                  75                  80

Pro Glu Lys Lys Arg Arg Leu Lys Ala Asp Gln Ile Gln Phe Leu Glu
                85                  90                  95

```
Lys Ser Phe Glu Thr Asp Asn Lys Leu Glu Pro Glu Arg Lys Val Gln
            100                 105                 110
Leu Ala Lys Glu Leu Gly Leu Gln Pro Arg Gln Val Ala Ile Trp Phe
        115                 120                 125
Gln Asn Arg Arg Ala Arg Trp Lys Thr Lys Thr Leu Glu Lys Asp Tyr
    130                 135                 140
Asp Val Leu Gln Asn Ser Tyr Asn Ser Leu Lys Ala Asp Tyr Asp Asn
145                 150                 155                 160
Leu Leu Ala Glu Lys Glu Lys Leu Lys Ala Glu Val Leu Asp Leu Thr
                165                 170                 175
Asp Lys Leu Leu Leu Lys Glu Asp Lys Gly Ser Lys Thr Val Val Phe
            180                 185                 190
Asp Lys Gln Lys Val Ser Ala Ala Phe Gln Gln Glu Arg Val Ser Asn
        195                 200                 205
Asp Ile Ser Val Gly Glu Val Leu Ser Asn Ser Val Met Asp Cys Lys
    210                 215                 220
Gln Glu Asp His Asn Ser Val Lys Ser Asp Ala Val Asp Ser Asp Ser
225                 230                 235                 240
Pro His Tyr Ser Asp Glu Val Tyr Ser Ser Phe Met Glu Pro Val Asp
                245                 250                 255
Arg Ser Tyr Val Phe Glu Pro Ala Gln Ser Asp Ile Ser Gln Asp Glu
            260                 265                 270
Glu Asp Asp Met Gly Asn Asn Leu Phe Leu Pro Ser Tyr His Val Phe
        275                 280                 285
Ser Lys Thr Glu Asp Gly Ser Tyr Ser Asp Gln Pro Ser Asn Ser Ser
    290                 295                 300
Tyr Phe Gly Phe Pro Val Glu Asp His Thr Phe Gly Phe Trp Gly Thr
305                 310                 315                 320
Glu Leu
```

<210> SEQ ID NO 19
<211> LENGTH: 1038
<212> TYPE: DNA
<213> ORGANISM: Glycine max

<400> SEQUENCE: 19

```
atggcgagtg gcaagcttta tgcgggttca aacatgtcac ttctcctcca aaacgaaagg    60
ctcccttgct cctctgaagt ccttgagtct ctttgggctc agacctctaa ccctgcttcc   120
ttccaaggtt caaacccgt ggttgatttt gagaatgtaa gtgggagcag gatgacggat   180
aggccttct ttcaagcgtt ggagaaggaa gagaactgtg atgaggatta cgaggggtgt   240
ttccaccaac cggggaagaa aaggaggctc acaagcgaac aagttcagtt ccttgaaagg   300
aactttgagg tagagaacaa gcttgaaccc gaaaggaaag tccaacttgc aaaagagctt   360
ggcttgcagc caaggcaagt tgctatatgg ttccaaaacc gaagggcaag gttcaagacc   420
aagcagctag aaaaagacta tgacgtgttg aagctagtt atgacagact caaaagtgac   480
tatgaaagtc ttgttcaaga gaatgacaag ttaaaagcag aggtgaattc tctggagagc   540
aaattgattc ttagagataa agagaaggag gagaattcgg atgacaagtc atctcctgat   600
gatgctgtca attcttcttc accccacaac aacaaggagc ctatggattt attaattat    660
tcaaaaaatg caacaacaac aacaacatct gaaaatggga ccaaagtgtt gtcaccactc   720
ccactcccta ttatggtaac atgctgcaag caagaagatg ccaactcagc caaaagtgat   780
gtccttgatt cggatagccc acattgcact tcattcgtgg agcctgctga ttcctctcat   840
```

-continued

```
gcctttgaac cagaagacca ctcagaagac ttctcccaag atgaagagga taaccttagt    900
gaaaaccttt tgatgacctt cccttcttct tgttgcttac ctaaggttga agaacactgc    960
tatgacggcc ctcctgaaaa ctcttgtaat tttggcttcc aggttgagga tcaaaccttc   1020
tgtttctggc cctattga                                                 1038
```

<210> SEQ ID NO 20
<211> LENGTH: 345
<212> TYPE: PRT
<213> ORGANISM: Glycine max

<400> SEQUENCE: 20

```
Met Ala Ser Gly Lys Leu Tyr Ala Gly Ser Asn Met Ser Leu Leu Leu
1               5                   10                  15

Gln Asn Glu Arg Leu Pro Cys Ser Ser Glu Val Leu Glu Ser Leu Trp
            20                  25                  30

Ala Gln Thr Ser Asn Pro Ala Ser Phe Gln Gly Ser Lys Pro Val Val
        35                  40                  45

Asp Phe Glu Asn Val Ser Gly Ser Arg Met Thr Asp Arg Pro Phe Phe
    50                  55                  60

Gln Ala Leu Glu Lys Glu Asn Cys Asp Glu Asp Tyr Glu Gly Cys
65                  70                  75                  80

Phe His Gln Pro Gly Lys Lys Arg Arg Leu Thr Ser Glu Gln Val Gln
                85                  90                  95

Phe Leu Glu Arg Asn Phe Glu Val Glu Asn Lys Leu Glu Pro Glu Arg
            100                 105                 110

Lys Val Gln Leu Ala Lys Glu Leu Gly Leu Gln Pro Arg Gln Val Ala
        115                 120                 125

Ile Trp Phe Gln Asn Arg Arg Ala Arg Phe Lys Thr Lys Gln Leu Glu
    130                 135                 140

Lys Asp Tyr Gly Val Leu Lys Ala Ser Tyr Asp Arg Leu Lys Ser Asp
145                 150                 155                 160

Tyr Glu Ser Leu Val Gln Glu Asn Asp Lys Leu Lys Ala Glu Val Asn
                165                 170                 175

Ser Leu Glu Ser Lys Leu Ile Leu Arg Asp Lys Glu Lys Glu Asn
            180                 185                 190

Ser Asp Asp Lys Ser Ser Pro Asp Asp Ala Val Asn Ser Ser Ser Pro
        195                 200                 205

His Asn Asn Lys Glu Pro Met Asp Leu Leu Ile Ile Ser Lys Asn Ala
    210                 215                 220

Thr Thr Thr Thr Thr Ser Glu Asn Gly Thr Lys Val Leu Ser Pro Leu
225                 230                 235                 240

Pro Leu Pro Ile Met Val Thr Cys Cys Lys Gln Glu Asp Ala Asn Ser
                245                 250                 255

Ala Lys Ser Asp Val Leu Asp Ser Asp Ser Pro His Cys Thr Ser Phe
            260                 265                 270

Val Glu Pro Ala Asp Ser Ser His Ala Phe Glu Pro Glu Asp His Ser
        275                 280                 285

Glu Asp Phe Ser Gln Asp Glu Asp Asn Leu Ser Glu Asn Leu Leu
    290                 295                 300

Met Thr Phe Pro Ser Ser Cys Cys Leu Pro Lys Val Glu Glu His Cys
305                 310                 315                 320

Tyr Asp Gly Pro Pro Glu Asn Ser Cys Asn Phe Gly Phe Gln Val Glu
                325                 330                 335

Asp Gln Thr Phe Cys Phe Trp Pro Tyr
            340                 345
```

<210> SEQ ID NO 21
<211> LENGTH: 858
<212> TYPE: DNA
<213> ORGANISM: Craterostigma plantagineum

<400> SEQUENCE: 21

```
atgaactctg ctcggatttt cttcgaccca tcttcccacg caacatgct gcagtttctt      60
gggaacgccg gcggcgattc atccgttttc gaggaacaa gatcgtcgtc ggtgctgaac     120
atggaggaga gctcgttaaa acgacagatt ttcagcggcg gcggcggcga tgaattctac    180
gacgaggaat actacgacga gcagttgttg cctgagaaga agcgccgact caccgccgag    240
caggttcact tgcttgagaa gagcttcgag gctgagaaca agcttgagcc tgagcgaaag    300
gctgagctgg cgaagaagct cggattgcag ccgaggcaag tcgccatttg gttccaaaac    360
cgccgagcac ggtggaagac taagcagtta gagagggact acgacaagct taagtcttcc    420
tatgattctc ttctctcaac ctacgactct attcgccagg aaaacgacaa gctcaaagcc    480
gagctccttt ccctgaacga gaaattgcaa cccaaagacg acgacgaccc atcggccgaa    540
ataggtcgaa atctcagttc atcgtcgccg cctgtcgacg cggctgagcc gccgtgcctg    600
aagctgacgg tgaaggtgga ggaccgcctg agcacgggga gcaacggcag cgcagtaatg    660
gacggcgacg gacctcagca gctcctcgac gacagcggcg actcgtactt cgagaacgac    720
gaggaatacg actgcgccgc cgcaagtttg gctgctgcga aggaggacga cggcagcgat    780
gagggcgggt gttacttcac cgaggctctc gcggcggagg aggaggaggc gccgtttgct    840
tggtgtattt ggtcttaa                                                   858
```

<210> SEQ ID NO 22
<211> LENGTH: 285
<212> TYPE: PRT
<213> ORGANISM: Craterostigma plantagineum

<400> SEQUENCE: 22

Met Asn Ser Ala Arg Ile Phe Phe Asp Pro Ser Ser His Gly Asn Met
1               5                   10                  15

Leu Gln Phe Leu Gly Asn Ala Gly Gly Asp Ser Ser Val Phe Arg Gly
            20                  25                  30

Thr Arg Ser Ser Ser Val Leu Asn Met Glu Glu Ser Ser Leu Lys Arg
        35                  40                  45

Gln Ile Phe Ser Gly Gly Gly Gly Asp Glu Phe Tyr Asp Glu Glu Tyr
    50                  55                  60

Tyr Asp Glu Gln Leu Leu Pro Glu Lys Lys Arg Arg Leu Thr Ala Glu
65                  70                  75                  80

Gln Val His Leu Leu Glu Lys Ser Phe Glu Ala Glu Asn Lys Leu Glu
                85                  90                  95

Pro Glu Arg Lys Ala Glu Leu Ala Lys Lys Leu Gly Leu Gln Pro Arg
            100                 105                 110

Gln Val Ala Ile Trp Phe Gln Asn Arg Arg Ala Arg Trp Lys Thr Lys
        115                 120                 125

Gln Leu Glu Arg Asp Tyr Asp Lys Leu Lys Ser Ser Tyr Asp Ser Leu
    130                 135                 140

Leu Ser Thr Tyr Asp Ser Ile Arg Gln Glu Asn Asp Lys Leu Lys Ala
145                 150                 155                 160

Glu Leu Leu Ser Leu Asn Glu Lys Leu Gln Pro Lys Asp Asp Asp Asp
                165                 170                 175

```
Pro Ser Ala Glu Ile Gly Arg Asn Leu Ser Ser Ser Pro Pro Val
            180                 185                 190

Asp Ala Ala Glu Pro Pro Cys Leu Lys Leu Thr Val Lys Val Glu Asp
            195                 200                 205

Arg Leu Ser Thr Gly Ser Asn Gly Ser Ala Val Met Asp Gly Asp Gly
            210                 215                 220

Pro Gln Gln Leu Leu Asp Asp Ser Gly Asp Ser Tyr Phe Glu Asn Asp
225                 230                 235                 240

Glu Glu Tyr Asp Cys Ala Ala Ala Ser Leu Ala Ala Ala Lys Glu Asp
                245                 250                 255

Asp Gly Ser Asp Glu Gly Gly Cys Tyr Phe Thr Glu Ala Leu Ala Ala
            260                 265                 270

Glu Glu Glu Glu Ala Pro Phe Ala Trp Cys Ile Trp Ser
            275                 280                 285
```

```
<210> SEQ ID NO 23
<211> LENGTH: 813
<212> TYPE: DNA
<213> ORGANISM: Gossypium hirsutum
<220> FEATURE:
<221> NAME/KEY: misc_feature
<222> LOCATION: (808)..(808)
<223> OTHER INFORMATION: n is a, c, g, or t

<400> SEQUENCE: 23
atggagtctg ccgtcttttt tttcaatccc tccactaccc accgcaacat gttgcttctc      60
gggaacactg aacccatctt tcgaggggca agaacaatgg ttagcatgga ggaaaaccca     120
aagaagcgac tgttcttcag ctcgccggag gatttgtacg acgaagagta ctacgacgag     180
cagttgcccg agaaaaagcg tcgccttacg tcggagcagg tgtatctgct agagaagagc     240
tttgaggcag agaacaagct ggagccggag aggaagagcc agttggccaa gaagttagga     300
ctgcaaccaa ggcaggtggc ggtatggttc cagaaccgcc gtgcaaggtg aagacaaag     360 cagcttgaaa gggactatga cctcctcaaa tcttcctttg attcccttca gtccaattat     420
gacactattc tcaaagaaaa tgagaagctc aaatctgagg tagcttcctt gactgaaaaa     480
ctacaagcca agatgtggc aacagaagca atagcaggtg aaaaggatga agggttagca     540
gctgagatgg cctccgccct ccaattcagt atgaaggtgg aggaccgtct tagtagcggc     600
agtgtcggaa gcgcggtggt ggatgaggat gccccacagc tggtggacag cggcaattcc     660
tactttccaa gcgatgaata ctccagaggc attggccctt cgatggggt tcagtcggaa     720 gatgaggatg gcagtgataa ttgcgggagt tacttctccg atgtgttcgc aaccacagag     780
cagggagcat taggattgtg ggcctggntc taa                                 813
```

```
<210> SEQ ID NO 24
<211> LENGTH: 270
<212> TYPE: PRT
<213> ORGANISM: Gossypium hirsutum
<220> FEATURE:
<221> NAME/KEY: UNSURE
<222> LOCATION: (270)..(270)
<223> OTHER INFORMATION: Unknown amino acid

<400> SEQUENCE: 24

Met Glu Ser Gly Arg Leu Phe Phe Asn Pro Ser Thr Thr His Arg Asn
1               5                   10                  15

Met Leu Leu Leu Gly Asn Thr Glu Pro Ile Phe Arg Gly Ala Arg Thr
            20                  25                  30
```

```
Met Val Ser Met Glu Glu Asn Pro Lys Lys Arg Leu Phe Ser Ser
            35                  40                  45

Pro Glu Asp Leu Tyr Asp Glu Tyr Tyr Asp Glu Gln Leu Pro Glu
 50                  55                  60

Lys Lys Arg Arg Leu Thr Ser Glu Gln Val Tyr Leu Leu Glu Lys Ser
 65                  70                  75                  80

Phe Glu Ala Glu Asn Lys Leu Glu Pro Glu Arg Lys Ser Gln Leu Ala
                 85                  90                  95

Lys Lys Leu Gly Leu Gln Pro Arg Gln Val Ala Val Trp Phe Gln Asn
             100                 105                 110

Arg Arg Ala Arg Trp Lys Thr Lys Gln Leu Glu Arg Asp Tyr Asp Leu
         115                 120                 125

Leu Lys Ser Ser Phe Asp Ser Leu Gln Ser Asn Tyr Asp Thr Ile Leu
     130                 135                 140

Lys Glu Asn Glu Lys Leu Lys Ser Glu Val Ala Ser Leu Thr Glu Lys
 145                 150                 155                 160

Leu Gln Ala Lys Asp Val Ala Thr Glu Ala Ile Ala Gly Glu Lys Asp
                 165                 170                 175

Glu Gly Leu Ala Ala Glu Met Ala Ser Ala Leu Gln Phe Ser Met Lys
             180                 185                 190

Val Glu Asp Arg Leu Ser Ser Gly Ser Val Gly Ser Ala Val Val Asp
         195                 200                 205

Glu Asp Ala Pro Gln Leu Val Asp Ser Gly Asn Ser Tyr Phe Pro Ser
     210                 215                 220

Asp Glu Tyr Ser Arg Gly Ile Gly Pro Phe Asp Gly Val Gln Ser Glu
 225                 230                 235                 240

Asp Glu Asp Gly Ser Asp Asn Cys Gly Ser Tyr Phe Ser Asp Val Phe
                 245                 250                 255

Ala Thr Thr Glu Gln Gly Ala Leu Gly Leu Trp Ala Trp Xaa
             260                 265                 270

<210> SEQ ID NO 25
<211> LENGTH: 858
<212> TYPE: DNA
<213> ORGANISM: Lycopersicon esculentum
<220> FEATURE:
<221> NAME/KEY: misc_feature
<222> LOCATION: (294)..(294)
<223> OTHER INFORMATION: n is a, c, g, or t

<400> SEQUENCE: 25
atgggatctg gcatatatt tttcgacccg tcgtcgtgtc acggcaacat gctgttcctt      60
gggagcggag atcctgtttt ccgaggacca agatcgacga tgatgaagat ggaggactcc    120
tcgaagaggc gacccttctt tagctcgccg gaggatctat atgacgagga atactacgac    180
gagcagtcac cggagaagaa gcgccgtctc actcctgagc aggtgcactt gttggagaag    240
agctttgaga cagaaaacaa gctggagccc gagcgcaaaa cccagctggc ctanaagctg    300
gggctgcagc ccagacaggt ggctgtatgg ttccaaaacc gccgtgcccg gtggaagacc    360
aagcagctcg agagggatta tgatcagctc aaatcctctt atgactccct tctctctgat    420
tttgactccg ttcgcaaaga taacgataag ctcaaatctg aggttgtttc attgatggaa    480
aagttacagg ggaaagtggt tggaggagca ggggaaatg aaaaatctga catcttggag    540
gtggatgcta tgacgatcct tcaagtgaag gtgaaggctg ggaccggtt gagcagtggc    600 agtggtggga gcgcggtggt agatgagcat agttcacagc tggtggacag tggggactca    660
tattttcaca ctgatcatga ggagtatcca gggcctggag gatgcaatgt tcctccaccc    720
```

```
atggatggtt  tacaatcgga  ggaagatgat  ggtagtgatg  atcatggcag  ttgccatggc    780
tacttctcta  acgtctttgt  ggcagaagag  cagcaccatg  aacaaggaga  agagcctatt    840
ggatggttct  ggtcttaa                                                       858
```

<210> SEQ ID NO 26
<211> LENGTH: 285
<212> TYPE: PRT
<213> ORGANISM: Lycopersicon esculentum
<220> FEATURE:
<221> NAME/KEY: UNSURE
<222> LOCATION: (98)..(98)
<223> OTHER INFORMATION: Unknown amino acid

<400> SEQUENCE: 26

```
Met Gly Ser Gly His Ile Phe Phe Asp Pro Ser Ser Cys His Gly Asn
1               5                   10                  15

Met Leu Phe Leu Gly Ser Gly Asp Pro Val Phe Arg Gly Pro Arg Ser
            20                  25                  30

Thr Met Met Lys Met Glu Asp Ser Ser Lys Arg Arg Pro Phe Phe Ser
        35                  40                  45

Ser Pro Glu Asp Leu Tyr Asp Glu Glu Tyr Tyr Asp Glu Gln Ser Pro
    50                  55                  60

Glu Lys Lys Arg Arg Leu Thr Pro Glu Gln Val His Leu Leu Glu Lys
65                  70                  75                  80

Ser Phe Glu Thr Glu Asn Lys Leu Glu Pro Glu Arg Lys Thr Gln Leu
                85                  90                  95

Ala Xaa Lys Leu Gly Leu Gln Pro Arg Gln Val Ala Val Trp Phe Gln
            100                 105                 110

Asn Arg Arg Ala Arg Trp Lys Thr Lys Gln Leu Glu Arg Asp Tyr Asp
        115                 120                 125

Gln Leu Lys Ser Ser Tyr Asp Ser Leu Leu Ser Asp Phe Asp Ser Val
    130                 135                 140

Arg Lys Asp Asn Asp Lys Leu Lys Ser Glu Val Val Ser Leu Met Glu
145                 150                 155                 160

Lys Leu Gln Gly Lys Val Val Gly Gly Ala Gly Asn Glu Lys Ser
                165                 170                 175

Asp Ile Leu Glu Val Asp Ala Met Thr Ile Leu Gln Val Lys Val Lys
            180                 185                 190

Ala Gly Asp Arg Leu Ser Ser Gly Ser Gly Gly Ser Ala Val Val Asp
        195                 200                 205

Glu His Ser Ser Gln Leu Val Asp Ser Gly Asp Ser Tyr Phe His Thr
    210                 215                 220

Asp His Glu Glu Tyr Pro Gly Pro Gly Cys Asn Val Pro Pro
225                 230                 235                 240

Met Asp Gly Leu Gln Ser Glu Glu Asp Gly Ser Asp Asp His Gly
                245                 250                 255

Ser Cys His Gly Tyr Phe Ser Asn Val Phe Val Ala Glu Glu Gln His
            260                 265                 270

His Glu Gln Gly Glu Glu Pro Ile Gly Trp Phe Trp Ser
        275                 280                 285
```

<210> SEQ ID NO 27
<211> LENGTH: 972
<212> TYPE: DNA
<213> ORGANISM: Lycopersicon esculentum

<400> SEQUENCE: 27

```
atggctccag ggattctcta tggtggttct tctaatttcg atggcgtttt tactcaaaaa    60
cagagagacg tgttttcttc atctactgca ccgaaagggc atcttggttc ccttttttgcc  120 cctgcctctt cttcttctaa tttcttggga tccagttcta tggtgagttt tcgcggtgtt  180
aatggaggga agagatcatt ctttgattcg ttcgatcagg atgacaatga agctgatgaa  240 ttggggaat atcttcatca agcggagaag aagaggcgac ttactgacaa ccaagttcag    300
tttcttgaga gagttttggg ggaagagaac aaacttgaac cagaaagaaa agttcagctt  360
gctaaagaac ttggtctgca gcctcgccaa attgcaattt ggtttcagaa tcgtcgtgcg  420
cgatggaaga ctaagcagct cgagaaagat tatgatgaat gaggaatag atacgatact    480 ctgaaatcaa attacaataa tcttctcaag gaaaaagaag atcttcgaac tgaagttttc  540
cgtctcaccg gtaagctgtt tatcaaagag aaaggaaatg ggcaattgga tttgcgcgat  600
gaacacaaac actccaatgc attggcaaaa gaaccgtgg ttgatccaat gtccaatgta    660
ccagctctgg ttgttaagca ccagcaggaa gatttaagct ctgctaagag tgatgttttc  720
gactcagaaa gcccacgtta caccagtaga atgcattcct cagtcgtaga tcaggatgat  780
tctgctcgcg catttgaaac tgatcagtcg gattcatctc aggatgatga tgaaaacttc  840
agcaagaata tgctttctac tgccaaccta cttggcaaag acgcggatga tgattatccc  900
gcgacatcat caaatttgag ttactttgga tttccagttg aagaccaagg ttttggtttc  960
tggacttatt aa                                                       972

<210> SEQ ID NO 28
<211> LENGTH: 323
<212> TYPE: PRT
<213> ORGANISM: Lycopersicon esculentum

<400> SEQUENCE: 28

Met Ala Pro Gly Ile Leu Tyr Gly Gly Ser Ser Asn Phe Asp Gly Val
1               5                   10                  15

Phe Thr Gln Lys Gln Arg Asp Val Phe Ser Ser Ser Thr Ala Pro Lys
                20                  25                  30

Gly His Leu Gly Ser Leu Phe Ala Pro Ala Ser Ser Ser Ser Asn Phe
            35                  40                  45

Leu Gly Ser Ser Ser Met Val Ser Phe Arg Gly Val Asn Gly Gly Lys
        50                  55                  60

Arg Ser Phe Phe Asp Ser Phe Asp Gln Asp Asp Asn Glu Ala Asp Glu
65                  70                  75                  80

Leu Gly Glu Tyr Leu His Gln Ala Glu Lys Lys Arg Arg Leu Thr Asp
                85                  90                  95

Asn Gln Val Gln Phe Leu Glu Lys Ser Phe Gly Glu Asn Lys Leu
            100                 105                 110

Glu Pro Glu Arg Lys Val Gln Leu Ala Lys Glu Leu Gly Leu Gln Pro
        115                 120                 125

Arg Gln Ile Ala Ile Trp Phe Gln Asn Arg Arg Ala Arg Trp Lys Thr
    130                 135                 140

Lys Gln Leu Glu Lys Asp Tyr Asp Glu Leu Arg Asn Arg Tyr Asp Thr
145                 150                 155                 160

Leu Lys Ser Asn Tyr Asn Asn Leu Leu Lys Glu Lys Asp Leu Arg
                165                 170                 175

Thr Glu Val Phe Arg Leu Thr Gly Lys Leu Phe Ile Lys Glu Lys Gly
            180                 185                 190

Asn Gly Gln Leu Asp Leu Arg Asp Glu His Lys His Ser Asn Ala Leu
```

```
                195                 200                 205
Ala Lys Glu Thr Val Val Asp Pro Met Ser Asn Val Pro Ala Leu Val
        210                 215                 220

Val Lys His Gln Gln Glu Asp Leu Ser Ser Ala Lys Ser Asp Val Phe
225                 230                 235                 240

Asp Ser Glu Ser Pro Arg Tyr Thr Ser Arg Met His Ser Ser Val Val
                245                 250                 255

Asp Gln Asp Asp Ser Ala Arg Ala Phe Glu Thr Asp Gln Ser Asp Ser
            260                 265                 270

Ser Gln Asp Asp Asp Glu Asn Phe Ser Lys Asn Met Leu Ser Thr Ala
        275                 280                 285

Asn Leu Leu Gly Lys Asp Ala Asp Asp Asp Tyr Pro Ala Thr Ser Ser
    290                 295                 300

Asn Leu Ser Tyr Phe Gly Phe Pro Val Glu Asp Gln Gly Phe Gly Phe
305                 310                 315                 320

Trp Thr Tyr

<210> SEQ ID NO 29
<211> LENGTH: 1014
<212> TYPE: DNA
<213> ORGANISM: Medicago sativa

<400> SEQUENCE: 29
atggcgggtg ggagagtttt ttcaaatggt cctgcaaata tttcaaatat aaatatgaat      60
attttgcttc agaatcaaca acaaactcct cgtggaaaact cttctcaaca acctcttgat     120
tctcttttcc tttcttcttc tgcttctttc tttggttcaa gatctatggt gagttttgaa     180
gatgttcaag gaaggaaaag gcgcaacagg tctttctttg gaggatttga tcttgacgaa     240
aacggagagg atgagatgga tgagtacttt catcaatccg agaagaaacg gcgtctctca     300
gtggatcaag ttcagtttct tgagaaaagc tttgaggagg acaacaaact tgaaccagag     360
aggaaaacca agctagctaa agaccttggt ttgcagccac ggcaagttgc tatttggttt     420
caaaaccgtc gtgcaaggtg gaagactaaa cagcttgaga aggattatga ttctcttaat     480
gatggttatg agtctcttaa gacagagtat gacaaccttc tcaaagagaa agataggtta     540
caatctgagg tggcaagcct aactgaaaag gtacttgaaa gagagaaaca agagggaaaa     600
ttcaaacaag gtgaaagtga aacaaaggaa ttcttgaagg aaccaacaat taataagcct     660
ttggttgatt cagtttctga gggtgaagga tccaaattgt caattgttga ggcttctaat     720
aataataata ataataacaa acttgaagat attagttcag caaggagtga catattggat     780
tgtgaaagtc cacgctacac tgatggagtg ttagagacat gtgattcttc ctatgtattt     840
gaacctgaat atcaatcgga cctatcacaa gatgaagaag atcacaattt attgcctcct     900
tacatcttta caaaacttga agatgtgaat tactccgacc cgccacataa ttcaacaagt     960
tatggatttc aagaggaaga tcatcatcaa gctctttggc cttggtctta ttag           1014

<210> SEQ ID NO 30
<211> LENGTH: 337
<212> TYPE: PRT
<213> ORGANISM: Medicago sativa

<400> SEQUENCE: 30

Met Ala Gly Gly Arg Val Phe Ser Asn Gly Pro Ala Asn Ile Ser Asn
1               5                   10                  15

Ile Asn Met Asn Ile Leu Leu Gln Asn Gln Gln Gln Thr Pro Arg Gly
            20                  25                  30
```

```
Asn Ser Ser Gln Gln Pro Leu Asp Ser Leu Phe Leu Ser Ser Ala
         35                  40                  45
Ser Phe Phe Gly Ser Arg Ser Met Val Ser Phe Glu Asp Val Gln Gly
 50                  55                  60
Arg Lys Arg Arg Asn Arg Ser Phe Phe Gly Gly Phe Asp Leu Asp Glu
 65                  70                  75                  80
Asn Gly Glu Asp Glu Met Asp Glu Tyr Phe His Gln Ser Glu Lys Lys
                 85                  90                  95
Arg Arg Leu Ser Val Asp Gln Val Gln Phe Leu Glu Lys Ser Phe Glu
                100                 105                 110
Glu Asp Asn Lys Leu Glu Pro Glu Arg Lys Thr Lys Leu Ala Lys Asp
                115                 120                 125
Leu Gly Leu Gln Pro Arg Gln Val Ala Ile Trp Phe Gln Asn Arg Arg
         130                 135                 140
Ala Arg Trp Lys Thr Lys Gln Leu Glu Lys Asp Tyr Asp Ser Leu Asn
145                 150                 155                 160
Asp Gly Tyr Glu Ser Leu Lys Thr Glu Tyr Asp Asn Leu Leu Lys Glu
                165                 170                 175
Lys Asp Arg Leu Gln Ser Glu Val Ala Ser Leu Thr Glu Lys Val Leu
                180                 185                 190
Glu Arg Glu Lys Gln Glu Gly Lys Phe Lys Gln Gly Glu Ser Glu Thr
            195                 200                 205
Lys Glu Phe Leu Lys Glu Pro Thr Ile Asn Lys Pro Leu Val Asp Ser
            210                 215                 220
Val Ser Glu Gly Glu Gly Ser Lys Leu Ser Ile Val Glu Ala Ser Asn
225                 230                 235                 240
Asn Asn Asn Asn Asn Lys Leu Glu Asp Ile Ser Ser Ala Arg Ser
                245                 250                 255
Asp Ile Leu Asp Cys Glu Ser Pro Arg Tyr Thr Asp Gly Val Leu Glu
            260                 265                 270
Thr Cys Asp Ser Ser Tyr Val Phe Glu Pro Glu Tyr Gln Ser Asp Leu
            275                 280                 285
Ser Gln Asp Glu Glu Asp His Asn Leu Leu Pro Pro Tyr Ile Phe Thr
        290                 295                 300
Lys Leu Glu Asp Val Asn Tyr Ser Asp Pro Pro His Asn Ser Thr Ser
305                 310                 315                 320
Tyr Gly Phe Gln Glu Glu Asp His His Gln Ala Leu Trp Pro Trp Ser
                325                 330                 335
Tyr
```

<210> SEQ ID NO 31
<211> LENGTH: 843
<212> TYPE: DNA
<213> ORGANISM: Aquilegia formosa x Aquilegia pubescens

<400> SEQUENCE: 31

```
atggattcaa caacaagccg tcttttcttt gatggttcct gccatgggaa catgttgctt      60
ttagggagtg gagatcccgt tcttcgaggt tcaagatcat tcattaatat ggaagattct     120
ttgaaaagac gtcctttttta gttcaaca gatgaactaa ttgaagagga gttttatgat     180
gaacagctac ctgaaaagaa acgtcgtctt acttctgagc aggttcatct attggagaag     240
agctttgaga cagagaacaa gctggaacca gatcgtaaga cccagcttgc taagaagctt     300
gggttgcaac cgagacaagt tgcagtttgg tttcagaata cgagctcg ttggaagact     360
```

```
aagcaactag agagagatta tgatcttctt aaagcttctt atgattccct tcgttctgat      420
tacgatgaca ttgttaaaga gaatgagaag ctcaaatctg aggtggtttc cttaactggg      480
aagttgcagg tcaaggaggg agctgggatg gagttaaatc agatatctga cccaccactc      540
tccactgaag aaaatgttga tgtaactacg atgcaattta atgttaaggt tgaggatcgc      600
ttgagctctg gcagtggggt aagtgctgtg gttgatgagg aatgtcgaca gcttgttgac      660
agtgttgatt cctatttccc tggcgatgac tatggtcaat gcataggccc agtagatgga      720
gtccagtcag aagaagatga cattagtgac gacagccgga gctatttctc agatgtcttt      780
ccagctgcac cagagcagaa ccaccaggag agtgagacat tgggttggtg ggactgggct      840
taa                                                                   843
```

<210> SEQ ID NO 32
<211> LENGTH: 280
<212> TYPE: PRT
<213> ORGANISM: Aquilegia formosa x Aquilegia pubescens

<400> SEQUENCE: 32

```
Met Asp Ser Thr Thr Ser Arg Leu Phe Phe Asp Gly Ser Cys His Gly
1               5                   10                  15

Asn Met Leu Leu Leu Gly Ser Gly Asp Pro Val Leu Arg Gly Ser Arg
            20                  25                  30

Ser Phe Ile Asn Met Glu Asp Ser Leu Lys Arg Arg Pro Phe Tyr Ser
        35                  40                  45

Ser Thr Asp Glu Leu Ile Glu Glu Phe Tyr Asp Glu Gln Leu Pro
    50                  55                  60

Glu Lys Lys Arg Arg Leu Thr Ser Glu Gln Val His Leu Leu Glu Lys
65                  70                  75                  80

Ser Phe Glu Thr Glu Asn Lys Leu Glu Pro Asp Arg Lys Thr Gln Leu
                85                  90                  95

Ala Lys Lys Leu Gly Leu Gln Pro Arg Gln Val Ala Val Trp Phe Gln
            100                 105                 110

Asn Arg Arg Ala Arg Trp Lys Thr Lys Gln Leu Glu Arg Asp Tyr Asp
        115                 120                 125

Leu Leu Lys Ala Ser Tyr Asp Ser Leu Arg Ser Asp Tyr Asp Asp Ile
    130                 135                 140

Val Lys Glu Asn Glu Lys Leu Lys Ser Glu Val Val Ser Leu Thr Gly
145                 150                 155                 160

Lys Leu Gln Val Lys Glu Gly Ala Gly Met Glu Leu Asn Gln Ile Ser
                165                 170                 175

Asp Pro Pro Leu Ser Thr Glu Glu Asn Val Asp Val Thr Thr Met Gln
            180                 185                 190

Phe Asn Val Lys Val Glu Asp Arg Leu Ser Ser Gly Ser Gly Val Ser
        195                 200                 205

Ala Val Val Asp Glu Glu Cys Arg Gln Leu Val Asp Ser Val Asp Ser
    210                 215                 220

Tyr Phe Pro Gly Asp Asp Tyr Gly Gln Cys Ile Gly Pro Val Asp Gly
225                 230                 235                 240

Val Gln Ser Glu Glu Asp Asp Ile Ser Asp Asp Ser Arg Ser Tyr Phe
                245                 250                 255

Ser Asp Val Phe Pro Ala Ala Pro Glu Gln Asn His Gln Glu Ser Glu
            260                 265                 270

Thr Leu Gly Trp Trp Asp Trp Ala
        275                 280
```

<210> SEQ ID NO 33
<211> LENGTH: 2193
<212> TYPE: DNA
<213> ORGANISM: Oryza sativa

<400> SEQUENCE: 33

| | | | | | |
|---|---|---|---|---|---|
| aatccgaaaa | gtttctgcac | cgttttcacc | ccctaactaa | caatataggg | aacgtgtgct | 60 |
| aaatataaaa | tgagacctta | tatatgtagc | gctgataact | agaactatgc | aagaaaaact | 120 |
| catccaccta | ctttagtggc | aatcgggcta | aataaaaaag | agtcgctaca | ctagtttcgt | 180 |
| tttccttagt | aattaagtgg | gaaaatgaaa | tcattattgc | ttagaatata | cgttcacatc | 240 |
| tctgtcatga | agttaaatta | ttcgaggtag | ccataattgt | catcaaactc | ttcttgaata | 300 |
| aaaaaatctt | tctagctgaa | ctcaatgggt | aaagagagag | atttttttta | aaaaaataga | 360 |
| atgaagatat | tctgaacgta | ttggcaaaga | tttaaacata | taattatata | attttatagt | 420 |
| ttgtgcattc | gtcatatcgc | acatcattaa | ggacatgtct | tactccatcc | caatttttat | 480 |
| ttagtaatta | aagacaattg | acttatttt | attatttatc | tttttcgat | tagatgcaag | 540 |
| gtacttacgc | acacactttg | tgctcatgtg | catgtgtgag | tgcacctcct | caatacacgt | 600 |
| tcaactagca | acacatctct | aatatcactc | gcctatttaa | tacatttagg | tagcaatatc | 660 |
| tgaattcaag | cactccacca | tcaccagacc | acttttaata | atatctaaaa | tacaaaaaat | 720 |
| aattttacag | aatagcatga | aaagtatgaa | acgaactatt | taggttttc | acatacaaaa | 780 |
| aaaaaagaa | ttttgctcgt | gcgcgagcgc | caatctccca | tattgggcac | acaggcaaca | 840 |
| acagagtggc | tgcccacaga | acaacccaca | aaaaacgatg | atctaacgga | ggacagcaag | 900 |
| tccgcaacaa | ccttttaaca | gcaggctttg | cggccaggag | agaggaggag | aggcaaagaa | 960 |
| aaccaagcat | cctcctcctc | ccatctataa | attcctcccc | cctttcccc | tctctatata | 1020 |
| ggaggcatcc | aagccaagaa | gagggagagc | accaaggaca | cgcgactagc | agaagccgag | 1080 |
| cgaccgcctt | cttcgatcca | tatcttccgg | tcgagttctt | ggtcgatctc | ttccctcctc | 1140 |
| cacctcctcc | tcacagggta | tgtgcccttc | ggttgttctt | ggatttattg | ttctaggttg | 1200 |
| tgtagtacgg | gcgttgatgt | taggaaaggg | gatctgtatc | tgtgatgatt | cctgttcttg | 1260 |
| gatttgggat | agaggggttc | ttgatgttgc | atgttatcgg | ttcggtttga | ttagtagtat | 1320 |
| ggttttcaat | cgtctggaga | gctctatgga | aatgaaatgg | tttagggtac | ggaatcttgc | 1380 |
| gattttgtga | gtaccttttg | tttgaggtaa | aatcagagca | ccggtgattt | gcttggtgt | 1440 |
| aataaaagta | cggttgtttg | gtcctcgatt | ctggtagtga | tgcttctcga | tttgacgaag | 1500 |
| ctatcctttg | tttattccct | attgaacaaa | aataatccaa | ctttgaagac | ggtcccgttg | 1560 |
| atgagattga | atgattgatt | cttaagcctg | tccaaaattt | cgcagctggc | ttgtttagat | 1620 |
| acagtagtcc | ccatcacgaa | attcatggaa | acagttataa | tcctcaggaa | caggggattc | 1680 |
| cctgttcttc | cgatttgctt | tagtcccaga | attttttttc | ccaaatatct | taaaaagtca | 1740 |
| ctttctggtt | cagttcaatg | aattgattgc | tacaaataat | gcttttatag | cgttatccta | 1800 |
| gctgtagttc | agttaatagg | taatacccct | atagtttagt | caggagaaga | acttatccga | 1860 |
| tttctgatct | ccatttttaa | ttatatgaaa | tgaactgtag | cataagcagt | attcatttgg | 1920 |
| attatttttt | ttattagctc | tcaccccttc | attattctga | gctgaaagtc | tggcatgaac | 1980 |
| tgtcctcaat | tttgtttca | aattcacatc | gattatctat | gcattatcct | cttgtatcta | 2040 |
| cctgtagaag | tttcttttg | gttattcctt | gactgcttga | ttacagaaag | aaatttatga | 2100 |
| agctgtaatc | gggatagtta | tactgcttgt | tcttatgatt | catttccttt | gtgcagttct | 2160 |

```
tggtgtagct tgccactttc accagcaaag ttc                                    2193
```

<210> SEQ ID NO 34
<211> LENGTH: 49
<212> TYPE: DNA
<213> ORGANISM: Artificial sequence
<220> FEATURE:
<223> OTHER INFORMATION: primer: prm6000

<400> SEQUENCE: 34

```
ggggacaagt ttgtacaaaa aagcaggctt aaacaatgga tcccggccg                    49
```

<210> SEQ ID NO 35
<211> LENGTH: 48
<212> TYPE: DNA
<213> ORGANISM: Artificial sequence
<220> FEATURE:
<223> OTHER INFORMATION: primer: prm6001

<400> SEQUENCE: 35

```
ggggaccact ttgtacaaga aagctgggtg atcagctcca gaaccagg                     48
```

<210> SEQ ID NO 36
<211> LENGTH: 834
<212> TYPE: DNA
<213> ORGANISM: Oryza sativa

<400> SEQUENCE: 36

```
atgaagcgac cggcggtgc cggcggcggc ggaggcagcc catcgctcgt cacgatggct         60
aattctagtg atgatggata tggaggggtt gggatggagg cggaggggga cgtggaggag       120
gagatgatgg cgtgcggcgg cggcggggag aagaagcggc ggctgagcgt ggagcaggtt       180
cgcgcgctgg agcggagctt cgaggtggag aacaagcttg agcctgagcg gaaggcgcgg       240
ctggcgcgcg acctcggcct gcagccgcgc caggtcgccg tctggttcca gaaccgccgc       300
gcgcggtgga agaccaagca gctcgagcgc gactacgccg cgctccgcca ttcctacgac       360
tccctgcgcc tcgatcacga gcgctccgc cgcgacaagg acgccctcct cgccgagatc       420
aaggagctga aggcgaagct cggggacgag gaggcggcgg cgagcttcac gtcggtgaag       480
gaggagccgg cggcctccga cgggccaccg gcggcgggat ttgggtcgtc cgacagcgac       540
tcaagcgcg tgctgaacga cgtggacgcg gccggcgccg cgcccgcggc gacggacgcg       600
ctggctccgg aggcgtgcac gtttctcggt gcgccgcccg ccgcgggcgc gggcgcgggc       660
gcagcggcg cggcgagcca cgaggaggtg ttcttccacg gcaatttcct caaggtggag       720
gaggacgaga cggggttcct cgacgacgac gagccgtgcg gcgggttctt cgccgacgat       780
cagcccccgc cgctctcgtc gtggtgggcc gaaccacgg agcactggaa ctga             834
```

<210> SEQ ID NO 37
<211> LENGTH: 277
<212> TYPE: PRT
<213> ORGANISM: Oryza sativa

<400> SEQUENCE: 37

```
Met Lys Arg Pro Gly Gly Ala Gly Gly Gly Gly Ser Pro Ser Leu
1               5                   10                  15

Val Thr Met Ala Asn Ser Ser Asp Asp Gly Tyr Gly Gly Val Gly Met
            20                  25                  30

Glu Ala Glu Gly Asp Val Glu Glu Met Met Ala Cys Gly Gly Gly
        35                  40                  45

Gly Glu Lys Lys Arg Arg Leu Ser Val Glu Gln Val Arg Ala Leu Glu
```

```
                50                   55                  60
Arg Ser Phe Glu Val Glu Asn Lys Leu Glu Pro Glu Arg Lys Ala Arg
 65                   70                   75                  80

Leu Ala Arg Asp Leu Gly Leu Gln Pro Arg Gln Val Ala Val Trp Phe
                 85                   90                   95

Gln Asn Arg Arg Ala Arg Trp Lys Thr Lys Gln Leu Glu Arg Asp Tyr
                100                  105                  110

Ala Ala Leu Arg His Ser Tyr Asp Ser Leu Arg Leu Asp His Asp Ala
                115                  120                  125

Leu Arg Arg Asp Lys Asp Ala Leu Leu Ala Glu Ile Lys Glu Leu Lys
130                  135                  140

Ala Lys Leu Gly Asp Glu Ala Ala Ala Ser Phe Thr Ser Val Lys
145                  150                  155                  160

Glu Glu Pro Ala Ala Ser Asp Gly Pro Ala Ala Gly Phe Gly Ser
                165                  170                  175

Ser Asp Ser Asp Ser Ser Ala Val Leu Asn Asp Val Asp Ala Ala Gly
                180                  185                  190

Ala Ala Pro Ala Ala Thr Asp Ala Leu Ala Pro Glu Ala Cys Thr Phe
                195                  200                  205

Leu Gly Ala Pro Pro Ala Ala Gly Ala Gly Ala Ala Ala Ala
210                  215                  220

Ala Ser His Glu Glu Val Phe Phe His Gly Asn Phe Leu Lys Val Glu
225                  230                  235                  240

Glu Asp Glu Thr Gly Phe Leu Asp Asp Glu Pro Cys Gly Gly Phe
                245                  250                  255

Phe Ala Asp Asp Gln Pro Pro Leu Ser Ser Trp Trp Ala Glu Pro
                260                  265                  270

Thr Glu His Trp Asn
        275

<210> SEQ ID NO 38
<211> LENGTH: 750
<212> TYPE: DNA
<213> ORGANISM: Oryza sativa

<400> SEQUENCE: 38
atggatgggg aggaggacag cgagtggatg atgatggacg ttggagggaa gggcgggaag      60
ggcggcggcg gcggcggcgc ggcggacagg aagaagcggt tcagcgagga gcagatcaag     120
tcgctggagt ccatgttcgc gacgcagacc aagctggagc cgaggcagaa gctgcagctc     180
gccagggagc tcggcctgca gcctcgccag gtcgccatct ggttccagaa caagcgcgcg     240
cggtggaagt ccaagcagct cgagcgcgag tactccgccc tccgcgacga ctacgacgcc     300
ctcctctgca gctacgagtc cctcaagaag gagaagctcg ccctcatcaa gcagctggag     360
aagctggcgg agatgctgca ggagccacgg ggaagtacg gcgataatgc cggggacgac     420
gcgcggtcgg gcggcgtcgc cggcatgaag aaggaggagt cgtcggcgc gggcggcgcc     480 gccacgctct actcgtcggc cgagggtggc gggacgacga cgacgacgac ggccaagttg     540
atgccccact cggcagcga cgacgtcgac gcggggctct cctccggcc gtcgtcgcag     600 catcatccgc cgccgccgca cgccggtgcc ggcttcacgt cctccgagcc ggccgccgac     660
caccagtcct tcaacttcca ctcgagctgg ccgtcgtcca cggagcagac ctgcagcagc     720
acgccatggt gggaattcga gagcgagtga                                     750

<210> SEQ ID NO 39
```

<211> LENGTH: 249
<212> TYPE: PRT
<213> ORGANISM: Oryza sativa

<400> SEQUENCE: 39

| Met | Asp | Gly | Glu | Glu | Asp | Ser | Glu | Trp | Met | Met | Met | Asp | Val | Gly | Gly |
|---|---|---|---|---|---|---|---|---|---|---|---|---|---|---|---|
| 1 | | | | 5 | | | | | 10 | | | | | 15 | |

Lys Gly Gly Lys Gly Gly Gly Gly Gly Ala Ala Asp Arg Lys Lys
            20                  25                  30

Arg Phe Ser Glu Glu Gln Ile Lys Ser Leu Glu Ser Met Phe Ala Thr
            35                  40                  45

Gln Thr Lys Leu Glu Pro Arg Gln Lys Leu Gln Leu Ala Arg Glu Leu
    50                  55                  60

Gly Leu Gln Pro Arg Gln Val Ala Ile Trp Phe Gln Asn Lys Arg Ala
65                  70                  75                  80

Arg Trp Lys Ser Lys Gln Leu Glu Arg Glu Tyr Ser Ala Leu Arg Asp
                85                  90                  95

Asp Tyr Asp Ala Leu Leu Cys Ser Tyr Glu Ser Leu Lys Lys Glu Lys
            100                 105                 110

Leu Ala Leu Ile Lys Gln Leu Glu Lys Leu Ala Glu Met Leu Gln Glu
        115                 120                 125

Pro Arg Gly Lys Tyr Gly Asp Asn Ala Gly Asp Ala Arg Ser Gly
    130                 135                 140

Gly Val Ala Gly Met Lys Lys Glu Glu Phe Val Gly Ala Gly Gly Ala
145                 150                 155                 160

Ala Thr Leu Tyr Ser Ser Ala Glu Gly Gly Gly Thr Thr Thr Thr Thr
                165                 170                 175

Thr Ala Lys Leu Met Pro His Phe Gly Ser Asp Asp Val Asp Ala Gly
            180                 185                 190

Leu Phe Leu Arg Pro Ser Ser Gln His His Pro Pro Pro His Ala
        195                 200                 205

Gly Ala Gly Phe Thr Ser Ser Glu Pro Ala Ala Asp His Gln Ser Phe
    210                 215                 220

Asn Phe His Ser Ser Trp Pro Ser Ser Thr Glu Gln Thr Cys Ser Ser
225                 230                 235                 240

Thr Pro Trp Trp Glu Phe Glu Ser Glu
                245

<210> SEQ ID NO 40
<211> LENGTH: 945
<212> TYPE: DNA
<213> ORGANISM: Populus tremuloides

<400> SEQUENCE: 40

```
atggcgggtg gtaccggtgg ttctaattcc aatttgtctg ttttgcttca aagccaagga      60
ggcccttgtg ctgcttcaca acctcttgaa tcttttttcc tttctggctc ttctccttct    120
tttcttggtt caagatccat gatgagtttt gaagatgttc atcaagcaaa cggatcaacc    180
aggccttttt tccgctcgtt tgatcacgaa gacaatggag acgatgatct ggatgaatat    240
tttcatcaac ctgaaaagaa gaggagactt actgttgatc aagttcagtt tcttgaaaag    300
agttttgagc ttgagaacaa gcttgaacct gaaaggaaaa tccagcttgc aaaggatctt    360
ggccttcagc cgcgtcaggt tgctatatgg tttcaaaacc gccgagcaag atggaagact    420
aaacagctgg aaaaggatta tgacgttttg caatctagct acaatagcct taaggctgac    480
tatgacaacc tcctcaagga gaaggagaaa ctaaagctg  aggttaatct tctcaccgac    540
```

```
aagttgctcc tcaaagagaa agagaaggga atctcagaat tgtctgataa agatgcatta    600
tcgcaagagc cacctaaaag ggctatagct gattcagctt ccgagggtga agtgtcgaaa    660
atctcaacag tggcctgtaa gcaggaagat atcagctcag ccaaaagcga catatttgat    720
tcagacagcc cacattacgc tgatggggtg cattcctcac tcttagaggc aggagattct    780
tcatatgttt tcgaacccga tcaatcagat ttgtcacaag atgaagaaga taactttagc    840
aagagcttat tgcctccata cgtctttccg aagcttgaag atgacgatta ctctgacccg    900
cctgcaagtt ttgaagatca tgccttttgg tcctggtcat actaa                    945
```

<210> SEQ ID NO 41
<211> LENGTH: 314
<212> TYPE: PRT
<213> ORGANISM: Populus tremuloides

<400> SEQUENCE: 41

```
Met Ala Gly Gly Thr Gly Gly Ser Asn Ser Asn Leu Ser Val Leu Leu
1               5                   10                  15

Gln Ser Gln Arg Gly Pro Cys Ala Ala Ser Gln Pro Leu Glu Ser Phe
            20                  25                  30

Phe Leu Ser Gly Ser Ser Pro Ser Phe Leu Gly Ser Arg Ser Met Met
        35                  40                  45

Ser Phe Glu Asp Val His Gln Ala Asn Gly Ser Thr Arg Pro Phe Phe
50                  55                  60

Arg Ser Phe Asp His Glu Asp Asn Gly Asp Asp Leu Asp Glu Tyr
65                  70                  75                  80

Phe His Gln Pro Glu Lys Lys Arg Arg Leu Thr Val Asp Gln Val Gln
                85                  90                  95

Phe Leu Glu Lys Ser Phe Glu Leu Glu Asn Lys Leu Glu Pro Glu Arg
            100                 105                 110

Lys Ile Gln Leu Ala Lys Asp Leu Gly Leu Gln Pro Arg Gln Val Ala
        115                 120                 125

Ile Trp Phe Gln Asn Arg Arg Ala Arg Trp Lys Thr Lys Gln Leu Glu
130                 135                 140

Lys Asp Tyr Asp Val Leu Gln Ser Ser Tyr Asn Ser Leu Lys Ala Asp
145                 150                 155                 160

Tyr Asp Asn Leu Leu Lys Glu Lys Glu Lys Leu Lys Ala Glu Val Asn
                165                 170                 175

Leu Leu Thr Asp Lys Leu Leu Leu Lys Glu Lys Glu Lys Gly Ile Ser
            180                 185                 190

Glu Leu Ser Asp Lys Asp Ala Leu Ser Gln Glu Pro Pro Lys Arg Ala
        195                 200                 205

Ile Ala Asp Ser Ala Ser Glu Gly Glu Val Ser Lys Ile Ser Thr Val
210                 215                 220

Ala Cys Lys Gln Glu Asp Ile Ser Ser Ala Lys Ser Asp Ile Phe Asp
225                 230                 235                 240

Ser Asp Ser Pro His Tyr Ala Asp Gly Val His Ser Ser Leu Leu Glu
                245                 250                 255

Ala Gly Asp Ser Ser Tyr Val Phe Glu Pro Asp Gln Ser Asp Leu Ser
            260                 265                 270

Gln Asp Glu Glu Asp Asn Phe Ser Lys Ser Leu Leu Pro Pro Tyr Val
        275                 280                 285

Phe Pro Lys Leu Glu Asp Asp Asp Tyr Ser Asp Pro Pro Ala Ser Phe
290                 295                 300

Glu Asp His Ala Phe Trp Ser Trp Ser Tyr
                305                 310
```

```
305              310
```

<210> SEQ ID NO 42
<211> LENGTH: 954
<212> TYPE: DNA
<213> ORGANISM: Populus tremuloides

<400> SEQUENCE: 42

```
atggcggctt gtggtggtgg tggtggtggt tctaatccca atttgtctgt tttagttcaa    60
agccaaagag gcccttgtgc tgcttctcaa cctcttgaag cttttttcct ttctggctct   120
tctccttctt tcttggttc aagatccatg atgagttttg cagatgttca ccaagcaaat    180
ggatcaacta gaccgtttt ccgcccatat gatcacgaag acaacggcga cgatgatttg    240
gatgaatatt tcatcaacc tgaaaagaag aggagactta ctgttgatca agttcagttt    300
cttgaaagaa gttttgaggt tgagaacaag cttgaacccg aaaggaaaat ccagctggcg    360
aaggatcttg gcttgcagcc tcggcaggtt gccatatggt ttcaaaaccg ccgggcaaga    420
tggaagacga aacagcttga aaaagattat gaggttctgc aatctagcta caatggcctt    480
aaggctgact acgacaacct cttcaaggag aaggagaaac taaaagctga ggttaatctt    540
ctcaccaacg agttgctcct taaagagaaa gagaaaggaa gctcagaatt gtctgataaa    600
gatgcattat ctcaagagcc acccaaaaag gcaatagccg attcagcttc agagggtgaa    660
gtgtcgaaaa cttcaaccgt ggcctgccag caggaagata ttagctcagc caaaagtgat    720
atgtttgatt cagacagccc acattttgcg gatggggtac attcctcact cttagaggca    780
ggtgattctt cacatgtctt cgagcccgac caatcggatt tatcacaaga tgaagaagat    840
aacttgagca agagtctttt gcctccgtac gtctttccaa gcttgaaga tggtgattac    900
tctgacccgc cagcaagttt tgaagatcat gccttttggt gctggtcata ctaa          954
```

<210> SEQ ID NO 43
<211> LENGTH: 317
<212> TYPE: PRT
<213> ORGANISM: Populus tremuloides

<400> SEQUENCE: 43

```
Met Ala Ala Cys Gly Gly Gly Gly Gly Ser Asn Pro Asn Leu Ser
1               5                  10                  15

Val Leu Val Gln Ser Gln Arg Gly Pro Cys Ala Ala Ser Gln Pro Leu
            20                  25                  30

Glu Ala Phe Phe Leu Ser Gly Ser Ser Pro Ser Phe Leu Gly Ser Arg
        35                  40                  45

Ser Met Met Ser Phe Ala Asp Val His Gln Ala Asn Gly Ser Thr Arg
    50                  55                  60

Pro Phe Phe Arg Pro Tyr Asp His Glu Asp Asn Gly Asp Asp Asp Leu
65                  70                  75                  80

Asp Glu Tyr Phe His Gln Pro Glu Lys Lys Arg Arg Leu Thr Val Asp
                85                  90                  95

Gln Val Gln Phe Leu Glu Arg Ser Phe Glu Val Glu Asn Lys Leu Glu
            100                 105                 110

Pro Glu Arg Lys Ile Gln Leu Ala Lys Asp Leu Gly Leu Gln Pro Arg
        115                 120                 125

Gln Val Ala Ile Trp Phe Gln Asn Arg Arg Ala Arg Trp Lys Thr Lys
    130                 135                 140

Gln Leu Glu Lys Asp Tyr Glu Val Leu Gln Ser Ser Tyr Asn Gly Leu
145                 150                 155                 160
```

```
Lys Ala Asp Tyr Asp Asn Leu Phe Lys Glu Lys Glu Lys Leu Lys Ala
                165                 170                 175

Glu Val Asn Leu Leu Thr Asn Glu Leu Leu Lys Glu Lys Glu Lys
            180                 185                 190

Gly Ser Ser Glu Leu Ser Asp Lys Asp Ala Leu Ser Gln Glu Pro Pro
            195                 200                 205

Lys Lys Ala Ile Ala Asp Ser Ala Ser Glu Gly Glu Val Ser Lys Thr
        210                 215                 220

Ser Thr Val Ala Cys Gln Gln Glu Asp Ile Ser Ser Ala Lys Ser Asp
225                 230                 235                 240

Met Phe Asp Ser Asp Ser Pro His Phe Ala Asp Gly Val His Ser Ser
                245                 250                 255

Leu Leu Glu Ala Gly Asp Ser Ser His Val Phe Glu Pro Asp Gln Ser
            260                 265                 270

Asp Leu Ser Gln Asp Glu Glu Asp Asn Leu Ser Lys Ser Leu Leu Pro
        275                 280                 285

Pro Tyr Val Phe Pro Lys Leu Glu Asp Gly Asp Tyr Ser Asp Pro Pro
        290                 295                 300

Ala Ser Phe Glu Asp His Ala Phe Trp Cys Trp Ser Tyr
305                 310                 315
```

<210> SEQ ID NO 44
<211> LENGTH: 909
<212> TYPE: DNA
<213> ORGANISM: Populus tremuloides

<400> SEQUENCE: 44

```
atggcgggtg ataaagactg tggcagttct aaaatgacca tttttcttcg aaacggcagg    60
ctccctcctt gtgaatctct ctgtattctc acctctttta gcactcttca tggtgcaaaa   120
tctatggtta attttaggaa tgatggagga gacactgtag acatgtcttt tttccaacca   180
catgtcaaag aagaagtag cgatgaggat tatgatgcgc accttaagcc atctgaaaag   240
aaaaggcggc ttacagctgc tcaagtccag tttcttgaga gagctttga ggcggagaat   300
aagcttgaac cagagaggaa gatgcagctt gctaaagaac tcggcttgca gcctcgccag   360
gttgcaatat ggtttcaaaa ccgtagagct cggttcaaga caagcagct ggaagggac    420
tacgactcct tgagaatcag cttttgacaaa ctcaaggctg attatgacaa actcctcctc   480
gagaagcaga atttgaaaaa cgagcttctt tcactgaaag aaaaattgct tagcagagag   540
gaaagtatgg aaagttcaga accattttgat gtcatccatt caccggatgc agaacttgag   600
cctattcctg atacagtgtc tgaaaatgtt tccgccattg tgccaatggt gacacccaaa   660
caagaagaaa gttcagctaa aatgatgtt ttcaactcag acagcccacg ttcatttttg    720
gagccccgtg attgttatcg tgttttcgag tcagaccaac cagattttc ccaagttgaa    780
gaagataatc tcaccaggag ctttctaccc cctccgtact ttccaaaact ctaccgagag   840
ccacctgcaa gttcacgtaa ttttgaattc tcagcggaag atcagccctt tggtcctgg    900
atttactga                                                            909
```

<210> SEQ ID NO 45
<211> LENGTH: 302
<212> TYPE: PRT
<213> ORGANISM: Populus tremuloides

<400> SEQUENCE: 45

```
Met Ala Gly Asp Lys Asp Cys Gly Ser Ser Lys Met Thr Ile Phe Leu
1               5                   10                  15
```

```
Arg Asn Gly Arg Leu Pro Pro Cys Glu Ser Leu Cys Ile Leu Thr Ser
            20                  25                  30

Phe Ser Thr Leu His Gly Ala Lys Ser Met Val Asn Phe Arg Asn Asp
        35                  40                  45

Gly Gly Asp Thr Val Asp Met Ser Phe Phe Gln Pro His Val Lys Glu
 50                  55                  60

Glu Ser Ser Asp Glu Asp Tyr Asp Ala His Leu Lys Pro Ser Glu Lys
 65                  70                  75                  80

Lys Arg Arg Leu Thr Ala Ala Gln Val Gln Phe Leu Glu Lys Ser Phe
                85                  90                  95

Glu Ala Glu Asn Lys Leu Glu Pro Glu Arg Lys Met Gln Leu Ala Lys
            100                 105                 110

Glu Leu Gly Leu Gln Pro Arg Gln Val Ala Ile Trp Phe Gln Asn Arg
        115                 120                 125

Arg Ala Arg Phe Lys Asn Lys Gln Leu Glu Arg Asp Tyr Asp Ser Leu
130                 135                 140

Arg Ile Ser Phe Asp Lys Leu Lys Ala Asp Tyr Asp Lys Leu Leu Leu
145                 150                 155                 160

Glu Lys Gln Asn Leu Lys Asn Glu Leu Leu Ser Leu Lys Glu Lys Leu
                165                 170                 175

Leu Ser Arg Glu Glu Ser Met Glu Ser Ser Glu Pro Phe Asp Val Ile
            180                 185                 190

His Ser Pro Asp Ala Glu Leu Glu Pro Ile Pro Asp Thr Val Ser Glu
        195                 200                 205

Asn Val Ser Ala Ile Val Pro Met Val Thr Pro Lys Gln Glu Glu Ser
210                 215                 220

Ser Ala Lys Asn Asp Val Phe Asn Ser Asp Ser Pro Arg Ser Phe Leu
225                 230                 235                 240

Glu Pro Arg Asp Cys Tyr Arg Val Phe Glu Ser Asp Gln Pro Asp Phe
                245                 250                 255

Ser Gln Val Glu Glu Asp Asn Leu Thr Arg Ser Phe Leu Pro Pro Pro
            260                 265                 270

Tyr Phe Pro Lys Leu Tyr Arg Glu Pro Pro Ala Ser Ser Arg Asn Phe
        275                 280                 285

Glu Phe Ser Ala Glu Asp Gln Pro Phe Trp Ser Trp Ile Tyr
290                 295                 300

<210> SEQ ID NO 46
<211> LENGTH: 975
<212> TYPE: DNA
<213> ORGANISM: Medicago truncatula

<400> SEQUENCE: 46
atggcaggtg gcaagctttt tggtggttct aatatgtcac ttttgcttca aaatgaaaga    60
ctcccttgta cttctgaagt ccttgaatct ctttgggttc acacccctgc ttcttttcaa   120
ggttcaaatt cagtggttaa ttttgagaat ggtggtggta gcaacagagt ggtaacagat   180
agacccttct ttcaacaact tgagaaagaa gagaattgtg gtgatgaaga ttatgaagca   240
tgctaccatc aacaaggaaa gaaaggagg ctttcaagtg aacaagttca atttcttgaa   300
agagtttttg aggtagaaaa caagcttgaa cctgatagga agttcaact tgcaaaagag   360 cttggttttgc aaccaagaca agttgctata tggtttcaaa acagaagggc aaggttcaaa   420
actaaacagc ttgaaaaga ttatggcaca ttgaaagcta gctttgatag tctcaaagat   480
gattatgata atcttcttca agagaatgac aagttaaaag aagaggtgaa ttctctcaag   540
```

-continued

```
aacaaattga tcccaagaga taaagaaaaa gtgaattcag aagacaaatc atcaccagaa    600
gcaatcaatt cacctcataa caacatagat ccatggata taatttcaat tacaaattca    660
gaaaatgggt ccaaaatgtc actccctaat atggtactaa aatgtaagca agaagatgcc    720
aattcagcta aaagtgatgt gcttgattct gatagcccac attgcaatga tgggaacaat    780
ctttcttctt tcatagagcc tacagattca gatttctcac aagatgaaga ggataatgat    840
aacttgagtc ataatctttt gactcttcct tgcttaccaa aagttgaaga tgtttgctat    900
gatgacccac atgaaaattc ttgtaatttt gggttccctg ttgaagatca aaccttttgt    960
ttctggcctt attga                                                     975
```

<210> SEQ ID NO 47
<211> LENGTH: 324
<212> TYPE: PRT
<213> ORGANISM: Medicago truncatula

<400> SEQUENCE: 47

```
Met Ala Gly Gly Lys Leu Phe Gly Gly Ser Asn Met Ser Leu Leu
1               5                   10                  15

Gln Asn Glu Arg Leu Pro Cys Thr Ser Glu Val Leu Glu Ser Leu Trp
            20                  25                  30

Val His Thr Pro Ala Ser Phe Gln Gly Ser Asn Ser Val Val Asn Phe
        35                  40                  45

Glu Asn Gly Gly Gly Ser Asn Arg Val Val Thr Asp Arg Pro Phe Phe
    50                  55                  60

Gln Gln Leu Glu Lys Glu Asn Cys Gly Asp Glu Asp Tyr Glu Ala
65                  70                  75                  80

Cys Tyr His Gln Gln Gly Lys Lys Arg Arg Leu Ser Ser Glu Gln Val
                85                  90                  95

Gln Phe Leu Glu Lys Ser Phe Glu Val Glu Asn Lys Leu Glu Pro Asp
            100                 105                 110

Arg Lys Val Gln Leu Ala Lys Glu Leu Gly Leu Gln Pro Arg Gln Val
        115                 120                 125

Ala Ile Trp Phe Gln Asn Arg Arg Ala Arg Phe Lys Thr Lys Gln Leu
    130                 135                 140

Glu Lys Asp Tyr Gly Thr Leu Lys Ala Ser Phe Asp Ser Leu Lys Asp
145                 150                 155                 160

Asp Tyr Asp Asn Leu Leu Gln Glu Asn Asp Lys Leu Lys Glu Val
                165                 170                 175

Asn Ser Leu Lys Asn Lys Leu Ile Pro Arg Asp Lys Glu Lys Val Asn
            180                 185                 190

Ser Glu Asp Lys Ser Ser Pro Glu Ala Ile Asn Ser Pro His Asn Asn
        195                 200                 205

Ile Asp Pro Met Asp Ile Ile Ser Ile Thr Asn Ser Glu Asn Gly Ser
    210                 215                 220

Lys Met Ser Leu Pro Asn Met Val Leu Lys Cys Lys Gln Glu Asp Ala
225                 230                 235                 240

Asn Ser Ala Lys Ser Asp Val Leu Asp Ser Asp Ser Pro His Cys Asn
                245                 250                 255

Asp Gly Asn Asn Leu Ser Ser Phe Ile Glu Pro Thr Asp Ser Asp Phe
            260                 265                 270

Ser Gln Asp Glu Glu Asp Asn Asp Asn Leu Ser His Asn Leu Leu Thr
        275                 280                 285

Leu Pro Cys Leu Pro Lys Val Glu Asp Val Cys Tyr Asp Asp Pro His
```

```
                290                 295                 300
Glu Asn Ser Cys Asn Phe Gly Phe Pro Val Glu Asp Gln Thr Phe Cys
305                 310                 315                 320

Phe Trp Pro Tyr

<210> SEQ ID NO 48
<211> LENGTH: 984
<212> TYPE: DNA
<213> ORGANISM: Phaseolus vulgaris

<400> SEQUENCE: 48
atggcgggtg gcaagcttca tcctggttca aacatgtcac ttctcctcca aaacgacagg      60
ctcccttgct cctctgaagt ccttgagtct ctttgggctc acacctctaa cgctgcttcc     120
ttccaaggtt caaaatctat ggttgatttt gagaatgtta gtgggggcag ggtgacggat     180
aggccctttt ttcaagcgtt ggagaaggaa gataactgtg atgatgatta tgagggttgc     240
ttccatcaac cgggtaagaa aaggaggctc acaagcgaac aagttcagtt ccttgaaagg     300
aactttgagg tcgagaacaa gcttgaacct gaaaggaagg tccaacttgc aaaggagctt     360
ggcttgcagc caaggcaagt ggctatatgg ttccaaaacc gaagggcaag gttcaagacc     420
aagcagctag aaaaagatta tggcacattg aaagctagct atgacagact caaaggtgac     480
tatgaaagtc ttcttcaaga gaatgacaag ttaaaagcag aggtgaattc tctggagagc     540
aaattgattc ttagagataa agagaaggag aattcggacg acaagtcatc tcctgatgct     600
gtcaattcac cccacaaaga gcctatggat ttaatttcaa attcaacatc tgaaaatggg     660
accaaagtgt cactccctat tatggtaaca tgcaagcaag aagatgccaa ttcagccaaa     720
agtgatgtgc ttgattcgga cagcccacat tgcactgatg ggaaccatcc ctcttcattc     780
gtggagcctg ctgattcctc ccatgctttt gaaccagacc actccgactt ctcccaagat     840
gaagaggata tcttagtga aagccttttg accctccctt gcttaccaaa ggttgaagaa     900
gcctgctatg atgaccctcc tgaaaaccct tgtaattttg gcttccatgt cgaggatcaa     960
accttctgtt tctggcccta ttga                                           984

<210> SEQ ID NO 49
<211> LENGTH: 327
<212> TYPE: PRT
<213> ORGANISM: Phaseolus vulgaris

<400> SEQUENCE: 49

Met Ala Gly Gly Lys Leu His Pro Gly Ser Asn Met Ser Leu Leu Leu
1               5                  10                  15

Gln Asn Asp Arg Leu Pro Cys Ser Ser Glu Val Leu Glu Ser Leu Trp
            20                  25                  30

Ala His Thr Ser Asn Ala Ala Ser Phe Gln Gly Ser Lys Ser Met Val
        35                  40                  45

Asp Phe Glu Asn Val Ser Gly Gly Arg Val Thr Asp Arg Pro Phe Phe
    50                  55                  60

Gln Ala Leu Glu Lys Glu Asp Asn Cys Asp Asp Asp Tyr Glu Gly Cys
65                  70                  75                  80

Phe His Gln Pro Gly Lys Lys Arg Arg Leu Thr Ser Glu Gln Val Gln
                85                  90                  95

Phe Leu Glu Arg Asn Phe Glu Val Glu Asn Lys Leu Glu Pro Glu Arg
            100                 105                 110

Lys Val Gln Leu Ala Lys Glu Leu Gly Leu Gln Pro Arg Gln Val Ala
        115                 120                 125
```

```
Ile Trp Phe Gln Asn Arg Arg Ala Arg Phe Lys Thr Lys Gln Leu Glu
    130                 135                 140
Lys Asp Tyr Gly Thr Leu Lys Ala Ser Tyr Asp Arg Leu Lys Gly Asp
145                 150                 155                 160
Tyr Glu Ser Leu Leu Gln Glu Asn Asp Lys Leu Lys Ala Glu Val Asn
                165                 170                 175
Ser Leu Glu Ser Lys Leu Ile Leu Arg Asp Lys Glu Lys Glu Asn Ser
            180                 185                 190
Asp Asp Lys Ser Ser Pro Asp Ala Val Asn Ser Pro His Lys Glu Pro
        195                 200                 205
Met Asp Leu Ile Ser Asn Ser Thr Ser Glu Asn Gly Thr Lys Val Ser
    210                 215                 220
Leu Pro Ile Met Val Thr Cys Lys Gln Glu Asp Ala Asn Ser Ala Lys
225                 230                 235                 240
Ser Asp Val Leu Asp Ser Asp Ser Pro His Cys Thr Asp Gly Asn His
                245                 250                 255
Pro Ser Ser Phe Val Glu Pro Ala Asp Ser Ser His Ala Phe Glu Pro
            260                 265                 270
Asp His Ser Asp Phe Ser Gln Asp Glu Glu Asp Asn Leu Ser Glu Ser
        275                 280                 285
Leu Leu Thr Leu Pro Cys Leu Pro Lys Val Glu Glu Ala Cys Tyr Asp
    290                 295                 300
Asp Pro Pro Glu Asn Pro Cys Asn Phe Gly Phe His Val Glu Asp Gln
305                 310                 315                 320
Thr Phe Cys Phe Trp Pro Tyr
                325
```

<210> SEQ ID NO 50  
<211> LENGTH: 957  
<212> TYPE: DNA  
<213> ORGANISM: Lotus corniculatus

<400> SEQUENCE: 50

```
atggcgggag ggagggtctt tagcggcggt tctgctgctc ctgcaaatgt tccgatacc      60
agtcttttgc ttcagaatca acctcctgat tcttctctct cctctctac ctctgcttct   120
tttctcggtt caagatccat ggtgagcttc gcagataata aattagggca acgcgtcg    180
ttcttctccg cgtttgacct cgatgagaac ggcgatgagg tcatggacga gtactttcac   240
caatcggaga agaagcgccg tctctctgtt gaccaagttc agtttctgga aagagcttc    300
gaggtggata caagctcga acctgacagg aaaaccaaga ttgccaagga ccttggtttg    360
cagccacgcc aagtcgcaat ctggttccag aaccgccgtg cacggtggaa gacgaaacag   420
cttgagaagg attatgattc tctgcatagt agctttgaga gtctcaaatc aactatgat    480
aatcttctca aggagaaaga catgttaaaa gctgaggtgg caagtctcac tgagaaggtg   540
cttgcaagag agaatttgaa acaagttgaa agtgaaacaa agggattggt tgaaccaccc   600
caaaggcctt tacttgattc agtttcagag ggtgaagaat ctaaagtctc tgttggggct   660
tgtaaacatg aggatatcag ttcagccagg agtgagagtt tggattctga tagcccacgt   720
tacaggggat gatatggagt taactcagca gtgctagaga catgtgattc ttcttatgtg   780
gttgaacctg atcaatcgga tatgtcacag gatgaggaag acaacctgac aagaccctg    840
ttgcctccat acatgttttc caaacttgga gatatggatt actccgaccc gcctgaaagt   900
tcatgtaatt tcggatttcc ggaggaagat catgcccttt ggtcatggtc ttactga      957
```

<210> SEQ ID NO 51
<211> LENGTH: 318
<212> TYPE: PRT
<213> ORGANISM: Lotus corniculatus

<400> SEQUENCE: 51

Met Ala Gly Gly Arg Val Phe Ser Gly Gly Ser Ala Ala Pro Ala Asn
1               5                   10                  15

Val Ser Asp Thr Ser Leu Leu Gln Asn Gln Pro Pro Asp Ser Ser
            20                  25                  30

Leu Phe Leu Ser Thr Ser Ala Ser Phe Leu Gly Ser Arg Ser Met Val
        35                  40                  45

Ser Phe Ala Asp Asn Lys Leu Gly Gln Thr Arg Ser Phe Phe Ser Ala
    50                  55                  60

Phe Asp Leu Asp Glu Asn Gly Asp Glu Val Met Asp Glu Tyr Phe His
65                  70                  75                  80

Gln Ser Glu Lys Lys Arg Arg Leu Ser Val Asp Gln Val Gln Phe Leu
                85                  90                  95

Glu Lys Ser Phe Glu Val Asp Asn Lys Leu Glu Pro Asp Arg Lys Thr
            100                 105                 110

Lys Ile Ala Lys Asp Leu Gly Leu Gln Pro Arg Gln Val Ala Ile Trp
        115                 120                 125

Phe Gln Asn Arg Arg Ala Arg Trp Lys Thr Lys Gln Leu Glu Lys Asp
    130                 135                 140

Tyr Asp Ser Leu His Ser Ser Phe Glu Ser Leu Lys Ser Asn Tyr Asp
145                 150                 155                 160

Asn Leu Leu Lys Glu Lys Asp Met Leu Lys Ala Glu Val Ala Ser Leu
                165                 170                 175

Thr Glu Lys Val Leu Ala Arg Glu Asn Leu Lys Gln Val Glu Ser Glu
            180                 185                 190

Thr Lys Gly Leu Val Glu Pro Pro Gln Arg Pro Leu Leu Asp Ser Val
        195                 200                 205

Ser Glu Gly Glu Glu Ser Lys Val Ser Val Gly Ala Cys Lys His Glu
    210                 215                 220

Asp Ile Ser Ser Ala Arg Ser Glu Ser Leu Asp Ser Asp Ser Pro Arg
225                 230                 235                 240

Tyr Arg Asp Gly Tyr Gly Val Asn Ser Ala Val Leu Glu Thr Cys Asp
                245                 250                 255

Ser Ser Tyr Val Val Glu Pro Asp Gln Ser Asp Met Ser Gln Asp Glu
            260                 265                 270

Glu Asp Asn Leu Thr Lys Thr Leu Leu Pro Pro Tyr Met Phe Ser Lys
        275                 280                 285

Leu Gly Asp Met Asp Tyr Ser Asp Pro Pro Glu Ser Ser Cys Asn Phe
    290                 295                 300

Gly Phe Pro Glu Glu Asp His Ala Leu Trp Ser Trp Ser Tyr
305                 310                 315

<210> SEQ ID NO 52
<211> LENGTH: 2194
<212> TYPE: DNA
<213> ORGANISM: Oryza sativa

<400> SEQUENCE: 52
aatccgaaaa gtttctgcac cgttttcacc ccctaactaa caatataggg aacgtgtgct      60
aaatataaaa tgagaccttt tatatgtagc gctgataact agaactatgc aagaaaaact     120

```
catccaccta ctttagtggc aatcgggcta aataaaaaag agtcgctaca ctagtttcgt      180
tttccttagt aattaagtgg gaaaatgaaa tcattattgc ttagaatata cgttcacatc      240
tctgtcatga agttaaatta ttcgaggtag ccataattgt catcaaactc ttcttgaata      300
aaaaaatctt tctagctgaa ctcaatgggt aaagagagag attttttta aaaaaataga      360
atgaagatat tctgaacgta ttggcaaaga tttaaacata taattatata attttatagt      420
ttgtgcattc gtcatatcgc acatcattaa ggacatgtct tactccatcc caattttat       480
ttagtaatta aagacaattg acttatttt  attatttatc ttttttcgat tagatgcaag      540
gtacttacgc acacactttg tgctcatgtg catgtgtgag tgcacctcct caatacacgt      600
tcaactagca acacatctct aatatcactc gcctatttaa tacatttagg tagcaatatc      660
tgaattcaag cactccacca tcaccagacc acttttaata atatctaaaa tacaaaaaat      720
aattttacag aatagcatga aaagtatgaa acgaactatt taggttttc  acatacaaaa      780
aaaaaaagaa tttgctcgt  gcgcgagcgc caatctccca tattgggcac acaggcaaca      840
acagagtggc tgcccacaga acaacccaca aaaaacgatg atctaacgga ggacagcaag      900
tccgcaacaa ccttttaaca gcaggctttg cggccaggag agaggaggag aggcaaagaa      960
aaccaagcat cctccttctc ccatctataa attcctcccc ccttttcccc tctctatata     1020
ggaggcatcc aagccaagaa gagggagagc accaaggaca cgcgactagc agaagccgag     1080
cgaccgcctt ctcgatccat atcttccggt cgagttcttg gtcgatctct tccctcctcc     1140
acctcctcct cacagggtat gtgcctccct tcggttgttc ttggatttat tgttctaggt     1200
tgtgtagtac gggcgttgat gttaggaaag gggatctgta tctgtgatga ttcctgttct     1260
tggatttggg atagaggggt tcttgatgtt gcatgttatc ggttcggttt gattagtagt     1320
atggttttca atcgtctgga gagctctatg gaaatgaaat ggtttaggga tcggaatctt     1380
gcgattttgt gagtaccttt tgtttgaggt aaaatcagag caccggtgat tttgcttggt     1440
gtaataaagt acgttgttt  ggtcctcgat tctggtagtg atgcttctcg atttgacgaa     1500
gctatccttt gtttattccc tattgaacaa aaataatcca actttgaaga cggtcccgtt     1560
gatgagattg aatgattgat tcttaagcct gtccaaaatt tcgcagctgg cttgtttaga     1620
tacagtagtc cccatcacga aattcatgga aacagttata atcctcagga acaggggatt     1680
ccctgttctt ccgatttgct ttagtcccag aatttttttt cccaaatatc ttaaaaagtc     1740
actttctggt tcagttcaat gaattgattg ctacaaataa tgcttttata gcgttatcct     1800
agctgtagtt cagttaatag gtaataccc  tatagtttag tcaggagaag aacttatccg     1860
atttctgatc tccatttta  attatatgaa atgaactgta gcataagcag tattcatttg     1920
gattatttt  tttattagct ctcacccctt cattattctg agctgaaagt ctggcatgaa     1980
ctgtcctcaa ttttgttttc aaattcacat cgattatcta tgcattatcc tcttgtatct     2040
acctgtagaa gttctttttt ggttattcct tgactgcttg attacagaaa gaaatttatg     2100
aagctgtaat cgggatagtt atactgcttg ttcttatgat tcatttcctt tgtgcagttc     2160
ttggtgtagc ttgccacttt caccagcaaa gttc                                 2194
```

<210> SEQ ID NO 53
<211> LENGTH: 101
<212> TYPE: PRT
<213> ORGANISM: Artificial Sequence
<220> FEATURE:
<223> OTHER INFORMATION: Figure 1 Consensus Sequence
<220> FEATURE:
<221> NAME/KEY: misc_feature
<222> LOCATION: (13)..(13)

-continued

```
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (69)..(69)
<223> OTHER INFORMATION: Xaa can be any naturally occurring amino acid
<220> FEATURE:
<221> NAME/KEY: misc_feature
<222> LOCATION: (86)..(86)
<223> OTHER INFORMATION: Xaa can be any naturally occurring amino acid

<400> SEQUENCE: 53

Pro Glu Lys Lys Arg Arg Leu Thr Ala Glu Gln Val Xaa Leu Leu Glu
1               5                   10                  15

Arg Ser Phe Glu Glu Asn Lys Leu Glu Pro Glu Arg Lys Thr Xaa
            20                  25                  30

Leu Ala Arg Lys Leu Gly Leu Gln Pro Arg Gln Val Ala Val Trp Phe
        35                  40                  45

Gln Asn Arg Arg Ala Arg Trp Lys Thr Lys Thr Lys Gln Leu Glu
    50                  55                  60

Arg Asp Tyr Asp Xaa Leu Lys Ala Ser Tyr Asp Ala Leu Arg Ala Asp
65              70                  75                  80

Tyr Asp Ala Leu Leu Xaa Asp Asn Asp Lys Leu Arg Ala Glu Val Val
            85                  90                  95

Ser Leu Thr Glu Lys
            100

<210> SEQ ID NO 54
<211> LENGTH: 404
<212> TYPE: PRT
<213> ORGANISM: Artificial Sequence
<220> FEATURE:
<223> OTHER INFORMATION: Figure 2 Consensus Sequence
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(7)
<223> OTHER INFORMATION: Xaa can be any naturally occurring amino acid
<220> FEATURE:
<221> NAME/KEY: misc_feature
<222> LOCATION: (9)..(41)
<223> OTHER INFORMATION: Xaa can be any naturally occurring amino acid
<220> FEATURE:
<221> NAME/KEY: misc_feature
<222> LOCATION: (43)..(49)
<223> OTHER INFORMATION: Xaa can be any naturally occurring amino acid
<220> FEATURE:
<221> NAME/KEY: misc_feature
<222> LOCATION: (51)..(57)
<223> OTHER INFORMATION: Xaa can be any naturally occurring amino acid
<220> FEATURE:
<221> NAME/KEY: misc_feature
<222> LOCATION: (59)..(62)
<223> OTHER INFORMATION: Xaa can be any naturally occurring amino acid
<220> FEATURE:
<221> NAME/KEY: misc_feature
<222> LOCATION: (64)..(77)
<223> OTHER INFORMATION: Xaa can be any naturally occurring amino acid
<220> FEATURE:
<221> NAME/KEY: misc_feature
<222> LOCATION: (82)..(87)
<223> OTHER INFORMATION: Xaa can be any naturally occurring amino acid
<220> FEATURE:
<221> NAME/KEY: misc_feature
<222> LOCATION: (89)..(91)
<223> OTHER INFORMATION: Xaa can be any naturally occurring amino acid
```

```
<220> FEATURE:
<221> NAME/KEY: misc_feature
<222> LOCATION: (94)..(94)
<223> OTHER INFORMATION: Xaa can be any naturally occurring amino acid
<220> FEATURE:
<221> NAME/KEY: misc_feature
<222> LOCATION: (98)..(102)
<223> OTHER INFORMATION: Xaa can be any naturally occurring amino acid
<220> FEATURE:
<221> NAME/KEY: misc_feature
<222> LOCATION: (110)..(110)
<223> OTHER INFORMATION: Xaa can be any naturally occurring amino acid
<220> FEATURE:
<221> NAME/KEY: misc_feature
<222> LOCATION: (115)..(115)
<223> OTHER INFORMATION: Xaa can be any naturally occurring amino acid
<220> FEATURE:
<221> NAME/KEY: misc_feature
<222> LOCATION: (122)..(122)
<223> OTHER INFORMATION: Xaa can be any naturally occurring amino acid
<220> FEATURE:
<221> NAME/KEY: misc_feature
<222> LOCATION: (132)..(132)
<223> OTHER INFORMATION: Xaa can be any naturally occurring amino acid
<220> FEATURE:
<221> NAME/KEY: misc_feature
<222> LOCATION: (137)..(137)
<223> OTHER INFORMATION: Xaa can be any naturally occurring amino acid
<220> FEATURE:
<221> NAME/KEY: misc_feature
<222> LOCATION: (163)..(163)
<223> OTHER INFORMATION: Xaa can be any naturally occurring amino acid
<220> FEATURE:
<221> NAME/KEY: misc_feature
<222> LOCATION: (167)..(167)
<223> OTHER INFORMATION: Xaa can be any naturally occurring amino acid
<220> FEATURE:
<221> NAME/KEY: misc_feature
<222> LOCATION: (170)..(170)
<223> OTHER INFORMATION: Xaa can be any naturally occurring amino acid
<220> FEATURE:
<221> NAME/KEY: misc_feature
<222> LOCATION: (174)..(174)
<223> OTHER INFORMATION: Xaa can be any naturally occurring amino acid
<220> FEATURE:
<221> NAME/KEY: misc_feature
<222> LOCATION: (176)..(177)
<223> OTHER INFORMATION: Xaa can be any naturally occurring amino acid
<220> FEATURE:
<221> NAME/KEY: misc_feature
<222> LOCATION: (181)..(181)
<223> OTHER INFORMATION: Xaa can be any naturally occurring amino acid
<220> FEATURE:
<221> NAME/KEY: misc_feature
<222> LOCATION: (184)..(184)
<223> OTHER INFORMATION: Xaa can be any naturally occurring amino acid
<220> FEATURE:
<221> NAME/KEY: misc_feature
<222> LOCATION: (187)..(188)
<223> OTHER INFORMATION: Xaa can be any naturally occurring amino acid
<220> FEATURE:
<221> NAME/KEY: misc_feature
<222> LOCATION: (190)..(190)
<223> OTHER INFORMATION: Xaa can be any naturally occurring amino acid
<220> FEATURE:
<221> NAME/KEY: misc_feature
<222> LOCATION: (194)..(194)
<223> OTHER INFORMATION: Xaa can be any naturally occurring amino acid
<220> FEATURE:
<221> NAME/KEY: misc_feature
<222> LOCATION: (202)..(202)
<223> OTHER INFORMATION: Xaa can be any naturally occurring amino acid
<220> FEATURE:
<221> NAME/KEY: misc_feature
<222> LOCATION: (205)..(277)
<223> OTHER INFORMATION: Xaa can be any naturally occurring amino acid
<220> FEATURE:
<221> NAME/KEY: misc_feature
<222> LOCATION: (279)..(279)
<223> OTHER INFORMATION: Xaa can be any naturally occurring amino acid
```

```
<220> FEATURE:
<221> NAME/KEY: misc_feature
<222> LOCATION: (282)..(283)
<223> OTHER INFORMATION: Xaa can be any naturally occurring amino acid
<220> FEATURE:
<221> NAME/KEY: misc_feature
<222> LOCATION: (285)..(285)
<223> OTHER INFORMATION: Xaa can be any naturally occurring amino acid
<220> FEATURE:
<221> NAME/KEY: misc_feature
<222> LOCATION: (287)..(289)
<223> OTHER INFORMATION: Xaa can be any naturally occurring amino acid
<220> FEATURE:
<221> NAME/KEY: misc_feature
<222> LOCATION: (291)..(291)
<223> OTHER INFORMATION: Xaa can be any naturally occurring amino acid
<220> FEATURE:
<221> NAME/KEY: misc_feature
<222> LOCATION: (293)..(293)
<223> OTHER INFORMATION: Xaa can be any naturally occurring amino acid
<220> FEATURE:
<221> NAME/KEY: misc_feature
<222> LOCATION: (295)..(295)
<223> OTHER INFORMATION: Xaa can be any naturally occurring amino acid
<220> FEATURE:
<221> NAME/KEY: misc_feature
<222> LOCATION: (297)..(297)
<223> OTHER INFORMATION: Xaa can be any naturally occurring amino acid
<220> FEATURE:
<221> NAME/KEY: misc_feature
<222> LOCATION: (299)..(315)
<223> OTHER INFORMATION: Xaa can be any naturally occurring amino acid
<220> FEATURE:
<221> NAME/KEY: misc_feature
<222> LOCATION: (318)..(345)
<223> OTHER INFORMATION: Xaa can be any naturally occurring amino acid
<220> FEATURE:
<221> NAME/KEY: misc_feature
<222> LOCATION: (347)..(347)
<223> OTHER INFORMATION: Xaa can be any naturally occurring amino acid
<220> FEATURE:
<221> NAME/KEY: misc_feature
<222> LOCATION: (351)..(370)
<223> OTHER INFORMATION: Xaa can be any naturally occurring amino acid
<220> FEATURE:
<221> NAME/KEY: misc_feature
<222> LOCATION: (372)..(396)
<223> OTHER INFORMATION: Xaa can be any naturally occurring amino acid
<220> FEATURE:
<221> NAME/KEY: misc_feature
<222> LOCATION: (398)..(403)
<223> OTHER INFORMATION: Xaa can be any naturally occurring amino acid

<400> SEQUENCE: 54

Met Xaa Xaa Gly Xaa Xaa Xaa Phe Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Gly Xaa Xaa Xaa Xaa Xaa Xaa
        35                  40                  45

Xaa Gly Xaa Xaa Xaa Xaa Xaa Xaa Ser Xaa Xaa Xaa Xaa Glu Xaa
    50                  55                  60

Xaa Xaa Xaa Xaa Xaa Xaa Xaa Xaa Xaa Xaa Xaa Xaa Arg Pro Phe
65                  70                  75                  80

Phe Xaa Xaa Xaa Xaa Xaa Xaa Glu Xaa Xaa Xaa Glu Glu Xaa Tyr Asp
                85                  90                  95

Glu Xaa Xaa Xaa Xaa Xaa Glu Lys Lys Arg Arg Leu Thr Xaa Glu Gln
            100                 105                 110

Val Gln Xaa Leu Glu Lys Ser Phe Glu Xaa Glu Asn Lys Leu Glu Pro
        115                 120                 125

Glu Arg Lys Xaa Gln Leu Ala Lys Xaa Leu Gly Leu Gln Pro Arg Gln
```

-continued

```
                130                 135                 140
Val Ala Val Trp Phe Gln Asn Arg Arg Ala Arg Trp Lys Thr Lys Gln
145                 150                 155                 160

Leu Glu Xaa Asp Tyr Asp Xaa Leu Lys Xaa Ser Tyr Asp Xaa Leu Xaa
                165                 170                 175

Xaa Asp Tyr Asp Xaa Leu Leu Xaa Glu Asn Xaa Xaa Leu Xaa Ala Glu
                180                 185                 190

Val Xaa Ser Leu Thr Glu Lys Leu Gln Xaa Lys Glu Xaa Xaa Xaa
            195                 200                 205

Xaa Xaa Xaa Xaa Xaa Xaa Xaa Xaa Xaa Xaa Xaa Xaa Xaa Xaa Xaa
            210                 215                 220

Xaa Xaa Xaa Xaa Xaa Xaa Xaa Xaa Xaa Xaa Xaa Xaa Xaa Xaa Xaa
225                 230                 235                 240

Xaa Xaa Xaa Xaa Xaa Xaa Xaa Xaa Xaa Xaa Xaa Xaa Xaa Xaa Xaa
                245                 250                 255

Xaa Xaa Xaa Xaa Xaa Xaa Xaa Xaa Xaa Xaa Xaa Xaa Xaa Xaa Xaa
            260                 265                 270

Xaa Xaa Xaa Xaa Xaa Lys Xaa Glu Asp Xaa Xaa Ser Xaa Gly Xaa Xaa
            275                 280                 285

Xaa Ser Xaa Val Xaa Asp Xaa Asp Xaa Pro Xaa Xaa Xaa Xaa Xaa
            290                 295                 300

Xaa Xaa Xaa Xaa Xaa Xaa Xaa Xaa Xaa Xaa Xaa Asp Ser Xaa Xaa Xaa
305                 310                 315                 320

Xaa Xaa Xaa Xaa Xaa Xaa Xaa Xaa Xaa Xaa Xaa Xaa Xaa Xaa Xaa
                325                 330                 335

Xaa Xaa Xaa Xaa Xaa Xaa Xaa Xaa Gln Xaa Glu Glu Asp Xaa Xaa
            340                 345                 350

Xaa Xaa Xaa Xaa Xaa Xaa Xaa Xaa Xaa Xaa Xaa Xaa Xaa Xaa Xaa
            355                 360                 365

Xaa Xaa Asp Xaa Xaa Xaa Xaa Xaa Xaa Xaa Xaa Xaa Xaa Xaa Xaa
            370                 375                 380

Xaa Xaa Xaa Xaa Xaa Xaa Xaa Xaa Xaa Xaa Glu Xaa Xaa Xaa
385                 390                 395                 400

Xaa Xaa Xaa Trp

<210> SEQ ID NO 55
<211> LENGTH: 302
<212> TYPE: PRT
<213> ORGANISM: Medicago truncatula

<400> SEQUENCE: 55

Met Lys Arg Leu Asn Asn Thr Ser Asp Ser Phe Ser Thr Pro Leu Ile
1               5                   10                  15

Thr Ile Ser Pro Ser Thr Glu Glu His Ser Pro Arg Asn Lys His Val
                20                  25                  30

Tyr Gly Met Glu Phe Gln Ser Met Met Leu Asp Gly Phe Glu Glu Glu
            35                  40                  45

Gly Cys Val Glu Glu Thr Gly His His Ser Glu Lys Lys Arg Arg Leu
    50                  55                  60

Arg Val Asp Gln Val Lys Ala Leu Glu Lys Asn Phe Glu Val Glu Asn
65                  70                  75                  80

Lys Leu Glu Pro Glu Arg Lys Glu Lys Leu Ala Ile Glu Leu Gly Leu
                85                  90                  95

Gln Pro Arg Gln Val Ala Val Trp Phe Gln Asn Arg Arg Ala Arg Trp
            100                 105                 110
```

```
Lys Thr Lys Gln Leu Glu Arg Asp Tyr Gly Val Leu Lys Ala Asn Tyr
            115                 120                 125

Asp Ala Leu Lys Leu Lys Phe Asp Ala Ile Ala Gln Asp Asn Lys Ala
    130                 135                 140

Phe His Lys Glu Ile Lys Glu Leu Lys Ser Lys Leu Gly Glu Glu Glu
145                 150                 155                 160

Lys Ser Thr Ile Asn Val Leu Val Lys Glu Glu Leu Thr Met Leu Glu
                165                 170                 175

Ser Cys Asp Glu Asp Lys His Asn Pro Ser Ser Glu Thr Ser Asn Pro
            180                 185                 190

Ser Ser Glu Ser Lys Asp His Leu Asp Tyr Asp Cys Ile Ile Asn Asn
        195                 200                 205

Asn Asp Val Gly Ile Gly Glu Thr Ser Ser Leu Phe Pro Val Asp Leu
    210                 215                 220

Lys Asp Gly Ser Ser Asp Ser Asp Ser Ser Ala Ile Ser Ser Ser Gly
225                 230                 235                 240

Val Leu Gln Ser Gln Gln His Leu Leu Leu Ser Pro Glu Ser Ser Ser
                245                 250                 255

Met Asn Cys Phe Gln Tyr Gln Lys Ser Tyr His Val Lys Met Glu Glu
            260                 265                 270

His Asn Phe Leu Ser Ala Asp Glu Ala Cys Asn Phe Phe Ser Asp Glu
        275                 280                 285

Gln Ala Pro Thr Leu Gln Trp Tyr Cys Pro Asp Gln Trp Ser
    290                 295                 300

<210> SEQ ID NO 56
<211> LENGTH: 309
<212> TYPE: PRT
<213> ORGANISM: Picea glauca

<400> SEQUENCE: 56

Met Ala Cys Asp Arg Ser Ala Leu Tyr Thr Ser Ser Val Ile Met Asn
1               5                   10                  15

Thr Glu Asp Asn Ser Ser Ala His Ala Ile Ala Ala Met Ile Ala Ser
            20                  25                  30

Ser Cys Thr Pro Pro Ala Thr Phe Gln Gly Thr Arg Ser Ile Ser Val
        35                  40                  45

Phe Glu Thr Gly Asn Glu Arg Lys Arg Pro Ala Gly Asn Ser Tyr Ser
    50                  55                  60

Ala Leu Glu Leu Ser Asp Ile Gly Asp Glu Gly Ser Asp Asp
65                  70                  75                  80

Cys Ile His Leu Gly Glu Lys Arg Arg Leu Thr Leu Glu Gln Val
                85                  90                  95

Arg Ala Leu Glu Lys Asn Phe Glu Met Ala Asn Lys Leu Glu Pro Glu
            100                 105                 110

Lys Lys Met Gln Leu Ala Lys Ala Leu Gly Leu Gln Pro Arg Gln Ile
        115                 120                 125

Ala Val Trp Phe Gln Asn Arg Arg Ala Arg Trp Lys Thr Lys Gln Leu
    130                 135                 140

Glu Lys Asp Phe Asn Val Leu Lys Gln Asp Tyr Asp Ala Leu Lys Gln
145                 150                 155                 160

Asp Tyr Asp Asn Leu Met Glu Glu Asn Asn Leu Gln Ala Met Ile
                165                 170                 175

Glu Arg Met Ser Ser Lys Ser Gln Ser Cys Asn Asp Gln Lys Phe Gln
            180                 185                 190
```

Ala Asn Ser Ser Lys Leu Gln Lys Asp Asp Gln Asp Leu Gln Leu Leu
            195                 200                 205

Met Met Ser Ala Thr Lys Val Asp Cys Ala Asp Lys Glu Asn Asn Asn
            210                 215                 220

Glu Gly Pro Ser Ser Ile Gly Ser Glu Gly Ser Ser Val Leu Asp Met
225                 230                 235                 240

Asp Ser Pro Gly Thr Ile Asp Ser Gln Gln Asn Ile Asp Ser Ile Gly
            245                 250                 255

Phe Ser Asn Val Lys Ala Arg Asp Leu Arg Leu Glu Cys Asn Phe Arg
            260                 265                 270

Pro Lys Val Glu Glu Asn Val Ser Gln Ala Asp Glu Pro Cys Asn Tyr
            275                 280                 285

Leu Phe Tyr Asn Asn Leu Glu Thr Gly Pro Leu Leu Trp Asp Tyr Asn
            290                 295                 300

Trp Ser Ser Gly Leu
305

<210> SEQ ID NO 57
<211> LENGTH: 283
<212> TYPE: PRT
<213> ORGANISM: Medicago truncatula

<400> SEQUENCE: 57

Met His Glu Met Ala Phe Phe Gln Ala Asn Phe Met Leu Gln Thr Pro
1               5                   10                  15

His His His Asp Asp His His Gln Pro Ser Ser Leu Asn Ser Ile Leu
            20                  25                  30

Pro Gln Asp Tyr His Gly Gly Pro Ser Phe Leu Gly Lys Arg Cys Met
            35                  40                  45

Ser Phe Ser Ser Gly Ile Glu Leu Gly Glu Glu Ala Asn Ile Pro Glu
        50                  55                  60

Glu Asp Leu Ser Asp Asp Gly Ser Gln Ala Gly Glu Lys Lys Arg Arg
65                  70                  75                  80

Leu Asn Met Glu Gln Val Lys Thr Leu Glu Lys Ser Phe Glu Leu Gly
                85                  90                  95

Asn Lys Leu Glu Pro Glu Arg Lys Met Gln Leu Ala Arg Ala Leu Asn
            100                 105                 110

Leu Gln Pro Arg Gln Val Ala Ile Trp Phe Gln Asn Arg Arg Ala Arg
            115                 120                 125

Trp Lys Thr Lys Gln Leu Glu Lys Asp Tyr Asp Val Leu Lys Arg Gln
130                 135                 140

Tyr Asp Ala Ile Lys Leu Asp Asn Asp Ala Leu Gln Ala Gln Asn Gln
145                 150                 155                 160

Lys Leu Gln Ala Glu Ile Leu Ala Leu Lys Asn Arg Glu Pro Thr Glu
                165                 170                 175

Ser Ile Asn Leu Asn Lys Glu Thr Glu Gly Ser Ser Ser Asn Arg Ser
            180                 185                 190

Glu Asn Ser Ser Glu Ile Lys Leu Asp Met Ser Arg Thr Pro Ala Ser
            195                 200                 205

Asp Ser Pro Leu Ser Thr His Gln His Thr Thr Ser Arg Thr Phe Phe
            210                 215                 220

Pro Pro Ser Ala Arg Pro Ser Ser Gly Ile Ala Gln Leu Phe Gln Thr
225                 230                 235                 240

Ser Ser Arg Pro Glu Ile Gln Cys Gln Lys Ile Asp Gln Met Val Lys
                245                 250                 255

```
Glu Glu Ser Leu Ser Asn Met Phe Cys Gly Met Asp Asp Gln Ala Gly
            260                 265                 270

Phe Trp Pro Trp Leu Glu Gln Gln His Phe Asn
            275                 280
```

PLANTS HAVING IMPROVED GROWTH CHARACTERISTICS UNDER REDUCED NUTRIENT AVAILABILITY AND A METHOD FOR MAKING THE SAME

RELATED APPLICATIONS

This application is a national stage application (under 35 U.S.C. §371) of PCT/EP2008/055359, filed Apr. 30, 2008, which is a continuation-in-part of U.S. application Ser. No. 11/799,083, filed Apr. 30, 2007.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_Listing_17418_00104_US. The size of the text file is 117 KB, and the text file was created on Mar. 29, 2013.

The present invention relates generally to the field of molecular biology and concerns a method for improving plant growth characteristics relative to corresponding wild type plants. More specifically, the present invention concerns a method for increasing yield in plants grown under reduced nutrient availability, relative to corresponding wild type plants, comprising modulating expression in a plant of a nucleic acid sequence encoding class I homeodomain leucine zipper (HDZip) hox5 polypeptide or homologue thereof.

The ever-increasing world population and the dwindling supply of arable land available for agriculture fuels research towards increasing the efficiency of agriculture. Conventional means for crop and horticultural improvements utilise selective breeding techniques to identify plants having desirable characteristics. However, such selective breeding techniques have several drawbacks, namely that these techniques are typically labour intensive and result in plants that often contain heterogeneous genetic components that may not always result in the desirable trait being passed on from parent plants. Advances in molecular biology have allowed mankind to modify the germplasm of animals and plants. Genetic engineering of plants entails the isolation and manipulation of genetic material (typically in the form of DNA or RNA) and the subsequent introduction of that genetic material into a plant. Such technology has the capacity to deliver crops or plants having various improved economic, agronomic or horticultural traits.

A trait of particular economic interest is yield. Yield is normally defined as the measurable produce of economic value from a crop. This may be defined in terms of quantity and/or quality. Yield is directly dependent on several factors, for example, the number and size of the organs, plant architecture (for example, the number of branches), seed production and more. Root development, nutrient uptake and use efficiency, and stress tolerance may also be important factors in determining yield. Optimizing one of the abovementioned factors may therefore contribute to increasing crop yield.

Seed yield is a particularly important trait, since the seeds of many plants are important for human and animal nutrition. Crops such as, corn, rice, wheat, canola and soybean account for over half the total human caloric intake, whether through direct consumption of the seeds themselves or through consumption of meat products raised on processed seeds. They are also a source of sugars, oils and many kinds of metabolites used in industrial processes. Seeds contain an embryo (the source of new shoots and roots) and an endosperm (the source of nutrients for embryo growth during germination and during early growth of seedlings). The development of a seed involves many genes, and requires the transfer of metabolites from the roots, leaves and stems into the growing seed. The endosperm, in particular, assimilates the metabolic precursors of carbohydrates, oils and proteins and synthesizes them into storage macromolecules to fill out the grain.

Plant biomass is yield for forage crops like alfalfa, silage corn and hay. In particular root biomass is yield for crops such as potato, manioc or sugarbeet. Many proxies for yield have been used in grain crops. Chief amongst these are estimates of plant size. Plant size can be measured in many ways depending on species and developmental stage, but include total plant dry weight, above-ground dry weight, above-ground fresh weight, leaf area, stem volume, plant height, rosette diameter, leaf length, root length, root mass, tiller number and leaf number. Many species maintain a conservative ratio between the size of different parts of the plant at a given developmental stage. These allometric relationships are used to extrapolate from one of these measures of size to another (e.g. Tittonell et al. (2005) Agric Ecosys & Environ 105: 213). Plant size at an early developmental stage will typically correlate with plant size later in development. A larger plant with a greater leaf area can typically absorb more light and carbon dioxide than a smaller plant and therefore will likely gain a greater weight during the same period (Fasoula & Tollenaar (2005) Maydica 50: 39). This is in addition to the potential continuation of the micro-environmental or genetic advantage that the plant had to achieve the larger size initially. There is a strong genetic component to plant size and growth rate (e.g. ter Steege et al. (2005) Plant Physiology 139:1078), and so for a range of diverse genotypes plant size under one environmental condition is likely to correlate with size under another (Hittalmani et al. (2003) Theoretical Applied Genetics 107:679). In this way a standard environment is used as a proxy for the diverse and dynamic environments encountered at different locations and times by crops in the field.

Another important trait for many crops is early vigour. Improving early vigour is an important objective of modern rice breeding programs in both temperate and tropical rice cultivars. Long roots are important for proper soil anchorage in water-seeded rice. Where rice is sown directly into flooded fields, and where plants must emerge rapidly through water, longer shoots are associated with vigour. Where drill-seeding is practiced, longer mesocotyls and coleoptiles are important for good seedling emergence. The ability to engineer early vigour into plants would be of great importance in agriculture. For example, poor early vigour has been a limitation to the introduction of maize (*Zea mays* L.) hybrids based on Corn Belt germplasm in the European Atlantic.

Harvest index, the ratio of seed yield to aboveground dry weight, is relatively stable under many environmental conditions and so a robust correlation between plant size and grain yield can often be obtained (e.g. Rebetzke et al. (2002) Crop Science 42:739). These processes are intrinsically linked because the majority of grain biomass is dependent on current or stored photosynthetic productivity by the leaves and stem of the plant (Gardener et al. (1985) Physiology of Crop Plants. Iowa State University Press, pp 68-73). Therefore, selecting for plant size, even at early stages of development, has been used as an indicator for future potential yield (e.g. Tittonell et al. (2005) Agric Ecosys & Environ 105: 213). When testing for the impact of genetic differences on stress tolerance, the ability to standardize soil properties, temperature, water and nutrient availability and light intensity is an intrinsic advantage of greenhouse or plant growth chamber environments compared to the field. However, artificial limitations on yield due to poor pollination due to the absence of wind or insects, or insufficient space for mature root or canopy growth, can restrict the use of these controlled environments for testing yield differences. Therefore, measurements of plant size in early development, under standardized conditions in a growth chamber or greenhouse, are standard practices to provide indication of potential genetic yield advantages.

Another trait of importance is that of increased abiotic stress tolerance. Abiotic stress is a primary cause of crop loss worldwide, reducing average yields for most major crop plants by more than 50% (Wang et al. (2003) Planta 218: 1-14). Abiotic stresses may be caused by drought, salinity, extremes of temperature, chemical toxicity, excess or lack of nutrients (macroelements and/or microelements), radiation and oxidative stress. The ability to increase plant tolerance to abiotic stress would be of great economic advantage to farmers worldwide and would allow for the cultivation of crops during adverse conditions and in territories where cultivation of crops may not otherwise be possible.

The ability to increase plant yield would have many applications in areas such as agriculture, including in the production of ornamental plants, arboriculture, horticulture and forestry. Increasing yield may also find use in the production of algae for use in bioreactors (for the biotechnological production of substances such as pharmaceuticals, antibodies or vaccines, or for the bioconversion of organic waste) and other such areas.

BACKGROUND

Homeodomain leucine zipper (HDZip) proteins constitute a family of transcription factors characterized by the presence of a DNA-binding domain (HD) and an adjacent leucine zipper (Zip) motif. The homeodomain usually consists of 60 conserved amino acid residues that form a helix1-loop-helix2-turn-helix3 that binds DNA. This DNA binding site is usually pseudopalindromic. The leucine zipper, adjacent to the C-terminal end of the homeodomain, consists of several heptad repeats (at least four) in which usually a leucine (occasionally a valine or an isoleucine) appears every seventh amino acid. The leucine zipper is important for protein dimerisation. This dimerisation is a prerequisite for DNA binding (Sessa et al. (1993) EMBO J 12(9): 3507-3517), and may proceed between two identical HDZip proteins (homodimer) or between two different HDZip proteins (heterodimer).

Homeodomain genes are present in all eucaryotes, and constitute a gene family of at least 89 members in *Arabidopsis thaliana*. The leucine zipper is also found by itself in eucaryotes other than plants. However, the presence of both a homeodomain and a leucine zipper is plant-specific (found in at least 47 out of the 89 proteins in *Arabidopsis*), and has been encountered in moss in addition to vascular plants (Sakakibara et al. (2001) Mol Biol Evol 18(4): 491-502). The leucine zipper is then located at the C-terminal end of the homeodomain, these two features overlapping by three amino acids.

The *Arabidopsis* HDZip genes have been classified into four different classes, HDZip I to IV, based on sequence similarity criteria (Sessa et al. (1994) In Plant Molec Biol, pp 412-426). Like the HD-Zip proteins from the three other classes, class I HDZip proteins are quite divergent in their primary amino structure outside of the homeodomain and the leucine zipper. Within both the homeodomain and the leucine zipper, class I HDZip proteins are further characterized by two specific features:

1) in the homeodomain, in addition to the invariant amino acids $Leu_{16}Trp_{48}Phe_{49}Asn_{51}Arg_{53}$, position 46 is occupied by an Ala (A) and position 56 by a Try (W) (or occasionally by a Phe (F)) (Sessa et al. (1997) J Mol Biol 274(3):303-309; see FIG. 1), referred to as a class I homeodomain, and 2) the leucine zipper comprises six heptads, except for the fern *Ceratopteris richardii* which presents seven heptads (within each heptad, positions are named a, b, c, d, e, f and g, the conserved leucine being at position d; Sakakibara et al. (2001) Mol Biol Evol 18(4): 491-502; see FIG. 1). HDZip II, III and IV present a leucine zipper with five heptads only.

Concerning their DNA binding properties, class I HDZip proteins preferably bind to 5 bp half-sites that overlap at a central position, CAA(A/T)ATTG (Sessa et al. (1993) EMBO J 12(9): 3507-3517).

Different HDZip proteins have been shown to either activate or repress transcription. In *Arabidopsis*, the class I HDZip ATHB1, -5, -6, and -16 were shown to act as transcriptional activators in transient expression assays on *Arabidopsis* leaves using a reporter gene (luciferase; Henriksson et al. (2005) Plant Phys 139: 509-518). Two rice class I HDZip proteins, Oshox4 and Oshox5, acted as activators in transient expression assays on rice cell suspension cultures using another reporter gene (glucuronidase; Meijer et al. (2000) Mol Gen Genet 263:12-21). In contrast, two rice class II HDZip proteins, Oshox1 and Oshox3, acted as transcriptional repressors in the same experiments (Meijer et al. (1997) Plant J 11: 263-276; Meijer et al. (2000) supra).

Several class I HDZip proteins have been shown to be involved in light response and in abscisic acid (ABA)/water deficit related response (Hjellström et al. (2003) Plant Cell Environ 26: 1127-1136). Transgenic *Arabidopsis* overexpressing class I HDZip ATHB1, -3, -13, -20, and -23 suggest that these genes are involved in the regulation of cotyledon and leaf development (Aoyama et al. (1995) Plant Cell 7: 1773-1785; Hanson (2000) In Comprehensive summaries of Uppsala Dissertations from the Faculty of Science and Technology, Uppsala). The ATHB3, -13, -20, and -23 genes are similar and form a distinct subclass within the class I HDZip. Since these genes cause similar alterations in cotyledon shape when expressed constitutively, they are referred to as the pointed cotyledon (POC) HDZip genes. Hanson concludes that class I HDZip proteins that are closely related phylogenetically are also functionally related, in most cases.

Surprisingly, it has now been found that modulating expression in a plant a nucleic acid sequence encoding a class I HDZip hox5 polypeptide or a homologue thereof gives plants having increased yield under reduced nutrient availability, relative to corresponding wild type plants.

According to one embodiment of the present invention, there is provided a method for increasing yield in plants grown under reduced nutrient availability, relative to corresponding wild type plants, comprising modulating expression in a plant of a nucleic acid sequence encoding a class I HDZip hox5 polypeptide or a homologue thereof.

The choice of suitable control plants is a routine part of an experimental setup and may include corresponding wild type plants or corresponding plants without the gene of interest. The control plant is typically of the same plant species or even of the same variety as the plant to be assessed. The control plant may also be a nullizygote of the plant to be assessed. A "control plant" as used herein refers not only to whole plants, but also to plant parts, including seeds and seed parts.

Advantageously, performance of the methods according to the present invention results in plants having increased yield when grown under reduced nutrient availability, relative to corresponding wild type plants.

The term "increased yield" as defined herein is taken to mean an increase in any one or more of the following, each relative to corresponding wild type plants: (i) increased biomass (weight) of one or more parts of a plant, aboveground (harvestable) parts, or increased root biomass, increased root volume, increased root number, increased root diameter or increased root length (of thick or thin roots), or increased biomass of any other harvestable part; (ii) increased total seed yield, which includes an increase in seed biomass (seed weight) and which may be an increase in the seed weight per plant or on an individual seed basis; (iii) increased number of flowers (florets) per panicle, which is expressed as a ratio of number of filled seeds over number of primary panicles; (iv) increased seed fill rate; (v) number of (filled) seeds; (vi) increased seed size, which may also influence the composition of seeds; (vii) increased seed volume, which may also influence the composition of seeds (including oil, protein and carbohydrate total content and composition); (viii) increased (individual or average) seed area; (ix) increased (individual or average) seed length; (x) increased (individual or average) seed width; (xi) increased (individual or average) seed perimeter; (xii) increased harvest index (HI), which is expressed as a ratio of the yield of harvestable parts, such as seeds, over the total biomass; and (xiii) increased thousand kernel weight (TKW), which is extrapolated from the number of filled seeds counted and their total weight. An increased TKW may result from an increased seed size and/or seed weight. An increased TKW may result from an increase in embryo size and/or endosperm size.

Preferably, the increased yield is selected from one or more of the following: increased total number of seeds, increased number of filled seeds, increased total seed yield, increased number of flowers per panicle, increased seed fill rate, increased HI, increased TKW, increased root length or increased root diameter, each relative to corresponding wild type plants.

Therefore, according to the present invention, there is provided a method for increasing yield in plants grown under reduced nitrogen availability, relative to corresponding wild type plants, which method comprises modulating expression in a plant of a nucleic acid sequence encoding a class I HDZip hox5 polypeptide or a homologue thereof.

Taking corn as an example, an increased yield may be manifested as one or more of the following: increase in the number of plants per hectare or acre, an increase in the number of ears per plant, an increase in the number of rows, number of kernels per row, kernel weight, thousand kernel weight, ear length/diameter, among others. Taking rice as an example, a yield increase may be manifested by an increase in one or more of the following: number of plants per hectare or acre, number of panicles per plant, number of spikelets per panicle, number of flowers per panicle, increase in the seed filling rate, increase in thousand kernel weight, among others. An increased yield may also result in modified architecture, or may occur as a result of modified architecture.

Since the transgenic plants according to the present invention have increased yield under reduced nitrogen availability, it is likely that these plants exhibit an increased growth rate (during at least part of their life cycle), relative to the growth rate of corresponding wild type plants or control plants at a corresponding stage in their life cycle. The increased growth rate may be specific to one or more parts of a plant (including roots or seeds), or may be throughout substantially the whole plant. A plant having an increased growth rate may even exhibit early flowering. The increase in growth rate may take place at one or more stages in the life cycle of a plant or during substantially the whole plant life cycle. Increased growth rate during the early stages in the life cycle of a plant may reflect enhanced vigour. The increase in growth rate may alter the harvest cycle of a plant allowing plants to be sown later and/or harvested sooner than would otherwise be possible. If the growth rate is sufficiently increased, it may allow for the further sowing of seeds of the same plant species (for example sowing and harvesting of rice plants followed by sowing and harvesting of further rice plants all within one conventional growing period). Similarly, if the growth rate is sufficiently increased, it may allow for the further sowing of seeds of different plants species (for example the sowing and harvesting of rice plants followed by, for example, the sowing and optional harvesting of soy bean, potato or any other suitable plant). Harvesting additional times from the same rootstock in the case of some crop plants may also be possible. Altering the harvest cycle of a plant may lead to an increase in annual biomass production per acre (due to an increase in the number of times (say in a year) that any particular plant may be grown and harvested). An increase in growth rate may also allow for the cultivation of transgenic plants in a wider geographical area than their wild-type counterparts, since the territorial limitations for growing a crop are often determined by adverse environmental conditions either at the time of planting (early season) or at the time of harvesting (late season). Such adverse conditions may be avoided if the harvest cycle is shortened. The growth rate may be determined by deriving various parameters from growth curves, such parameters may be: T-Mid (the time taken for plants to reach 50% of their maximal size) and T-90 (time taken for plants to reach 90% of their maximal size), amongst others.

Performance of the methods of the invention gives plants having an increased growth rate. Therefore, according to the present invention, there is provided a method for increasing the growth rate of plants grown under reduced nitrogen availability, relative to corresponding wild type plants, which method comprises modulating expression in a plant of a nucleic acid sequence encoding a class I HDZip hox5 polypeptide or a homologue thereof.

Increased yield and/or growth rate occurs whether the plant is under non-stress conditions or whether the plant is exposed to various stresses compared to corresponding wild type plants grown under comparable conditions. Plant with optimal growth conditions (grown under non-stress conditions) typically yield in increasing order of preference at least 90%, 87%, 85%, 83%, 80%, 77% or 75% of the average production of such a plant in a given environment. Average production of such plant may be calculated on harvest and/or season and/or location basis. Persons skilled in the art are aware of average yield productions of a crop. Plants typically respond to exposure to stress by growing more slowly. In conditions of severe stress, the plant may even stop growing altogether. Mild stress on the other hand is defined herein as being any stress to which a plant is exposed which does not result in the plant ceasing to grow altogether without the capacity to resume growth. Mild stress in the sense of the invention leads to a reduction in the growth of the stressed plants of less than 40%, 35% or 30%, preferably less than 25%, 20% or 15%, more preferably less than 14%, 13%, 12%, 11% or 10% or less in comparison to the control plant under non-stress conditions. Due to advances in agricultural practices (irrigation, fertilization, pesticide treatments) severe stresses are not often encountered in cultivated crop plants. As a consequence, the compromised growth induced by mild stress is often an undesirable feature for agriculture. Mild stresses (as used herein) are the everyday abiotic (environmental) stresses to which a plant is exposed. Abiotic stresses may be due to drought or excess water, anaerobic stress, salt stress, chemical toxicity, oxidative stress and hot, cold or freezing temperatures, excess or reduced availability of nutrients (macroelements and/or microelements). The abiotic stress may be an osmotic stress caused by a water stress (particularly due to drought), salt stress, oxidative stress or an ionic stress. Biotic stresses are typically stresses caused by pathogens, such as bacteria, viruses, fungi, nematodes, and insects. The term "non-stress" conditions as used herein are those environmental conditions that allow optimal growth of plants.

Performance of the methods of the invention gives plants grown under non-stress conditions or under mild abiotic stress conditions having increased yield relative to corresponding wild type plants. Therefore, according to the present invention, there is provided a method for increasing yield of plants grown under non-stress conditions or under mild abiotic stress conditions, relative to corresponding wild type, which method comprises modulating expression in a plant of a nucleic acid sequence encoding a class I HDZip hox5 polypeptide or a homologue thereof. Preferably the mild abiotic stress conditions are reduced availability of nutrients.

Performance of the methods according to the present invention results in plants having increased tolerance to abiotic stress. As reported in Wang et al. (Planta (2003) 218: 1-14), abiotic stress leads to a series of morphological, physiological, biochemical and molecular changes that adversely affect plant growth and productivity. Drought, salinity, extreme temperatures and oxidative stress are known to be interconnected and may induce growth and cellular damage through similar mechanisms. For example, drought and/or salinisation are manifested primarily as osmotic stress, resulting in the disruption of homeostasis and ion distribution in the cell. Oxidative stress, which frequently accompanies high or low temperature, salinity or drought stress, may cause denaturation of functional and structural proteins. As a consequence, these diverse environmental stresses often activate similar cell signaling pathways and cellular responses, such as the production of stress proteins, up-regulation of antioxidants, accumulation of compatible solutes and growth arrest.

Diverse environmental stresses activate similar pathways, as exemplified in the present invention for plants grown in drought stress and salt stress conditions. These examples should be seen as a screen to indicate the involvement of class I HDZip hox5 polypeptides or homologues thereof in increasing tolerance to abiotic stresses in general. A particularly high degree of "cross talk" is reported between drought stress and high-salinity stress (Rabbani et al. (2003) Plant Physiol 133: 1755-1767). Therefore, it would be apparent that a class I HDZip hox5 polypeptide or a homologue thereof would, along with its usefulness in increasing drought-tolerance and salt-tolerance in plants, also find use in protecting the plant against various other abiotic stresses.

The term "abiotic stress" as defined herein is taken to mean any one or more of: water stress (due to drought or excess water), anaerobic stress, salt stress, temperature stress (due to hot, cold or freezing temperatures), chemical toxicity stress and oxidative stress. According to one aspect of the invention, the abiotic stress is an osmotic stress, selected from water stress, salt stress, oxidative stress and ionic stress. Preferably, the water stress is drought stress. The term salt stress is not restricted to stress resulting from excess common salt (NaCl), but may be from one or more of: NaCl, KCl, LiCl, $MgCl_2$, $CaCl_2$, amongst others.

Another example of abiotic environmental stress is the reduced availability of one or more nutrients that need to be assimilated by the plants for growth and development. Because of the strong influence of nutrition utilisation efficiency on plant yield and product quality, a huge amount of fertilizer is poured onto fields to optimize plant growth and quality. Productivity of plants ordinarily is limited by three primary nutrients, phosphorous, potassium and nitrogen, which is usually the rate-limiting element in plant growth of these three. Therefore the major nutritional element required for plant growth is nitrogen (N). It is a constituent of numerous important compounds found in living cells, including amino acids, proteins (enzymes), nucleic acids, and chlorophyll. 1.5% to 2% of plant dry matter is nitrogen and approximately 16% of total plant protein. Thus, nitrogen availability is a major limiting factor for crop plant growth and production (Frink et al. (1999) Proc Natl Acad Sci USA 96(4): 1175-1180), and has as well a major impact on protein accumulation and amino acid composition. Therefore, of great interest are crop plants with increased yield when grown under nutrient limiting conditions, preferably nitrogen-limiting conditions.

Performance of the methods of the invention gives plants having increased yield when grown under abiotic stress conditions, relative to corresponding wild type. Therefore, according to the present invention, there is provided a method for increasing yield in plants grown under abiotic stress conditions, relative to corresponding wild type plants, which method comprises modulating expression in a plant of a nucleic acid sequence encoding a class I HDZip hox5 polypeptide or a homologue thereof. According to one aspect of the invention, the abiotic stress is an osmotic stress, selected from one or more of the following: water stress, salt stress, oxidative stress and ionic stress. Preferably, the water stress is drought stress. Alternatively or additionally, the abiotic stress is reduced nutrient availability. Preferably, the abiotic stress is reduced nitrogen availability.

Increased tolerance to abiotic stress is manifested by plants with increased yield, relative to corresponding wild type plants. In particular, such increased yield may include one or more of the following: increased total number of seeds, increased number of filled seeds, increased total seed yield, increased number of flowers per panicle, increased seed fill rate, increased HI, increased TKW, increased root length or increased root diameter, each relative to corresponding wild type plants. Preferably the increased tolerance to abiotic stress is increased tolerance to reduced nutrient availability, more preferably increased tolerance to reduced nitrogen availability.

Advantageously, performance of the methods of the invention gives plants having an increased greenness index under reduced nutrient availability relative to corresponding wild type plants. The greenness index is calculated from the digital images of plants. For each pixel belonging to the plant object on the image, the ratio of the green value versus the red value (in the RGB model for encoding color) is calculated. The greenness index as defined herein is expressed as the percentage of pixels for which the green-to-red ratio exceeds a given threshold. An increased greenness index may indicate reduced or delayed senescence which in turn allows prolongation of the photosynthetic activity of a plant, which in turn leads to various beneficial effects well known in the art.

Performance of the methods of the invention gives plants having an increased greenness index under reduced nutrient availability, relative to corresponding wild type plants. Therefore, according to the present invention, there is provided a method for increasing greenness index in plants grown under reduced nutrient availability relative to corresponding wild type plants, which method comprises modulating expression in a plant of a nucleic acid sequence encoding a class I HDZip hox5 polypeptide or a homologue thereof. Preferably, the reduced nutrient availability conditions are reduced nitrogen availability conditions.

Rabbani et al. (2003, Plant Physiol 133: 1755-1767) report that similar molecular mechanisms of stress tolerance and responses exist between dicots and monocots. The methods of the invention are therefore advantageously applicable to any plant.

The term "plant" as used herein encompasses whole plants, ancestors and progeny of the plants and plant parts, including seeds, shoots, stems, leaves, roots (including tubers), flowers, and tissues and organs, wherein each of the aforementioned comprise the gene/nucleic acid sequence of interest. The term "plant" also encompasses plant cells, suspension cultures, callus tissue, embryos, meristematic regions, gametophytes, sporophytes, pollen and microspores, again wherein each of the aforementioned comprises the gene/nucleic acid sequence of interest. Therefore, the term "plant" as used herein encompasses a plant, plant part (including seeds), or plant cell obtainable by the methods of the invention, wherein each of the aforementioned comprises a recombinant nucleic acid sequence encoding a class I HDZip hox5 polypeptide or a homologue thereof.

Plants that are particularly useful in the methods of the invention include all plants which belong to the superfamily Viridiplantae, in particular monocotyledonous and dicotyledonous plants including fodder or forage legumes, ornamental plants, food crops, trees or shrubs selected from the list comprising *Acer* spp., *Actinidia* spp., *Abelmoschus* spp., *Agave sisalana, Agropyron* spp., *Agrostis stolonifera, Allium* spp., *Amaranthus* spp., *Ammophila arenaria, Ananas comosus, Annona* spp., *Apium graveolens, Arachis* spp, *Artocarpus* spp., *Asparagus officinalis, Avena* spp. (e.g. *Avena sativa, Avena fatua, Avena byzantina, Avena fatua* var. sativa, *Avena hybrida*), *Averrhoa carambola, Bambusa* sp., *Benincasa hispida, Bertholletia excelsea, Beta vulgaris, Brassica* spp. (e.g. *Brassica napus, Brassica rapa* ssp. [canola, oilseed rape, turnip rape]), *Cadaba farinosa, Camellia sinensis, Canna indica, Cannabis sativa, Capsicum* spp., *Carex elata, Carica papaya, Carissa macrocarpa, Carya* spp., *Carthamus tinctorius, Castanea* spp., *Ceiba pentandra, Cichorium endivia, Cinnamomum* spp., *Citrullus lanatus, Citrus* spp., *Cocos* spp., *Coffea* spp., *Colocasia esculenta, Cola* spp., *Corchorus* sp., *Coriandrum sativum, Corylus* spp., *Crataegus* spp., *Crocus sativus, Cucurbita* spp., *Cucumis* spp., *Cynara* spp., *Daucus carota, Desmodium* spp., *Dimocarpus longan, Dioscorea* spp., *Diospyros* spp., *Echinochloa* spp., *Elaeis* (e.g. *Elaeis guineensis, Elaeis oleifera*), *Eleusine coracana, Erianthus* sp., *Eriobotrya japonica, Eucalyptus* sp., *Eugenia uniflora, Fagopyrum* spp., *Fagus* spp., *Festuca arundinacea, Ficus carica, Fortunella* spp., *Fragaria* spp., *Ginkgo biloba, Glycine* spp. (e.g. *Glycine max, Soja hispida* or *Soja max*), *Gossypium hirsutum, Helianthus* spp. (e.g. *Helianthus annuus*), *Hemerocallis fulva, Hibiscus* spp., *Hordeum* spp. (e.g. *Hordeum vulgare*), *Ipomoea batatas, Juglans* spp., *Lactuca sativa, Lathyrus* spp., *Lens culinaris, Linum usitatissimum, Litchi chinensis, Lotus* spp., *Luffa acutangula, Lupinus* spp., *Luzula sylvatica, Lycopersicon* spp. (e.g. *Lycopersicon esculentum, Lycopersicon lycopersicum, Lycopersicon pyriforme*), *Macrotyloma* spp., *Malus* spp., *Malpighia emarginata, Mammea americana, Mangifera indica, Manihot* spp., *Manilkara zapota, Medicago sativa, Melilotus* spp., *Mentha* spp., *Miscanthus sinensis, Momordica* spp., *Morus nigra, Musa* spp., *Nicotiana* spp., *Olea* spp., *Opuntia* spp., *Ornithopus* spp., *Oryza* spp. (e.g. *Oryza sativa, Oryza latifolia*), *Panicum miliaceum, Panicum virgatum, Passiflora edulis, Pastinaca sativa, Pennisetum* sp., *Persea* spp., *Petroselinum crispum, Phalaris arundinacea, Phaseolus* spp., *Phleum pratense, Phoenix* spp., *Phragmites australis, Physalis* spp., *Pinus* spp., *Pistacia vera, Pisum* spp., *Poa* spp., *Populus* spp., *Prosopis* spp., *Prunus* spp., *Psidium* spp., *Punica granatum, Pyrus communis, Quercus* spp., *Raphanus sativus, Rheum rhabarbarum, Ribes* spp., *Ricinus communis, Rubus* spp., *Saccharum* spp., *Salix* sp., *Sambucus* spp., *Secale cereale, Sesamum* spp., *Sinapis* sp., *Solanum* spp. (e.g. *Solanum tuberosum, Solanum integrifolium* or *Solanum lycopersicum*), *Sorghum bicolor, Spinacia* spp., *Syzygium* spp., *Tagetes* spp., *Tamarindus indica, Theobroma cacao, Trifolium* spp., *Triticosecale rimpaui, Triticum* spp. (e.g. *Triticum aestivum, Triticum durum, Triticum turgidum, Triticum hybernum, Triticum macha, Triticum sativum* or *Triticum vulgare*), *Tropaeolum minus, Tropaeolum majus, Vaccinium* spp., *Vicia* spp., *Vigna* spp., *Viola odorata, Vitis* spp., *Zea mays, Zizania palustris, Ziziphus* spp., amaranth, artichoke, asparagus, broccoli, Brussels sprouts, cabbage, canola, carrot, cauliflower, celery, collard greens, flax, kale, lentil, oilseed rape, okra, onion, potato, rice, soybean, strawberry, sugar beet, sugar cane, sunflower, tomato, squash, tea and algae, amongst others. According to a preferred embodiment of the present invention, the plant is a crop plant such as soybean, sunflower, canola, alfalfa, rapeseed, cotton, tomato, potato or tobacco. Further preferably, the plant is a monocotyledonous plant, such as sugar cane. More preferably the plant is a cereal, such as rice, maize, wheat, barley, triticale, millet, rye, sorghum or oats.

The term "class I HDZip hox5 polypeptide or homologue thereof" as defined herein refers to a polypeptide comprising from N-terminal to C-terminal: (i) an acidic box; and (ii) a class I homeodomain; and (iii) a leucine zipper with more than 5 heptads.

Additionally, the class I HDZip hox5 polypeptide or a homologue thereof may comprise any one or both of the following: (a) a Trp tail; and (b) the RPFF amino acid motif, where R is Arg, P Pro and F Phe. The motif of (b) precedes the acidic box, when examining the protein from N-terminal to C-terminal.

An example of a class I HDZip hox5 polypeptide as defined hereinabove comprising from N-terminal to C-terminal: (i) an acidic box; and (ii) a class I homeodomain; and (iii) a leucine zipper with more than 5 heptads; and additionally comprising: (a) a Trp tail; and (b) the RPFF amino acid motif, where R is Arg, P Pro and F Phe, is represented as in SEQ ID NO: 2. Further such examples are given in Table A of Example 1 herein.

A class I HDZip hox5 polypeptide or homologue thereof is encoded by a class I HDZip hox5 gene/nucleic acid sequence. Therefore the term "class I HDZip hox5 gene/nucleic acid sequence" as defined herein is any gene/nucleic acid sequence encoding a class I HDZip hox5 polypeptide or a homologue thereof as defined hereinabove.

Class I HDZip hox5 polypeptides or homologues thereof may readily be identified using routine techniques well known in the art, such as by sequence alignment. Methods for the alignment of sequences for comparison are well known in the art, such methods include GAP, BESTFIT, BLAST, FASTA and TFASTA. GAP uses the algorithm of Needleman and Wunsch ((1970) J Mol Biol 48: 443-453) to find the alignment of two complete sequences that maximizes the number of matches and minimizes the number of gaps. The BLAST algorithm (Altschul et al. (1990) J Mol Biol 215: 403-10) calculates percent sequence identity and performs a statistical analysis of the similarity between the two sequences. The software for performing BLAST analysis is publicly available through the National Centre for Biotechnology Information. Homologues of class I HDZip hox5 polypeptides comprising a class I homeodomain and a leucine zipper with more than 5 heptads may readily be identified using, for example, the ClustalW multiple sequence alignment algorithm (version 1.83), with the default pairwise alignment parameters, and a scoring method in percentage. Minor manual editing may be performed to optimise alignment between conserved motifs, as would be apparent to a person skilled in the art (see Example 2 and FIG. 2 herein).

The various structural domains in a class I HDZip hox5 polypeptide, such as the homeodomain and the leucine zipper, may be identified using specialised databases e.g. SMART (Schultz et al. (1998) Proc. Natl. Acad. Sci. USA 95, 5857-5864; Letunic et al. (2002) Nucl Acids Res 30, 242-244; hosted by EMBL at Heidleberg), InterPro (Mulder et al., (2003) Nucl Acids Res. 31, 315-318), Prosite (Bucher and Bairoch (1994), A generalized profile syntax for biomolecular sequences motifs and its function in automatic sequence interpretation. (In) ISMB-94; Proceedings 2nd International Conference on Intelligent Systems for Molecular Biology. Altman R., Brutlag D., Karp P., Lathrop R., Searls D., Eds., pp 53-61, AAAIPress, Menlo Park; Hulo et al., Nucl. Acids. Res. 32:D134-D137, (2004)) or Pfam (Bateman et al., Nucl Acids Res 30(1):276-280 (2002)). Leucine zipper prediction and heptad identification may be done using specialised software such as 2ZIP, which combines a standard coiled coil prediction algorithm with an approximate search for the characteristic leucine repeat (Bornberg-Bauer et al. (1998) Computational Approaches to Identify Leucine Zippers, Nucl Acids Res, 26(11): 2740-2746). Results of domain identification in class I HDZip hox5 polypeptide sequences are presented in Example 4 of this application.

Furthermore, the presence of an acidic box may also readily be identified. Primary amino acid composition (in %) to determine if a polypeptide domain is rich in specific amino acids may be calculated using software programs from the ExPASy server, in particular the ProtParam tool (Gasteiger E et al. (2003) ExPASy: the proteomics server for in-depth protein knowledge and analysis. Nucleic Acids Res 31:3784-3788). The composition of the protein of interest may then be compared to the average amino acid composition (in %) in the Swiss-Prot Protein Sequence data bank. Within this databank, the average Asp (D) and Glu (E) content are of 5.3% and of 6.6% respectively, the combined average being of 11.9%. As an example, the acidic box of SEQ ID NO: 2 comprises 9.1% of D and 54.5% of E, the combined average being of 63.6% (see Example 4 herein). As defined herein, an acidic rich box has a combined Asp (D) and Glu (E) content (in % terms) above that found in the average amino acid composition (in % terms) of the proteins in the Swiss-Prot Protein Sequence database. An acidic box may be part of a transcription activation domain. Eukaryotic transcription activation domains have been classified according to their amino acid content, and major categories include acidic, glutamine-rich and proline-rich activation domains (Rutherford et al. (2005) Plant J. 43(5): 769-88, and references therein).

A selected number of polypeptides amongst the class I HDZip hox5 polypeptides or homologues thereof further comprise the RPFF amino acid motif, where R is Arg, P Pro and F Phe, This motif precedes the acidic box, when examining the protein from N-terminal to C-terminal (see FIG. 2). The presence of the RPFF may be identified using methods for the alignment of sequences for comparison as described hereinabove. In some instances, the default parameters may be adjusted to modify the stringency of the search. For example using BLAST, the statistical significance threshold (called "expect" value) for reporting matches against database sequences may be increased to show less stringent matches. This way, short nearly exact matches may be identified.

A selected number of polypeptides amongst the class I HDZip hox5 polypeptides or homologues thereof may further comprise a Trp tail. A Trp tail as defined herein is the last 10 amino acids of the C-terminal of the polypeptide comprising at least one Trp residue (see FIG. 2).

Examples of class I HDZip hox5 polypeptides or homologues thereof (encoded by polynucleotide sequence accession number in parenthesis) are given in Table A of the Examples.

It is to be understood that sequences falling under the definition of "class I HDZip hox5 polypeptide or homologue thereof" are not to be limited to the sequences given in Table A, but that any polypeptide comprising from N-terminal to C-terminal: (i) an acidic box; and (ii) a class I homeodomain; and (iii) a leucine zipper with more than 5 heptads, may be suitable for use in performance of the methods of the invention.

Class I HDZip hox5 polypeptides or homologues thereof have DNA binding activity, preferably to 5 bp half-sites that overlap at a central position, CAA(A/T)ATTG, as detected in yeast one-hybrid assays (Meijer et al. (2000) Mol Gen Genet 263:12-21). In transient assays on rice cell suspensions, co-bombardement of a class I HDZip hox5 polypeptide with the GUS reporter gene resulted in an increase number of stained spots, which were also more intense in color (Meijer et al, supra). This assay is useful to demonstrate the activator function of class I HDZip hox5 polypeptides or homologues.

Examples of class I HDZip hox5 nucleic acid sequences include but are not limited to those listed in Table A of the Examples. Class I HDZip hox5 genes/nucleic acid sequences and variants thereof may be suitable in practising the methods of the invention. Variants of class I HDZip hox5 genes/nucleic acid sequences include portions of a class I HDZip hox5 gene/nucleic acid sequence and/or nucleic acid sequences capable of hybridising with a class I HDZip hox5 gene/nucleic acid sequence.

The term portion as defined herein refers to a piece of DNA encoding a polypeptide comprising from N-terminal to C-terminal: (i) an acidic box; and (ii) a class I homeodomain; and (iii) a leucine zipper with more than 5 heptads. A portion may be prepared, for example, by making one or more deletions to a class I HDZip hox5 nucleic acid sequence. The portions may be used in isolated form or they may be fused to other coding (or non coding) sequences in order to, for example, produce a protein that combines several activities. When fused to other coding sequences, the resulting polypeptide produced upon translation may be bigger than that predicted for the class I HDZip hox5 portion. Preferably, the portion is a portion of a nucleic acid sequence as represented by any one of the nucleic acid sequences listed in Table A of Example 1 herein. Most preferably the portion is a portion of a nucleic acid sequence as represented by SEQ ID NO: 1.

Another variant of a class I HDZip hox5 gene/nucleic acid sequence is a nucleic acid sequence capable of hybridising under reduced stringency conditions, preferably under stringent conditions, with a class I HDZip hox5 gene/nucleic acid sequence as hereinbefore defined, which hybridising sequence encodes a polypeptide comprising from N-terminal to C-terminal: (i) an acidic box; and (ii) a class I homeodomain; and (iii) a leucine zipper with more than 5 heptads. Preferably, the hybridising sequence is one that is capable of hybridising to a nucleic acid sequence as represented by any one of the nucleic acid sequences listed in Table A of Example 1 herein, or to a portion of any of the aforementioned sequences as defined hereinabove. Most preferably the hybridising sequence is one that is capable of hybridising to a nucleic acid sequence as represented by SEQ ID NO: 1.

The term "hybridisation" as defined herein is a process wherein substantially homologous complementary nucleotide sequences anneal to each other. The hybridisation process can occur entirely in solution, i.e. both complementary nucleic acid molecules are in solution. The hybridisation process can also occur with one of the complementary nucleic acid molecules immobilised to a matrix such as magnetic beads, Sepharose beads or any other resin. The hybridisation process can furthermore occur with one of the complementary nucleic acid molecules immobilised to a solid support such as a nitro-cellulose or nylon membrane or immobilised by e.g. photolithography to, for example, a siliceous glass support (the latter known as nucleic acid sequence arrays or microarrays or as nucleic acid sequence chips). In order to allow hybridisation to occur, the nucleic acid molecules are generally thermally or chemically denatured to melt a double strand into two single strands and/or to remove hairpins or other secondary structures from single stranded nucleic acid molecules. The stringency of hybridisation is influenced by conditions such as temperature, salt concentration, ionic strength and hybridisation buffer composition.

"Stringent hybridisation conditions" and "stringent hybridisation wash conditions" in the context of nucleic acid hybridisation experiments such as Southern and Northern hybridisations are sequence dependent and are different under different environmental parameters. The skilled artisan is aware of various parameters which may be altered during hybridisation and washing and which will either maintain or change the stringency conditions.

The $T_m$, is the temperature under defined ionic strength and pH, at which 50% of the target sequence hybridises to a perfectly matched probe. The $T_m$ is dependent upon the solution conditions and the base composition and length of the probe. For example, longer sequences hybridise specifically at higher temperatures. The maximum rate of hybridisation is obtained from about 16° C. up to 32° C. below $T_m$. The presence of monovalent cations in the hybridisation solution reduce the electrostatic repulsion between the two nucleic acid strands thereby promoting hybrid formation; this effect is visible for sodium concentrations of up to 0.4M. Formamide reduces the melting temperature of DNA-DNA and DNA-RNA duplexes with 0.6 to 0.7° C. for each percent formamide, and addition of 50% formamide allows hybridisation to be performed at 30 to 45° C., though the rate of hybridisation will be lowered. Base pair mismatches reduce the hybridisation rate and the thermal stability of the duplexes. On average and for large probes, the $T_m$ decreases about 1° C. per % base mismatch. The $T_m$, may be calculated using the following equations, depending on the types of hybrids:

1. DNA-DNA hybrids (Meinkoth and Wahl, Anal. Biochem., 138: 267-284, 1984):
   $T_m = 81.5°$ C. $+16.6 \times \log[Na^+]^a + 0.41 \times$ %[G/C$^b$] $-500 \times [L^c]^{-1} - 0.61 \times$ % formamide
2. DNA-RNA or RNA-RNA hybrids:
   $T_m = 79.8 + 18.5$ $(\log_{10}[Na^+]^a) + 0.58$ (% G/C$^b$) $+ 11.8$ (% G/C$^b$)$^2 - 820/L^c$
3. oligo-DNA or oligo-RNA$^d$ hybrids:
   For <20 nucleotides: $T_m = 2 (l_n)$
   For 20-35 nucleotides: $T_m = 22 + 1.46 (l_n)$ $^a$ or for other monovalent cation, but only accurate in the 0.01-0.4 M range.
$^b$ only accurate for % GC in the 30% to 75% range.
$^c$ L=length of duplex in base pairs.
$^d$ Oligo, oligonucleotide; $l_n$, effective length of primer=2×(no. of G/C)+(no. of A/T).

Note: for each 1% formamide, the $T_m$, is reduced by about 0.6 to 0.7° C., while the presence of 6 M urea reduces the $T_m$, by about 30° C.

Specificity of hybridisation is typically the function of post-hybridisation washes. To remove background resulting from non-specific hybridisation, samples are washed with dilute salt solutions. Critical factors of such washes include the ionic strength and temperature of the final wash solution: the lower the salt concentration and the higher the wash temperature, the higher the stringency of the wash. Wash conditions are typically performed at or below hybridisation stringency. Generally, suitable stringent conditions for nucleic acid sequence hybridisation assays or gene amplification detection procedures are as set forth above. Conditions of greater or less stringency may also be selected. Generally, low stringency conditions are selected to be about 50° C. lower than the thermal melting point ($T_m$) for the specific sequence at a defined ionic strength and pH. Medium stringency conditions are when the temperature is 20° C. below $T_m$, and high stringency conditions are when the temperature is 10° C. below $T_m$. For example, stringent conditions are those that are at least as stringent as, for example, conditions A-L; and reduced stringency conditions are at least as stringent as, for example, conditions M-R. Non-specific binding may be controlled using any one of a number of known techniques such as, for example, blocking the membrane with protein containing solutions, additions of heterologous RNA, DNA, and SDS to the hybridisation buffer, and treatment with RNase. Examples of hybridisation and wash conditions are listed in Table 1 below.

TABLE 1

Examples of hybridisation and wash conditions

| Stringency Condition | Polynucleotide Hybrid$^\pm$ | Hybrid Length (bp)$^\ddagger$ | Hybridisation Temperature and Buffer$^\dagger$ | Wash Temperature and Buffer$^\dagger$ |
|---|---|---|---|---|
| A | DNA:DNA | > or equal to 50 | 65° C. 1 × SSC; or 42° C., 1 × SSC and 50% formamide | 65° C.; 0.3 × SSC |
| B | DNA:DNA | <50 | Tb*; 1 × SSC | Tb*; 1 × SSC |
| C | DNA:RNA | > or equal to 50 | 67° C. 1 × SSC; or 45° C., 1 × SSC and 50% formamide | 67° C.; 0.3 × SSC |
| D | DNA:RNA | <50 | Td*; 1 × SSC | Td*; 1 × SSC |
| E | RNA:RNA | > or equal to 50 | 70° C. 1 × SSC; or 50° C., 1 × SSC and 50% formamide | 70° C.; 0.3 × SSC |
| F | RNA:RNA | <50 | Tf*; 1 × SSC | Tf*; 1 × SSC |
| G | DNA:DNA | > or equal to 50 | 65° C. 4 × SSC; or 45° C., 4 × SSC and 50% formamide | 65° C.; 1 × SSC |

TABLE 1-continued

Examples of hybridisation and wash conditions

| Stringency Condition | Polynucleotide Hybrid± | Hybrid Length (bp)‡ | Hybridisation Temperature and Buffer† | Wash Temperature and Buffer† |
|---|---|---|---|---|
| H | DNA:DNA | <50 | Th*; 4 × SSC | Th*; 4 × SSC |
| I | DNA:RNA | > or equal to 50 | 67° C. 4 × SSC; or 45° C., 4 × SSC and 50% formamide | 67° C.; 1 × SSC |
| J | DNA:RNA | <50 | Tj*; 4 × SSC | Tj*; 4 × SSC |
| K | RNA:RNA | > or equal to 50 | 70° C. 4 × SSC; or 40° C., 6 × SSC and 50% formamide | 67° C.; 1 × SSC |
| L | RNA:RNA | <50 | Tl*; 2 × SSC | Tl*; 2 × SSC |
| M | DNA:DNA | > or equal to 50 | 50° C. 4 × SSC; or 40° C., 6 × SSC and 50% formamide | 50° C.; 2 × SSC |
| N | DNA:DNA | <50 | Tn*; 6 × SSC | Tn*; 6 × SSC |
| O | DNA:RNA | > or equal to 50 | 55° C. 4 × SSC; or 42° C., 6 × SSC and 50% formamide | 55° C.; 2 × SSC |
| P | DNA:RNA | <50 | Tp*; 6 × SSC | Tp*; 6 × SSC |
| Q | RNA:RNA | > or equal to 50 | 60° C. 4 × SSC; or 45° C., 6 × SSC and 50% formamide | 60° C.; 2 × SSC |
| R | RNA:RNA | <50 | Tr*; 4 × SSC | Tr*; 4 × SSC |

‡The "hybrid length" is the anticipated length for the hybridising nucleic acid sequence. When nucleic acid sequences of known sequence are hybridised, the hybrid length may be determined by aligning the sequences and identifying the conserved regions described herein.
†SSPE (1 × SSPE is 0.15M NaCl, 10 mM $NaH_2PO_4$, and 1.25 mM EDTA, pH7.4) may be substituted for SSC (1 × SSC is 0.15M NaCl and 15 mM sodium citrate) in the hybridisation and wash buffers; washes are performed for 15 minutes after hybridisation is complete. The hybridisations and washes may additionally include 5 × Denhardt's reagent, 0.5-1.0% SDS, 100 µg/ml denatured, fragmented salmon sperm DNA, 0.5% sodium pyrophosphate, and up to 50% formamide.
*Tb-Tr: The hybridisation temperature for hybrids anticipated to be less than 50 base pairs in length should be 5-10° C. less than the melting temperature $T_m$ of the hybrids; the $T_m$ is determined according to the above-mentioned equations.
±The present invention also encompasses the substitution of any one, or more DNA or RNA hybrid partners with either a PNA, or a modified nucleic acid.

For the purposes of defining the level of stringency, reference can be made to Sambrook et al. (2001) Molecular Cloning: a laboratory manual, 3$^{rd}$ Edition Cold Spring Harbor Laboratory Press, CSH, New York or to Current Protocols in Molecular Biology, John Wiley & Sons, N.Y. (1989).

The class I HDZip hox5 nucleic acid sequence may be derived from any natural or artificial source. The gene/nucleic acid sequence may be isolated from a microbial source, such as yeast or fungi, or from a plant, algae or animal (including human) source. This nucleic acid sequence may be modified from its native form in composition and/or genomic environment through deliberate human manipulation. The nucleic acid sequence is of plant origin, whether from the same plant species (for example to the one in which it is to be introduced) or whether from a different plant species. Preferably, the nucleic acid sequence may be isolated from a monocotyledonous species, further preferably from the family Poaceae, more preferably from *Oryza* genus, most preferably from *Oryza sativa*. More preferably, the class I HDZip hox5 nucleic acid sequence isolated from *Oryza sativa* is represented by SEQ ID NO: 1 and the class I HDZip hox5 polypeptide sequence is as represented by SEQ ID NO: 2.

The expression of a nucleic acid sequence encoding a class I HDZip hox5 polypeptide or a homologue thereof may be modulated by introducing a genetic modification, by any one (or more) of the following methods: T-DNA activation, TILLING, site-directed mutagenesis, directed evolution and homologous recombination or by introducing and expressing in a plant a nucleic acid sequence encoding a class I HDZip hox5 polypeptide or a homologue thereof. Following introduction of the genetic modification, there follows a step of selecting for modulated expression of a nucleic acid sequence encoding a class I HDZip hox5 polypeptide or a homologue thereof, which modulation in expression gives plants having increased yield under reduced nutrient availability, relative to corresponding wild type plants.

T-DNA activation tagging (Hayashi et al. Science (1992) 1350-1353) involves insertion of T-DNA, usually containing a promoter (may also be a translation enhancer or an intron), in the genomic region of the gene of interest or 10 kb up- or down stream of the coding region of a gene in a configuration such that the promoter directs expression of the targeted gene. Typically, regulation of expression of the targeted gene by its natural promoter is disrupted and the gene falls under the control of the newly introduced promoter. The promoter is typically embedded in a T-DNA. This T-DNA is randomly inserted into the plant genome, for example, through *Agrobacterium* infection and leads to overexpression of genes near the inserted T-DNA. The resulting transgenic plants show dominant phenotypes due to overexpression of genes close to the introduced promoter. The promoter to be introduced may be any promoter capable of directing expression of a gene in the desired organism, in this case a plant. For example, constitutive, tissue-preferred, cell type-preferred and inducible promoters are all suitable for use in T-DNA activation.

A genetic modification may also be introduced in the locus of a class I HDZip hox5 gene using the technique of TILLING (Targeted Induced Local Lesions In Genomes). This is a mutagenesis technology useful to generate and/or identify, and to eventually isolate mutagenised variants of a class I HDZip hox5 nucleic acid sequence capable of exhibiting class I HDZip hox5 activity. TILLING also allows selection of plants carrying such mutant variants. These mutant variants may even exhibit higher class I HDZip hox5 activity than that exhibited by the gene in its natural form. TILLNG combines high-density mutagenesis with high-throughput screening methods. The steps typically followed in TILLING are: (a) EMS mutagenesis (Redei GP and Koncz C (1992) In Methods in *Arabidopsis* Research, Koncz C, Chua N H, Schell J, eds. Singapore, World Scientific Publishing Co, pp. 16-82; Feldmann et al., (1994) In Meyerowitz E M, Somerville C R, eds, *Arabidopsis*. Cold Spring Harbor Laboratory Press, Cold Spring Harbor, N.Y., pp 137-172; Lightner J and Caspar T (1998) In J Martinez-Zapater, J Salinas, eds, Methods on Molecular Biology, Vol. 82. Humana Press, Totowa, N.J., pp 91-104); (b) DNA preparation and pooling of individuals; (c) PCR amplification of a region of interest; (d) denaturation and annealing to allow formation of heteroduplexes; (e) DHPLC, where the presence of a heteroduplex in a pool is detected as an extra peak in the chromatogram; (f) identification of the mutant individual; and (g) sequencing of the mutant PCR product. Methods for TILLING are well known in the art (McCallum et al., (2000) Nat Biotechnol 18: 455-457; reviewed by Stemple (2004) Nat Rev Genet 5(2): 145-50).

Homologous recombination allows introduction in a genome of a selected nucleic acid sequence at a defined selected position. Homologous recombination is a standard technology used routinely in biological sciences for lower organisms such as yeast or the moss *Physcomitrella*. Methods for performing homologous recombination in plants have been described not only for model plants (Offring a et al. (1990) EMBO J 9(10): 3077-84) but also for crop plants, for example rice (Terada et al. (2002) Nat Biotech 20(10): 1030-4; Iida and Terada (2004) Curr Opin Biotech 15(2): 132-8). The nucleic acid sequence to be targeted (which may be a class I HDZip hox5 nucleic acid sequence or variant thereof as hereinbefore defined) need not be targeted to the locus of a class I HDZip hox5 gene, but may be introduced in, for example, regions of high expression. The nucleic acid sequence to be targeted may be an improved allele used to replace the endogenous gene or may be introduced in addition to the endogenous gene.

Site-directed mutagenesis may be used to generate variants of class I HDZip hox5 nucleic acid sequences. Several methods are available to achieve site-directed mutagenesis, the most common being PCR based methods (Current Protocols in Molecular Biology, Wiley Eds).

Directed evolution may also be used to generate variants of class I HDZip hox5 nucleic acid sequences. This consists of iterations of DNA shuffling followed by appropriate screening and/or selection to generate variants of class I HDZip hox5 nucleic acid sequences or portions thereof encoding class I HDZip hox5 polypeptides or homologues or portions thereof having an modified biological activity (Castle et al., (2004) Science 304(5674): 1151-4; U.S. Pat. Nos. 5,811,238 and 6,395,547).

T-DNA activation, TILLING, homologous recombination, site-directed mutagenesis, and directed evolution are methods to introduce a genetic modification to modulate expression of a nucleic acid sequence encoding a class I HDZip hox5 polypeptide or a homologue thereof. Therefore, according to the present invention, there is provided a method for modulating expression of a nucleic acid sequence encoding a class I HDZip hox5 polypeptide or a homologue thereof, comprising introducing a genetic modification by one or more of: T-DNA activation, TILLING, homologous recombination, site-directed mutagenesis, and directed evolution.

A preferred method for introducing a genetic modification (which in this case need not be in the locus of a class I HDZip hox5 gene) is to introduce and express in a plant a nucleic acid sequence encoding a class I HDZip hox5 polypeptide or a homologue thereof. A class I HDZip hox5 polypeptide or a homologue thereof is defined as polypeptide comprising from N-terminal to C-terminal: (i) an acidic box; and (ii) a class I homeodomain; and (iii) a leucine zipper with more than 5 heptads. The nucleic acid sequence to be introduced into a plant may be a full-length nucleic acid sequence or may be a portion or a hybridising sequence as hereinbefore defined.

"Homologues" of a protein encompass peptides, oligopeptides, polypeptides, proteins and enzymes having amino acid substitutions, deletions and/or insertions relative to the unmodified protein in question and having similar biological and functional activity as the unmodified protein from which they are derived. To produce such homologues, amino acids of the protein may be replaced by other amino acids having similar properties (such as similar hydrophobicity, hydrophilicity, antigenicity, propensity to form or break α-helical structures or β-sheetstructures). Conservative substitution tables are well known in the art (see for example Creighton (1984) Proteins. W.H. Freeman and Company and Table 2 below). The homologues useful in the methods according to the invention are preferably class I HDZip hox5 polypeptides as defined herein above.

Also encompassed by the term "homologues" are two special forms of homology, which include orthologous sequences and paralogous sequences, which encompass evolutionary concepts used to describe ancestral relationships of genes. The term "paralogous" relates to gene-duplications within the genome of a species leading to paralogous genes. The term "orthologous" relates to homologous genes in different organisms due to speciation.

Orthologues in, for example, monocot plant species may easily be found by performing a so-called reciprocal blast search. This may be done by a first blast involving blasting the sequence in question (for example, SEQ ID NO: 1 or SEQ ID NO: 2) against any sequence database, such as the publicly available NCBI database. BLASTN or TBLASTX may be used when starting from nucleotide sequence, or BLASTP or TBLASTN when starting from the polypeptide, with standard default values. The BLAST results may be filtered. The full-length sequences of either the filtered results or the non-filtered results are then BLASTed back (second BLAST) against the sequences of the organism from which the sequence in question is derived. The results of the first and second BLASTs are then compared. When the results of the second BLAST give as hits with the highest similarity a class I HDZip hox5 nucleic acid sequence or class I HDZip hox5 polypeptide, then a paralogue has been found, if it originates from the same organism as for the sequence used in the first BLAST. In case it originates from an organism other than that of the sequence used in the first BLAST, then an orthologue has been found. In the case of large families, ClustalW may be used, followed by a neighbour joining tree, to help visualize the clustering. Preferably, such class I HDZip hox5 polypeptides have in increasing order of preference at least 30%, 40%, 50%, 60%, 70%, 80%, 85%, 90%, 95%, 96%, 97%, 98% or 99% or more sequence identity or similarity (functional identity) to an unmodified class I HDZip hox5 polypeptide (preferably SEQ ID NO: 2; see Example 3 herein). Percentage identity between class I HDZip hox5 homologues outside of the homeodomain and the leucine zipper is reputedly low (see Example 3 herein). Examples of orthologs and paralogs of a class I HDZip hox5 polypeptide as represented by SEQ ID NO: 2 may be found in Table of Example 1 herein.

A homologue may be in the form of a "substitutional variant" of a protein, i.e. where at least one residue in an amino acid sequence has been removed and a different residue inserted in its place. Amino acid substitutions are typically of single residues, but may be clustered depending upon functional constraints placed upon the polypeptide; insertions will usually be of the order of about 1 to 10 amino acid residues. Preferably, amino acid substitutions comprise conservative amino acid substitutions. Conservative substitution tables are readily available in the art. The table below gives examples of conserved amino acid substitutions.

TABLE 2

Examples of conserved amino acid substitutions

| Residue | Conservative Substitutions |
|---|---|
| Ala | Ser |
| Arg | Lys |
| Asn | Gln; His |
| Asp | Glu |
| Gln | Asn |
| Cys | Ser |
| Glu | Asp |
| Gly | Pro |
| His | Asn; Gln |
| Ile | Leu, Val |
| Leu | Ile; Val |
| Lys | Arg; Gln |
| Met | Leu; Ile |
| Phe | Met; Leu; Tyr |
| Ser | Thr; Gly |
| Thr | Ser; Val |
| Trp | Tyr |
| Tyr | Trp; Phe |
| Val | Ile; Leu |

A homologue may also be in the form of an "insertional variant" of a protein, i.e. where one or more amino acid residues are introduced into a predetermined site in a protein. Insertions may comprise N-terminal and/or C-terminal fusions as well as intra-sequence insertions of single or multiple amino acids. Generally, insertions within the amino acid sequence will be smaller than N- or C-terminal fusions, of the order of about 1 to 10 residues. Examples of N- or C-terminal fusion proteins or peptides include the binding domain or activation domain of a transcriptional activator as used in the yeast two-hybrid system, phage coat proteins, (histidine)-6-tag, glutathione S-transferase-tag, protein A, maltose-binding protein, dihydrofolate reductase, Tag•100 epitope, c-myc epitope, FLAG®-epitope, lacZ, CMP (calmodulin-binding peptide), HA epitope, protein C epitope and VSV epitope.

Homologues in the form of "deletion variants" of a protein are characterised by the removal of one or more amino acids from a protein.

Amino acid variants of a protein may readily be made using peptide synthetic techniques well known in the art, such as solid phase peptide synthesis and the like, or by recombinant DNA manipulations. Methods for the manipulation of DNA sequences to produce substitution, insertion or deletion variants of a protein are well known in the art. For example, techniques for making substitution mutations at predetermined sites in DNA are well known to those skilled in the art and include M13 mutagenesis, T7-Gen in vitro mutagenesis (USB, Cleveland, Ohio), QuickChange Site Directed mutagenesis (Stratagene, San Diego, Calif.), PCR-mediated site-directed mutagenesis or other site-directed mutagenesis protocols.

The class I HDZip hox5 polypeptide or homologue thereof may be a derivative. "Derivatives" include peptides, oligopeptides, polypeptides which may, compared to the amino acid sequence of the naturally-occurring form of the protein, such as the protein of interest, comprise substitutions of amino acids with non-naturally occurring amino acid residues, or additions of non-naturally occurring amino acid residues. "Derivatives" of a protein also encompass peptides, oligopeptides, polypeptides which comprise naturally occurring altered (glycosylated, acylated, prenylated, phosphorylated, myristoylated, sulphated etc.) or non-naturally altered amino acid residues compared to the amino acid sequence of a naturally-occurring form of the polypeptide. A derivative may also comprise one or more non-amino acid substituents or additions compared to the amino acid sequence from which it is derived, for example a reporter molecule or other ligand, covalently or non-covalently bound to the amino acid sequence, such as a reporter molecule which is bound to facilitate its detection, and non-naturally occurring amino acid residues relative to the amino acid sequence of a naturally-occurring protein.

The class I HDZip hox5 polypeptide or homologue thereof may be encoded by an alternative splice variant of a class I HDZip hox5 gene/nucleic acid sequence. The term "alternative splice variant" as used herein encompasses variants of a nucleic acid sequence in which selected introns and/or exons have been excised, replaced or added, or in which introns have been shortened or lengthened. Such variants will be ones in which the biological activity of the protein is retained, which may be achieved by selectively retaining functional segments of the protein. Such splice variants may be found in nature or may be manmade. Methods for making such splice variants are well known in the art. Preferred splice variants are splice variants of a nucleic acid sequence encoding a polypeptide comprising from N-terminal to C-terminal: (i) an acidic box; and (ii) a class I homeodomain; and (iii) a leucine zipper with more than 5 heptads. Additionally, a class I HDZip hox5 polypeptide or a homologue thereof may comprise one or both of the following: (a) a Trp tail; and (b) the RPFF amino acid motif, where R is Arg, P Pro and F Phe. The motif of (b) precedes the acidic box, when examining the protein from N-terminal to C-terminal. Further preferred are splice variants of nucleic acid sequences as listed in Table A of Example 1 herein. Most preferred is a splice variant of a nucleic acid sequence as represented by SEQ ID NO: 1.

The homologue may also be encoded by an allelic variant of a nucleic acid sequence encoding a class I HDZip hox5 polypeptide or a homologue thereof, preferably an allelic variant of a nucleic acid sequence encoding a polypeptide comprising from N-terminal to C-terminal: (i) an acidic box; and (ii) a class I homeodomain; and (iii) a leucine zipper with more than 5 heptads. Additionally, a class I HDZip hox5 polypeptide or a homologue thereof may comprise one or both of the following: (a) a Trp tail; and (b) the RPFF amino acid motif, where R is Arg, P Pro and F Phe. The motif of (b) precedes the acidic box, when examining the protein from N-terminal to C-terminal. Further preferred are allelic variants of nucleic acid sequences listed in Table A of Example 1 herein. Most preferred is an allelic variant of a nucleic acid sequence as represented by SEQ ID NO: 1. Allelic variants exist in nature, and encompassed within the methods of the present invention is the use of these natural alleles. Allelic variants encompass Single Nucleotide Polymorphisms (SNPs), as well as Small Insertion/Deletion Polymorphisms (INDELs). The size of INDELs is usually less than 100 bp. SNPs and INDELs form the largest set of sequence variants in naturally occurring polymorphic strains of most organisms.

According to a preferred aspect of the present invention, modulated expression of the class I HDZip hox5 nucleic acid sequence is envisaged. Methods for modulating expression of genes or gene products are well documented in the art and include, for example, overexpression driven by appropriate promoters, the use of transcription enhancers or translation enhancers. Isolated nucleic acid sequences which serve as promoter or enhancer elements may be introduced in an appropriate position (typically upstream) of a non-heterologous form of a polynucleotide so as to upregulate expression of a class I HDZip hox5 nucleic acid sequence. For example, endogenous promoters may be altered in vivo by mutation, deletion, and/or substitution (see, Kmiec, U.S. Pat. No. 5,565, 350; Zarling et al., PCT/US93/03868), or isolated promoters may be introduced into a plant cell in the proper orientation and distance from a gene of the present invention so as to control the expression of the gene. Methods for reducing the expression of genes or gene products are well documented in the art.

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added may be derived from, for example, the nopaline synthase or octopine synthase genes, or alternatively from another plant gene, or less preferably from any other eukaryotic gene.

An intron sequence may also be added to the 5' untranslated region or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg (1988) Mol. Cell biol. 8: 4395-4405; Callis et al. (1987) Genes Dev 1:1183-1200). Such intron enhancement of gene expression is typically greatest when placed near the 5' end of the transcription unit. Use of the maize introns Adh1-S intron 1, 2, and 6, the Bronze-1 intron are known in the art. See generally, The Maize Handbook, Chapter 116, Freeling and Walbot, Eds., Springer, N.Y. (1994).

The invention also provides genetic constructs and vectors to facilitate introduction and/or expression of the nucleotide sequences useful in the methods according to the invention.

Therefore, there is provided a gene construct comprising:
(i) A class I HDZip hox5 nucleic acid sequence, as defined hereinabove;
(ii) One or more control sequences capable of driving expression of the nucleic acid sequence of (i); and optionally
(iii) A transcription termination sequence.

Constructs useful in the methods according to the present invention may be constructed using recombinant DNA technology well known to persons skilled in the art. The gene constructs may be inserted into vectors, which may be commercially available, suitable for transforming into plants and suitable for expression of the gene of interest in the transformed cells. The invention therefore provides use of a gene construct as defined hereinabove in the methods of the invention.

Plants are transformed with a vector comprising the sequence of interest (i.e., a nucleic acid sequence encoding a class I HDZip hox5 polypeptide or homologue thereof). The sequence of interest is operably linked to one or more control sequences (at least to a promoter). The terms "regulatory element", "control sequence" and "promoter" are all used interchangeably herein and are to be taken in a broad context to refer to regulatory nucleic acid sequences capable of effecting expression of the sequences to which they are ligated. Encompassed by the aforementioned terms are transcriptional regulatory sequences derived from a classical eukaryotic genomic gene (including the TATA box which is required for accurate transcription initiation, with or without a CCAAT box sequence) and additional regulatory elements (i.e. upstream activating sequences, enhancers and silencers) which alter gene expression in response to developmental and/or external stimuli, or in a tissue-specific manner. Also included within the term is a transcriptional regulatory sequence of a classical prokaryotic gene, in which case it may include a −35 box sequence and/or −10 box transcriptional regulatory sequences. The term "regulatory element" also encompasses a synthetic fusion molecule or derivative that confers, activates or enhances expression of a nucleic acid sequence molecule in a cell, tissue or organ. The term "operably linked" as used herein refers to a functional linkage between the promoter sequence and the gene of interest, such that the promoter sequence is able to initiate transcription of the gene of interest.

Advantageously, any type of promoter may be used to drive expression of the nucleic acid sequence. The promoter may be an inducible promoter, i.e. having induced or increased transcription initiation in response to a developmental, chemical, environmental or physical stimulus. An example of an inducible promoter being a stress-inducible promoter, i.e. a promoter activated when a plant is exposed to various stress conditions. Additionally or alternatively, the promoter may be a tissue-preferred promoter, i.e. one that is capable of preferentially initiating transcription in certain tissues, such as the leaves, roots, seed tissue etc. Promoters able to initiate transcription in certain tissues only are referred to herein as "tissue-specific".

In one embodiment, a class I HDZip hox5 nucleic acid sequence is operably linked to a constitutive promoter. A constitutive promoter is transcriptionally active during most but not necessarily all phases of its growth and development and is substantially ubiquitously expressed. The constitutive promoter is preferably a GOS2 promoter, more preferably the constitutive promoter is a rice GOS2 promoter, further preferably the constitutive promoter is represented by a nucleic acid sequence substantially similar to SEQ ID NO: 33 or SEQ ID NO: 52, most preferably the constitutive promoter is as represented by SEQ ID NO: 33 or SEQ ID NO: 52. It should be clear that the applicability of the present invention is not restricted to the class I HDZip hox5 nucleic acid sequence represented by SEQ ID NO: 1, nor is the applicability of the invention restricted to expression of a class I HDZip hox5 nucleic acid sequence when driven by a GOS2 promoter. Examples of other constitutive promoters which may also be used perform the methods of the invention are shown in Table 3 below.

TABLE 3

Examples of constitutive promoters

| Gene Source | Expression Pattern | Reference |
|---|---|---|
| Actin | Constitutive | McElroy et al., Plant Cell, 2: 163-171, 1990 |
| CAMV 35S | Constitutive | Odell et al., Nature, 313: 810-812, 1985 |
| CaMV 19S | Constitutive | Nilsson et al., *Physiol. Plant*. 100: 456-462, 1997 |
| GOS2 | Constitutive | de Pater et al., Plant J Nov; 2(6): 837-44, 1992 |
| Ubiquitin | Constitutive | Christensen et al., Plant Mol. Biol. 18: 675-689, 1992 |
| Rice cyclophilin | Constitutive | Buchholz et al., Plant Mol Biol. 25(5): 837-43, 1994 |
| Maize H3 histone | Constitutive | Lepetit et al., Mol. Gen. Genet. 231: 276-285, 1992 |
| Actin 2 | Constitutive | An et al., Plant J. 10(1); 107-121, 1996 |
| HMGB | Constitutive | WO 2004/070039 |

Optionally, one or more terminator sequences may also be used in the construct introduced into a plant. The term "terminator" encompasses a control sequence which is a DNA sequence at the end of a transcriptional unit which signals 3' processing and polyadenylation of a primary transcript and termination of transcription. Additional regulatory elements may include transcriptional as well as translational enhancers. Those skilled in the art will be aware of terminator and enhancer sequences that may be suitable for use in performing the invention. Such sequences would be known or may readily be obtained by a person skilled in the art.

The genetic constructs of the invention may further include an origin of replication sequence that is required for maintenance and/or replication in a specific cell type. One example is when a genetic construct is required to be maintained in a bacterial cell as an episomal genetic element (e.g. plasmid or cosmid molecule). Preferred origins of replication include, but are not limited to, the f1-ori and colE1.

The genetic construct may optionally comprise a selectable marker gene. As used herein, the term "selectable marker gene" includes any gene that confers a phenotype on a cell in which it is expressed to facilitate the identification and/or selection of cells that are transfected or transformed with a nucleic acid sequence construct of the invention. Suitable markers may be selected from markers that confer antibiotic or herbicide resistance, that introduce a new metabolic trait or that allow visual selection. Examples of selectable marker genes include genes conferring resistance to antibiotics (such as nptII that phosphorylates neomycin and kanamycin, or hpt, phosphorylating hygromycin), to herbicides (for example bar which provides resistance to Basta; aroA or gox providing resistance against glyphosate, or the genes conferring resistance to, for example, imidazolinone, phosphinothricin or sulfonylurea), or genes that provide a metabolic trait (such as manA that allows plants to use mannose as sole carbon source). Expression of visual marker genes results in the formation of colour (for example β-glucuronidase, GUS), luminescence (such as luciferase) or fluorescence (Green Fluorescent Protein, GFP, and derivatives thereof).

In a preferred embodiment, there is provided a gene construct comprising:
  (i) A class I HDZip hox5 nucleic acid sequence, as defined hereinabove;
  (ii) A constitutive promoter capable of driving expression of the nucleic acid sequence of (i); and optionally
  (iii) A transcription termination sequence.

The constitutive promoter is preferably a GOS2 promoter, more preferably the constitutive promoter is the rice GOS2 promoter, further preferably the constitutive promoter is represented by a nucleic acid sequence substantially similar to SEQ ID NO: 33 or to SEQ ID NO: 52, most preferably the constitutive promoter is as represented by SEQ ID NO: 33 or to SEQ ID NO: 52. The invention further provides use of a construct as defined hereinabove in the methods of the invention.

The present invention also encompasses plants obtainable by the methods according to the present invention. The present invention therefore provides plants, plant parts or plant cells thereof obtainable by the method according to the present invention, which plants or parts or cells thereof comprise a transgene class I HDZip hox5 nucleic acid sequence.

The invention also provides a method for the production of transgenic plants having increased yield under reduced variant nutrient availability, relative to corresponding wild type plants, comprising introduction and expression in a plant of a nucleic acid sequence encoding class I HDZip hox5 polypeptide or a homologue thereof.

More specifically, the present invention provides a method for the production of transgenic plants having increased yield under reduced nutrient availability, relative to corresponding wild type plants, which method comprises:
  (i) introducing and expressing in a plant, plant part or plant cell a class I HDZip hox5 nucleic acid sequence; and
  (ii) cultivating the plant cell under conditions promoting plant growth and development.

The nucleic acid sequence may be introduced directly into a plant cell or into the plant itself (including introduction into a tissue, organ or any other part of a plant). According to a preferred feature of the present invention, the nucleic acid sequence is preferably introduced into a plant by transformation.

The term "transformation" as referred to herein encompasses the transfer of an exogenous polynucleotide into a host cell, irrespective of the method used for transfer. Plant tissue capable of subsequent clonal propagation, whether by organogenesis or embryogenesis, may be transformed with a genetic construct of the present invention and a whole plant regenerated therefrom. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. The resulting transformed plant cell may then be used to regenerate a transformed plant in a manner known to persons skilled in the art.

Transformation of plant species is now a fairly routine technique. Advantageously, any of several transformation methods may be used to introduce the gene of interest into a suitable ancestor cell. Transformation methods include the use of liposomes, electroporation, chemicals that increase free DNA uptake, injection of the DNA directly into the plant, particle gun bombardment, transformation using viruses or pollen and microprojection. Methods may be selected from the calcium/polyethylene glycol method for protoplasts (Krens, F. A. et al. (1982) Nature 296, 72-74; Negrutiu I et al. (1987) Plant Mol Biol 8: 363-373); electroporation of protoplasts (Shillito R. D. et al. (1985) Bio/Technol 3, 1099-1102); microinjection into plant material (Crossway A et al. (1986) Mol. Gen Genet 202: 179-185); DNA or RNA-coated particle bombardment (Klein T M et al. (1987) Nature 327: 70) infection with (non-integrative) viruses and the like. Transgenic rice plants expressing a class I HDZip hox5 gene/nucleic acid sequence are preferably produced via *Agrobacterium*-mediated transformation using any of the well known methods for rice transformation, such as described in any of the following: published European patent application EP 1198985 A1, Aldemita and Hodges (Planta 199: 612-617, 1996); Chan et al. (Plant Mol Biol 22 (3): 491-506, 1993), Hiei et al. (Plant J 6 (2): 271-282, 1994), which disclosures are incorporated by reference herein as if fully set forth. In the case of corn transformation, the preferred method is as described in either Ishida et al. (Nat. Biotechnol 14(6): 745-50, 1996) or Frame et al. (Plant Physiol 129(1): 13-22, 2002), which disclosures are incorporated by reference herein as if fully set forth.

Generally after transformation, plant cells or cell groupings are selected for the presence of one or more markers which are encoded by plant-expressible genes co-transferred with the gene of interest, following which the transformed material is regenerated into a whole plant. Following DNA transfer and regeneration, putatively transformed plants may be evaluated, for instance using Southern analysis, for the presence of the gene of interest, copy number and/or genomic organisation. Alternatively or additionally, expression levels of the newly introduced DNA may be monitored using Northern and/or Western analysis, or quantitative PCR, all techniques being well known to persons having ordinary skill in the art.

The generated transformed plants may be propagated by a variety of means, such as by clonal propagation or classical breeding techniques. For example, a first generation (or T1) transformed plant may be selfed to give homozygous second generation (or T2) transformants, and the T2 plants further propagated through classical breeding techniques.

The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

The present invention clearly extends to any plant cell or plant produced by any of the methods described herein, and to all plant parts and propagules thereof. The present invention extends further to encompass the progeny of a primary transformed or transfected cell, tissue, organ or whole plant that has been produced by any of the aforementioned methods, the only requirement being that progeny exhibit the same genotypic and/or phenotypic characteristic(s) as those produced by the parent in the methods according to the invention.

The invention also includes host cells containing an isolated class I HDZip hox5 nucleic acid sequence. Preferred host cells according to the invention are plant cells.

The invention also extends to harvestable parts of a plant such as, but not limited to seeds, leaves, fruits, flowers, stems, rhizomes, tubers and bulbs. The invention furthermore relates to products derived from a harvestable part of such a plant, such as dry pellets or powders, oil, fat and fatty acids, starch or proteins.

The present invention also encompasses use of class I HDZip hox5 nucleic acid and use of class I HDZip hox5 polypeptides or homologues thereof. Such uses relate to increasing yield in plants grown under reduced nutrient availability, relative to wild type plants, as defined hereinabove in the methods of the invention. Preferably, the increased yield is one or more of: increased total seed yield per plant, increased number of filled seeds, increased seed fill rate, increased number of flowers per panicle, or increased harvest index.

Class I HDZip hox5 nucleic acid sequences or variants thereof, or class I HDZip hox5 polypeptides or homologues thereof may find use in breeding programmes in which a DNA marker is identified which may be genetically linked to a class I HDZip hox5 gene or variant thereof. The class I HDZip hox5 genes/nucleic acid sequences or variants thereof, or class I HDZip hox5 polypeptides or homologues thereof may be used to define a molecular marker. This DNA or protein marker may then be used in breeding programmes to select plants having increased yield when grown under reduced nutrient availability, as defined hereinabove in the methods of the invention. The class I HDZip hox5 gene may, for example, be a nucleic acid sequence as listed in Table A of Example 1 herein.

Allelic variants of a class I HDZip hox5 gene/nucleic acid sequence may also find use in marker-assisted breeding programmes. Such breeding programmes sometimes require introduction of allelic variation by mutagenic treatment of the plants, using for example EMS mutagenesis; alternatively, the programme may start with a collection of allelic variants of so called "natural" origin caused unintentionally. Identification of allelic variants then takes place, for example, by PCR. This is followed by a step for selection of superior allelic variants of the sequence in question and which give plants with increased yield under reduced nutrient availability, relative to corresponding wild type plants. Selection is typically carried out by monitoring growth performance of plants containing different allelic variants of the sequence in question, for example, different allelic variants of any one of the nucleic acid sequences listed in Table A of Example 1 herein. Growth performance may be monitored in a greenhouse or in the field. Further optional steps include crossing plants in which the superior allelic variant was identified with another plant. This could be used, for example, to make a combination of interesting phenotypic features.

A class I HDZip hox5 nucleic acid sequence or variant thereof may also be used as probes for genetically and physically mapping the genes that they are a part of, and as markers for traits linked to those genes. Such information may be useful in plant breeding in order to develop lines with desired phenotypes. Such use of class I HDZip hox5 nucleic acid sequences or variants thereof requires only a nucleic acid sequence of at least 15 nucleotides in length. The class I HDZip hox5 nucleic acid sequences or variants thereof may be used as restriction fragment length polymorphism (RFLP) markers. Southern blots (Sambrook J, Fritsch E F and Maniatis T (1989) Molecular Cloning, A Laboratory Manual) of restriction-digested plant genomic DNA may be probed with the class I HDZip hox5 nucleic acid sequences or variants thereof. The resulting banding patterns may then be subjected to genetic analyses using computer programs such as MapMaker (Lander et al. (1987) Genomics 1: 174-181) in order to construct a genetic map. In addition, the nucleic acid sequences may be used to probe Southern blots containing restriction endonuclease-treated genomic DNAs of a set of individuals representing parent and progeny of a defined genetic cross. Segregation of the DNA polymorphisms is noted and used to calculate the position of the class I HDZip hox5 nucleic acid sequence or variant thereof in the genetic map previously obtained using this population (Botstein et al. (1980) Am. J. Hum. Genet. 32:314-331).

The production and use of plant gene-derived probes for use in genetic mapping is described in Bernatzky and Tanksley (1986) Plant Mol. Biol. Reporter 4: 37-41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

The nucleic acid sequence probes may also be used for physical mapping (i.e., placement of sequences on physical maps; see Hoheisel et al. In: Non-mammalian Genomic Analysis: A Practical Guide, Academic press 1996, pp. 319-346, and references cited therein).

In another embodiment, the nucleic acid sequence probes may be used in direct fluorescence in situ hybridisation (FISH) mapping (Trask (1991) Trends Genet. 7:149-154). Although current methods of FISH mapping favor use of large clones (several kb to several hundred kb; see Laan et al. (1995) Genome Res. 5:13-20), improvements in sensitivity may allow performance of FISH mapping using shorter probes.

A variety of nucleic acid sequence amplification-based methods for genetic and physical mapping may be carried out using the nucleic acid sequences. Examples include allele-specific amplification (Kazazian (1989) J. Lab. Clin. Med 11:95-96), polymorphism of PCR-amplified fragments (CAPS; Sheffield et al. (1993) Genomics 16:325-332), allele-specific ligation (Landegren et al. (1988) Science 241:1077-1080), nucleotide extension reactions (Sokolov (1990)

Nucleic acid sequence Res. 18:3671), Radiation Hybrid Mapping (Walter et al. (1997) Nat. Genet. 7:22-28) and Happy Mapping (Dear and Cook (1989) Nucleic acid sequence Res. 17:6795-6807). For these methods, the sequence of a nucleic acid sequence is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

The methods according to the present invention result in plants having increased yield under reduced nutrient availability, as described hereinbefore. This increased yield may also be combined with other economically advantageous traits, such as further yield-enhancing traits, tolerance to other abiotic and biotic stresses, traits modifying various architectural features and/or biochemical and/or physiological features.

DESCRIPTION OF FIGURES

The present invention will now be described with reference to the following figures in which:

FIG. 1 shows a multiple alignment of class I HDZip homeodomains from different plant sources, using VNTI AlignX multiple alignment program, based on a modified ClustalW algorithm (InforMax, Bethesda, Md.), with default settings for gap opening penalty of 10 and a gap extension of 0.05). The homeodomain invariant amino acids $L_{16}$, $W_{43}$, $F_{49}$, $N_{51}$ and $R_{53}$ are boxed vertically. HDZip Class I preferred amino acids $A_{46}$ and $W_{56}$ are equally boxed vertically. The three helixes necessary for DNA binding are marked as black boxes above the alignment. The six heptads are separated by a vertical line. The seven positions within each heptad are named a, b, c, d, e, f and g. The Leu occupies the d position within each heptad, and is boxed vertically. Consensus (SEQ ID NO: 53).

FIG. 2 shows a multiple alignment of several plant class I HDZip hox5 polypeptides, using VNTI AlignX multiple alignment program, based on a modified ClustalW algorithm (InforMax, Bethesda, Md.), with default settings for gap opening penalty of 10 and a gap extension of 0.05). The three main characterized domains, from N-terminal to C-terminal, are heavily boxed and identified as the acidic box, the class I homeodomain and the six heptad-leucine zipper. Additionally, the Trp tail and the RPFF amino acid motif are lightly boxed. Sequences shown are: Zeama_hox5 (SEQ ID NO: 6); Aqufo_hox5 (SEQ ID NO: 32); Arath_ATHB1 (SEQ ID NO: 16); Orysa_hox5 (SEQ ID NO: 2); Crapl_CPHB-5 (SEQ ID NO: 22); Dauca_CHB3 (SEQ ID NO: 18); Glyma_HD157 (SEQ ID NO: 20); Goshi_Hox5 (SEQ ID NO: 24); Lyces_hox5 (SEQ ID NO: 26); Lyces_VaHOX1 (SEQ ID NO: 28); Medtr_HOX16_1 (SEQ ID NO: 47); Orysa_hox16 (SEQ ID NO: 4); Sacof_hox5 (SEQ ID NO: 10); Sorbi_hox5 (SEQ ID NO: 12); Triae_hox16 (SEQ ID NO: 14); Zeama_hox16 (SEQ ID NO: 8); Poptr_HOX16_1 (SEQ ID NO: 41); Poptr_HOX16_2 (SEQ ID NO: 43); Poptr_HOX16_3 (SEQ ID NO: 45); Phavu_hox16 (SEQ ID NO: 49); Lotco_HOX16 (SEQ ID NO: 51); Medtr_HOX unknown (SEQ ID NO: 55); Piclg_hox unknown (SEQ ID NO: 56); Orysa_hox4 (SEQ ID NO: 37); Medtr_HOX unknown2 (SEQ ID NO: 57); Orysa_hox6 (SEQ ID NO: 39); and Consensus (SEQ ID NO: 54).

FIG. 4 details examples of class I homeodomain leucine zipper (HDZip) hox5 sequences useful in performing the methods according to the present invention. Several sequences result from public EST assemblies (see Table A of Example 1 herein), with lesser quality sequencing. As a consequence, a few nucleic acid substitutions may be expected. The start (ATG) and stop codons delimit the nucleic acid sequences encoding full length I HDZip hox5 polypeptides.

EXAMPLES

Figure 3:
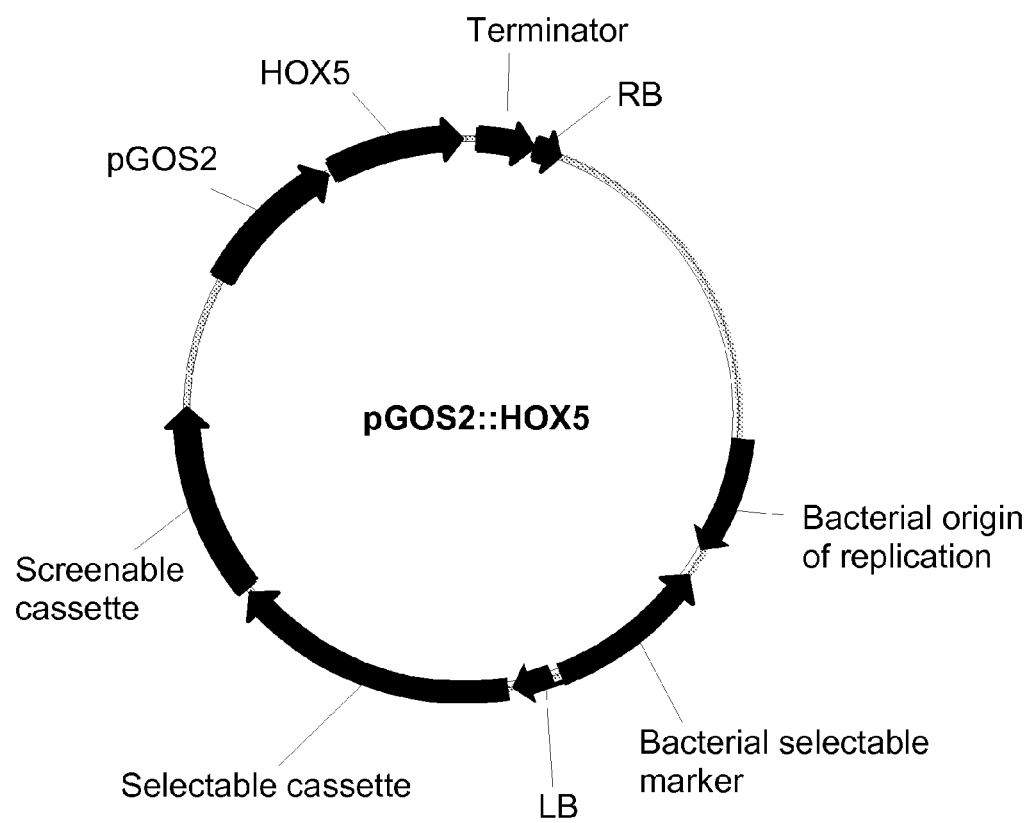
FIG. 3 shows a binary vector for expression in *Oryza sativa* of an *Oryza sativa* class I HDZip hox5 under the control of a GOS2 promoter.

The present invention will now be described with reference to the following examples, which are by way of illustration alone and are not intended to completely define or to otherwise limit the scope of the invention.

Unless otherwise stated, recombinant DNA techniques were performed according to standard protocols described in (Sambrook (2001) Molecular Cloning: a laboratory manual, 3rd Edition Cold Spring Harbor Laboratory Press, CSH, New York) or in Volumes 1 and 2 of Ausubel et al. (1994), Current Protocols in Molecular Biology, Current Protocols. Standard materials and methods for plant molecular work are described in Plant Molecular Biology Labfase (1993) by R. D. D. Croy, published by BIOS Scientific Publications Ltd (UK) and Blackwell Scientific Publications (UK).

Example 1

Identification of Sequences Related to SEQ ID NO: 1 and SEQ ID NO: 2

Sequences (full length cDNA, ESTs or genomic) were identified amongst those maintained in the Entrez Nucleotides database at the National Center for Biotechnology Information (NCBI) using database sequence search tools, such as the Basic Local Alignment Tool (BLAST) (Altschul et al. (1990) J. Mol. Biol. 215:403-410; and Altschul et al. (1997) Nucleic Acids Res. 25:3389-3402). The program was used to find regions of local similarity between sequences by comparing nucleic acid or polypeptide sequences to sequence databases and by calculating the statistical significance of matches. For example, the polypeptide encoded by the nucleic acid of SEQ ID NO: 1 was used for the TBLASTN algorithm, with default settings and the filter to ignore low complexity sequences set off. The output of the analysis was viewed by pairwise comparison, and ranked according to the probability score (E-value), where the score reflects the probability that a particular alignment occurs by chance (the lower the E-value, the more significant the hit). In addition to E-values, comparisons were also scored by percentage identity. Percentage identity refers to the number of identical nucleotides (or amino acids) between the two compared nucleic acid (or polypeptide) sequences over a particular length. In some instances, the default parameters may be adjusted to modify the stringency of the search. For example the E-value may be increased to show less stringent matches. This way, short nearly exact matches may be identified.

Table A below provides a list of nucleic acid sequences related to the nucleic acid sequence of SEQ ID NO: 1.

TABLE A

Examples of sequences related to the nucleic acid sequence of SEQ ID NO: 1

| Name | NCBI nucleotide accession number | Nucleotide SEQ ID NO | Translated polypeptide SEQ ID NO | Source |
|---|---|---|---|---|
| Orysa_hox5 | XM_482406 | 1 | 2 | *Oryza sativa* |
| Orysa_hox16 | XM_467603 | 3 | 4 | *Oryza sativa* |
| Zeama_hox5* | CO458693 DV024016 | 5 | 6 | *Zea mays* |
| Zeama_hox16 | AY105265 | 7 | 8 | *Zea mays* |
| Sacof_hox5* | CA088615 CA115362 CA142506 | 9 | 10 | *Saccharum officinarum* |
| Sorbi_hox5* | BE363386 CD432381 | 11 | 12 | *Sorghum bicolor* |
| Triae_hox16* | DR735359 DR741379 CD916488 | 13 | 14 | *Triticum aestivum* |
| Arath_ATHB1 | X58821 | 15 | 16 | *Arabidopsis thaliana* |
| Dauca_CHB3** | D26575 | 17 | 18 | *Daucus carota* |
| Glyma_HD157** | AF184278 | 19 | 20 | *Glycine max* |
| Crapl_CPHB-5 | AF443621 | 21 | 22 | *Craterostigma plantagineum* |
| Goshi_hox5* | DT465649 CD486134 | 23 | 24 | *Gossypium hirsutum* |
| Lyces_hox5 | BT014213.1 | 25 | 26 | *Lycopersicon esculentum* |
| Lyces_VaHOX1 | X94947 | 27 | 28 | *Lycopersicon esculentum* |
| Medsa_hox16* | CB892061 CA858059 | 29 | 30 | *Medicago sativa* |
| Aqufo_hox5 | DT758247 | 31 | 32 | *Aquilegia formosa* x *Aquilegia pubescens* |
| Poptr_hox16_1 | scaff_XV.439 | 40 | 41 | *Populus tremuloides* |
| Poptr_hox16_2 | scaff_XII.649 | 42 | 43 | *Populus tremuloides* |
| Poptr_hox16_3 | lcl\|scaff_VIII.1839 | 44 | 45 | *Populus tremuloides* |
| Medtr_hox16_1 | CR954197.2 | 46 | 47 | *Medicago truncatula* |
| Phavu_hox16 | AF402605 | 48 | 49 | *Phaseolus vulgaris* |
| Lotco_hox16 | AP006364 | 50 | 51 | *Lotus corniculatus* |

*Contig compiled from several EST accessions (main ones shown); EST sequencing quality being usually lower, a few nucleic acid substitutions may be expected.
**Sequences from *Daucus carota* and *Glycine max* have been corrected compared to their accession number.

Example 2

Alignment of class I HDZip hox5 Polypeptide Sequences

AlignX from the Vector NTI (Invitrogen) based on the popular Clustal algorithm of progressive alignment (Thompson et al. (1997) Nucleic Acids Res 25:4876-4882; Chenna et al. (2003). Nucleic Acids Res 31:3497-3500) was used. A phylogenetic tree can be constructed using a neighbour-joining clustering algorithm. Default values are for the gap open penalty of 10, for the gap extension penalty of 0.1 and the selected weight matrix is Blosum 62 (if polypeptides are aligned).

The result of the multiple sequence alignment is shown in FIG. 2. The three main characterized domains, from N-terminal to C-terminal, are heavily boxed and identified as the acidic box, the class I homeodomain and the six heptad-leucine zipper. The "Conserved Domain" comprises these three domains. Additionally, the Trp tail and the RPFF amino acid motif are lightly boxed.

Example 3

Calculation of Global Percentage Identity Between Class I HDZip Hox5 Polypeptides Sequences Global percentages of similarity and identity between full length class I HDZip hox5 polypeptide sequences were determined using the Matrix Global Alignment Tool (MatGAT) software (BMC Bioinformatics. 2003 4:29. MatGAT: an application that generates similarity/identity matrices using protein or DNA sequences. Campanella J J, Bitincka L, Smalley J; software hosted by Ledion Bitincka). MatGAT software generates similarity/identity matrices for DNA or protein sequences without needing pre-alignment of the data. The program performs a series of pair-wise alignments using the Myers and Miller global alignment algorithm (with a gap opening penalty of 12, and a gap extension penalty of 2), calculates similarity and identity using for example Blosum 62 (for polypeptides), and then places the results in a distance matrix. Sequence similarity is shown in the bottom half of the dividing line and sequence identity is shown in the top half of the diagonal dividing line.

Parameters used in the comparison were:

Scoring matrix: Blosum62

First Gap: 12

Extending gap: 2

Results of the software analysis are shown in Table B1 for the global similarity and identity over the full length of the polypeptide sequences (excluding the partial polypeptide sequences). Percentage identity is given above the diagonal and percentage similarity is given below the diagonal.

The percentage identity between the polypeptide sequences shown can be as low as 29% amino acid identity compared to SEQ ID NO: 2.

TABLE B1

MatGAT results for global similarity and identity over the full length of the polypeptide sequences.

|  | 1 | 2 | 3 | 4 | 5 | 6 | 7 | 8 | 9 | 10 | 11 | 12 | 13 | 14 | 15 | 16 | 17 | 18 | 19 | 20 | 21 | 22 |
|---|---|---|---|---|---|---|---|---|---|---|---|---|---|---|---|---|---|---|---|---|---|---|
| 1. Aqufo_Hox5 |  | 56 | 54 | 37 | 34 | 64 | 36 | 64 | 35 | 34 | 36 | 47 | 37 | 36 | 38 | 38 | 36 | 42 | 41 | 46 | 49 | 42 |
| 2. Arath_ATHB1 | 73 |  | 52 | 34 | 34 | 59 | 36 | 57 | 33 | 34 | 36 | 44 | 34 | 35 | 40 | 35 | 35 | 39 | 39 | 41 | 43 | 39 |
| 3. Crapl_CPHB-5 | 69 | 66 |  | 33 | 35 | 56 | 37 | 59 | 33 | 33 | 33 | 45 | 39 | 34 | 37 | 36 | 36 | 41 | 39 | 41 | 44 | 41 |
| 4. Dauca_CHB3 | 52 | 52 | 48 |  | 44 | 39 | 53 | 35 | 46 | 49 | 46 | 30 | 33 | 47 | 58 | 56 | 43 | 32 | 33 | 31 | 33 | 33 |
| 5. Glyma_HD157 | 50 | 47 | 48 | 58 |  | 33 | 44 | 32 | 43 | 43 | 72 | 33 | 31 | 84 | 48 | 48 | 47 | 32 | 31 | 31 | 31 | 32 |
| 6. Goshi_Hox5 | 79 | 74 | 71 | 53 | 49 |  | 38 | 64 | 36 | 36 | 37 | 46 | 38 | 35 | 39 | 36 | 35 | 40 | 39 | 46 | 49 | 40 |
| 7. Lotco_Hox16 | 51 | 53 | 51 | 66 | 62 | 53 |  | 35 | 45 | 66 | 50 | 29 | 31 | 49 | 62 | 59 | 49 | 30 | 31 | 30 | 32 | 31 |
| 8. Lyces_Hox5 | 75 | 70 | 72 | 51 | 45 | 75 | 50 |  | 34 | 34 | 36 | 46 | 38 | 34 | 37 | 36 | 33 | 41 | 41 | 45 | 47 | 41 |
| 9. Lyces_VaHOX1 | 49 | 48 | 47 | 63 | 58 | 48 | 62 | 47 |  | 45 | 44 | 31 | 32 | 47 | 53 | 49 | 44 | 33 | 33 | 32 | 33 | 33 |
| 10. Medtr_Hox16 | 48 | 48 | 50 | 65 | 64 | 49 | 78 | 48 | 63 |  | 46 | 30 | 30 | 45 | 59 | 55 | 42 | 31 | 30 | 31 | 31 | 30 |
| 11. Medtr_Hox16_1 | 52 | 49 | 50 | 61 | 81 | 49 | 67 | 49 | 61 | 64 |  | 33 | 28 | 77 | 51 | 48 | 50 | 32 | 31 | 29 | 29 | 32 |
| 12. Orysa_Hox16 | 62 | 59 | 58 | 50 | 50 | 60 | 47 | 58 | 45 | 50 | 51 |  | 49 | 34 | 32 | 31 | 30 | 46 | 45 | 73 | 76 | 45 |
| 13. Orysa_Hox5 | 53 | 47 | 52 | 48 | 48 | 52 | 48 | 50 | 44 | 45 | 46 | 59 |  | 32 | 32 | 32 | 30 | 66 | 66 | 49 | 50 | 65 |
| 14. Phavu_HOX16 | 51 | 51 | 48 | 64 | 89 | 49 | 65 | 47 | 63 | 65 | 88 | 49 | 48 |  | 56 | 55 | 51 | 34 | 32 | 31 | 32 | 33 |
| 15. Poptr_HOX16_1 | 54 | 54 | 52 | 71 | 66 | 52 | 75 | 50 | 66 | 73 | 69 | 48 | 49 | 71 |  | 92 | 48 | 35 | 35 | 32 | 34 | 34 |
| 16. Poptr_HOX16_2 | 51 | 49 | 51 | 70 | 66 | 50 | 73 | 49 | 65 | 70 | 66 | 47 | 46 | 71 | 96 |  | 47 | 34 | 33 | 32 | 32 | 34 |
| 17. Poptr_HOX16_3 | 52 | 51 | 47 | 59 | 59 | 52 | 63 | 45 | 59 | 59 | 62 | 44 | 44 | 65 | 63 | 63 |  | 34 | 33 | 30 | 31 | 33 |
| 18. Sacof_Hox5 | 62 | 58 | 57 | 47 | 44 | 60 | 48 | 57 | 44 | 45 | 46 | 56 | 69 | 46 | 48 | 47 | 47 |  | 95 | 46 | 46 | 94 |
| 19. Sorbi_Hox5 | 62 | 57 | 55 | 46 | 45 | 58 | 51 | 58 | 45 | 44 | 46 | 56 | 69 | 47 | 50 | 47 | 46 | 97 |  | 43 | 46 | 94 |
| 20. Triae_Hox16 | 62 | 54 | 56 | 48 | 48 | 59 | 47 | 58 | 47 | 49 | 47 | 82 | 61 | 48 | 52 | 51 | 46 | 56 | 55 |  | 72 | 45 |
| 21. Zeama_Hox16 | 63 | 58 | 59 | 51 | 49 | 62 | 51 | 60 | 49 | 50 | 47 | 81 | 62 | 51 | 49 | 48 | 46 | 56 | 57 | 81 |  | 45 |
| 22. Zeama_Hox5 | 62 | 58 | 56 | 46 | 44 | 59 | 49 | 57 | 45 | 45 | 45 | 55 | 68 | 46 | 50 | 46 | 48 | 96 | 96 | 57 | 56 |  |

The "Conserved Domain" of class I HDZip hox5 polypeptide sequences comprises from N-terminal to C-terminal, an acidic box, a class I homeodomain and the six heptad-leucine zipper (see FIG. 2), as defined hereinabove. When percentage identity analysis is performed on the conserved domains instead of on the full length polypeptide sequences, an increase in percentage identity is observed, as shown in Table B 2. Lowest values are now above 50% amino acid identity compared to SEQ ID NO: 2.

TABLE B2

MatGAT results for global similarity and identity over the "Conserved Domain" of the polypeptide sequences.

|  | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| 1. Aqufo_hox5_CD |  | 81 | 74 | 66 | 82 | 62 | 82 | 62 | 61 | 75 | 66 | 61 | 67 | 63 | 60 | 68 | 67 | 73 | 76 | 67 |
| 2. Arath_ATHB1_CD | 93 |  | 74 | 59 | 82 | 61 | 85 | 61 | 61 | 71 | 66 | 63 | 65 | 62 | 59 | 67 | 66 | 71 | 71 | 67 |
| 3. Crapl_CPHB-5_CD | 85 | 85 |  | 61 | 78 | 62 | 77 | 57 | 60 | 69 | 63 | 62 | 62 | 58 | 65 | 65 | 64 | 66 | 68 | 65 |
| 4. Dauca_CHB3_CD | 81 | 79 | 75 |  | 64 | 70 | 62 | 66 | 69 | 57 | 57 | 64 | 80 | 75 | 66 | 58 | 59 | 57 | 57 | 58 |
| 5. Goshi_hox5_CD | 94 | 95 | 89 | 81 |  | 66 | 83 | 63 | 63 | 74 | 66 | 63 | 68 | 63 | 64 | 67 | 66 | 73 | 75 | 67 |
| 6. Lotco_hox16_CD | 80 | 78 | 74 | 81 | 80 |  | 62 | 67 | 85 | 54 | 52 | 62 | 77 | 73 | 64 | 53 | 52 | 54 | 54 | 53 |
| 7. Lyces_hox5_CD | 91 | 92 | 88 | 79 | 92 | 77 |  | 57 | 61 | 75 | 68 | 63 | 66 | 62 | 60 | 71 | 69 | 75 | 76 | 70 |
| 8. Lyces_VaHOX1_CD | 77 | 75 | 71 | 79 | 76 | 84 | 74 |  | 71 | 56 | 57 | 62 | 73 | 68 | 60 | 58 | 58 | 57 | 57 | 58 |
| 9. Medtr_hox16_CD | 77 | 75 | 74 | 81 | 77 | 93 | 75 | 84 |  | 59 | 57 | 61 | 75 | 71 | 62 | 57 | 57 | 58 | 59 | 57 |
| 10. Orysa_hox16_CD | 93 | 92 | 85 | 77 | 92 | 79 | 92 | 74 | 75 |  | 84 | 58 | 60 | 58 | 58 | 82 | 82 | 94 | 96 | 82 |
| 11. Orysa_hox5_CD | 90 | 87 | 83 | 78 | 88 | 77 | 88 | 71 | 74 | 91 |  | 59 | 58 | 57 | 57 | 92 | 93 | 81 | 84 | 94 |
| 12. Phavu_hox16_CD | 79 | 79 | 75 | 80 | 79 | 81 | 76 | 75 | 80 | 76 | 75 |  | 71 | 71 | 65 | 60 | 60 | 57 | 58 | 60 |
| 13. Poptr_hox16_1_CD | 81 | 80 | 75 | 88 | 82 | 90 | 79 | 84 | 87 | 79 | 80 | 86 |  | 93 | 65 | 59 | 60 | 58 | 61 | 59 |
| 14. Poptr_hox16_2_CD | 79 | 77 | 74 | 85 | 79 | 87 | 76 | 82 | 84 | 75 | 75 | 85 | 98 |  | 62 | 57 | 57 | 56 | 58 | 57 |
| 15. Poptr_hox16_3_CD | 74 | 75 | 73 | 80 | 75 | 76 | 71 | 76 | 77 | 73 | 71 | 78 | 77 | 77 |  | 57 | 57 | 56 | 58 | 58 |
| 16. Sacof_hox5_CD | 89 | 86 | 80 | 77 | 87 | 77 | 86 | 71 | 73 | 88 | 96 | 74 | 79 | 75 | 72 |  | 98 | 79 | 82 | 98 |
| 17. Sorbi_hox5_CD | 89 | 86 | 81 | 77 | 87 | 77 | 87 | 71 | 73 | 89 | 97 | 74 | 79 | 76 | 72 | 99 |  | 78 | 82 | 98 |
| 18. Triae_hox16_CD | 93 | 92 | 85 | 79 | 92 | 80 | 92 | 74 | 75 | 98 | 91 | 77 | 80 | 77 | 73 | 88 | 89 |  | 95 | 79 |
| 19. Zeama_hox16_CD | 93 | 92 | 86 | 78 | 92 | 81 | 92 | 75 | 77 | 98 | 92 | 79 | 80 | 76 | 74 | 90 | 91 | 98 |  | 82 |
| 20. Zeama_hox5_CD | 89 | 86 | 81 | 77 | 87 | 77 | 87 | 71 | 73 | 89 | 97 | 74 | 79 | 75 | 72 | 99 | 100 | 89 | 91 |  |

Example 4

Identification of Domains Comprised in Class I HDZip hox5 Polypeptide Sequences The Integrated Resource of Protein Families, Domains and Sites (InterPro) database is an integrated interface for the commonly used signature databases for text- and sequence-based searches. The InterPro database combines these databases, which use different methodologies and varying degrees of biological information about well-characterized proteins to derive protein signatures. Collaborating databases include SWISS-PROT, PROSITE, TrEMBL, PRINTS, ProDom and Pfam, Smart and TIGRFAMs. Interpro is hosted at the European Bioinformatics Institute in the United Kingdom.

The results of the InterPro scan of the polypeptide sequence as represented by SEQ ID NO: 2 are presented in Table C.

TABLE C

InterPro scan results of the polypeptide sequence as represented by SEQ ID NO: 2

| | | | |
|---|---|---|---|
| InterPro | IPR000047 | Helix-turn-helix motif, lambda-like repressor | |
| | PRINTS | PR00031 | HTHREPRESSR |
| InterPro | IPR001356 | Homeobox | |
| | PRODOM | PD000010 | Homeobox |
| | PRINTS | PR00024 | HOMEOBOX |
| | PFAM | PF00046 | Homeobox |
| | SMART | SM00389 | HOX |
| | PROFILE | PS00027 | HOMEOBOX_1 |
| | PROFILE | PS50071 | HOMEOBOX_2 |
| InterPro | IPR003106 | Leucine zipper, homeobox-associated | |
| | PFAM | PF02183 | HALZ |
| InterPro | IPR009057 | Homeodomain-like | |
| | SUPERFAMILY | SSF46689 | Homeodomain_like |
| InterPro | IPR012287 | Homeodomain-related | |
| | GENE3D | G3DSA: 1.10.10.60 | Homeodomain-rel |

Primary amino acid composition (in %) to determine if a polypeptide domain is rich in specific amino acids (for example in an acidic box) may be calculated using software programs from the ExPASy server, in particular the ProtParam tool (Gasteiger E et al. (2003) ExPASy: the proteomics server for in-depth protein knowledge and analysis. Nucleic Acids Res 31:3784-3788). The composition of the polypeptide sequence of interest may then be compared to the average amino acid composition (in %) in the Swiss-Prot Protein Sequence data bank.

In the Table below (Table D), are compared the % Asp (D), % Glu (E) and their combined content in the acidic box of SEQ ID NO: 2 with the average in Swiss-Prot Protein Sequence databank.

TABLE D

| | % Asp (D) | % Glu (E) | % Asp (D) + % Glu (E) |
|---|---|---|---|
| Average in Swiss-Prot Protein Sequence databank | 5.3% | 6.6% | 11.9% |
| Acidic box of SEQ ID NO: 2 | 9.1% | 54.5% | 63.6% |

An acidic box may be part of a transcription activation domain. Eukaryotic transcription activation domains have been classified according to their amino acid content, and major categories include acidic, glutamine-rich and proline-rich activation domains (Rutherford et al. (2005) Plant J. 43(5): 769-88, and references therein).

The Gene Ontology (GO) Consortium is an international collaboration among scientists at various biological databases, with an Editorial Office based at the European Bioinformatics Institute. The objective of GO is to provide controlled vocabularies for the description of the molecular function, biological process and cellular component of gene products. When performing an InterPro scan as described above, the GO database is also searched. The class I HDZip hox5 polypeptide sequences have as molecular function transcription factor and sequence-specific DNA binding activity, and localised in the nucleus of the plant cell (see Table below (Table E)).

TABLE E

| | Gene Ontology Entry |
|---|---|
| Homeodomain | Molecular Function: transcription factor activity (GO: 0003700)<br>Cellular Component: nucleus (GO: 0005634)<br>Molecular Function: sequence-specific DNA binding (GO: 0043565) |
| Leucine zipper, homeobox-associated | Molecular Function: DNA binding (GO: 0003677)<br>Cellular Component: nucleus (GO: 0005634) |

Example 5

Topology Prediction of Class I HDZip hox5 Polypeptide Sequences

Leucine zipper prediction and heptad identification was carried out using specialised software such as 2ZIP, which combines a standard coiled coil prediction algorithm with an approximate search for the characteristic leucine repeat (Bornberg-Bauer et al. (1998) Nucleic Acids Res 26(11): 2740-2746; hosted at Max Planck Institut, Golm in Germany). A potential leucine zipper, a repeat of leucines or a coiled coil may be identified using this software.

The class I HDZip hox5 polypeptide sequences comprise a leucine zipper prediction, with at least 5, preferably 6 heptads. When the polypeptide of SEQ ID NO: 2 is submitted to this algorithm, a potential leucine zipper is between positions 143 and 178, as shown in the output below (numbers reflect amino acid position, C the coiled coil region, and L the leucine within the heptad):

TABLE 4

```
1---------11--------21--------31--------41--------51--------
MDPGRVVFDSGVARRACPGGAQMLLFGGGGSANSGGFFRGVPAAVLGMDESRSSSSAAGA

61--------71--------81--------91--------101-------111-------
GAKRPFFTTHEELLEEEYYDEQAPEKKRRLTAEQVQMLERSFEEENKLEPERKTELARRL

121-------131-------141-------151-------161-------171-------
GMAPRQVAVWFQNRRARWKTKQLEHDFDRLKAAYDALAADHHALLSDNDRLRAQVISLTE
           CCCCCCCCCCCCCCCCCCCCCCCCCCCCCCCCCCCCCCCCCCCCCCC
                  L------L------L------L------L------L
                  LZLZLZLZLZLZLZLZLZLZLZLZLZLZLZLZLZLZLZ

181-------191-------201-------211-------221-------231-------
KLQDKETSPSSATITTAAQEVDQPDEHTEAASTTGFATVDGALAAPPPGHQQPPHKDDLV
CCCCCCCC

241-------251-------261-------271-------281-------291-------
SSGGTNDDGDGGAAVVVFDVTEGANDRLSCESAYFADAAEAYERDCAGHYALSSEEEDGG

301-------311-------321-------331-------341------
AVSDEGCSFDLPDAAAAAAMFGAAGVVHHDAADDEEAQLGSWTAWFWS
```

Example 6

Assay for Class I HDZip hox5 Polypeptide Sequences

Class I HDZip hox5 polypeptides or homologues thereof have DNA binding activity, preferably to 5 bp half-sites that overlap at a central position, CAA(A/T)ATTG, as detected in yeast one-hybrid assays (Meijer et al. (2000) Mol Gen Genet 263:12-21). In transient assays on rice cell suspensions, co-bombardement of a class I HDZip hox5 polypeptide with the GUS reporter gene reportedly resulted in an increased number of stained spots, which were also more intense in color (Meijer et al, supra). This assay is useful to demonstrate the activator function of class I HDZip hox5 polypeptides or homologues.

Example 7

Cloning of Oryza sativa Class I HDZip hox5 Nucleic Acid Sequence

The Oryza sativa class I HDZip hox5 nucleic acid sequence was amplified by PCR using as template an Oryza sativa seedling cDNA library (Invitrogen, Paisley, UK). After reverse transcription of RNA extracted from seedlings, the cDNAs were cloned into pCMV Sport 6.0. Average insert size of the bank was 1.6 kb and the original number of clones was of the order of $1.67 \times 10^7$ cfu. Original titer was determined to be $3.34 \times 10^6$ cfu/ml after first amplification of $6 \times 10^{10}$ cfu/ml. After plasmid extraction, 200 ng of template was used in a 50 µl PCR mix. Primers prm06000 (SEQ ID NO: 34; sense, start codon in bold, AttB1 site in italic: 5'-GGGGACAAGTTTG-TACAAAAAAGCAGGCTTAAACAATG-GATCCCGGCCG-3') and prm06001 (SEQ ID NO: 35; reverse, complementary, AttB2 site in italic: 5'-GGGGAC-CACTTTGTACAAG AAAGCTGGGTGATCAGCTCCA-GAACCAGG-3'), which include the AttB sites for Gateway recombination, were used for PCR amplification. PCR was performed using Hifi Taq DNA polymerase in standard conditions. A PCR fragment of 1116 bp (including attB sites; from start to stop 1050 bp) was amplified and purified also using standard methods. The first step of the Gateway procedure, the BP reaction, was then performed, during which the PCR fragment recombines in vivo with the pDONR201 plasmid to produce, according to the Gateway terminology, an "entry clone". Plasmid pDONR201 was purchased from Invitrogen, as part of the Gateway® technology.

Example 8

Vector Construction

The entry clone comprising the nucleic acid sequences was subsequently used in an LR reaction with a "destination" vector used for Oryza sativa transformation. This vector contained as functional elements within the T-DNA borders: a plant selectable marker; a screenable marker expression cassette; and a Gateway cassette intended for LR in vivo recombination with the sequence of interest already cloned in the entry clone. A rice GOS2 promoter (SEQ ID NO: 33 or SEQ ID NO: 52) for constitutive expression was located upstream of this Gateway cassette.

After the LR recombination step, the resulting expression vector (FIG. 3) was transformed into Agrobacterium strain LBA4044 according to methods well known in the art.

Example 9

Plant Transformation

Rice Transformation

The Agrobacterium containing the expression vector was used to transform Oryza sativa plants. Mature dry seeds of the rice japonica cultivar Nipponbare were dehusked. Sterilization was carried out by incubating for one minute in 70% ethanol, followed by 30 minutes in 0.2% HgCl2, followed by a 6 times 15 minutes wash with sterile distilled water. The sterile seeds were then germinated on a medium containing 2,4-D (callus induction medium). After incubation in the dark for four weeks, embryogenic, scutellum-derived calli were excised and propagated on the same medium. After two weeks, the calli were multiplied or propagated by subculture on the same medium for another 2 weeks. Embryogenic callus pieces were sub-cultured on fresh medium 3 days before co-cultivation (to boost cell division activity).

Agrobacterium strain LBA4404 containing the expression vector was used for cocultivation. Agrobacterium was inoculated on AB medium with the appropriate antibiotics and cultured for 3 days at 28° C. The bacteria were then collected and suspended in liquid co-cultivation medium to a density (OD600) of about 1. The suspension was then transferred to a Petri dish and the calli immersed in the suspension for 15 minutes. The callus tissues were then blotted dry on a filter paper and transferred to solidified, co-cultivation medium and incubated for 3 days in the dark at 25° C. Co-cultivated calli were grown on 2,4-D-containing medium for 4 weeks in the dark at 28° C. in the presence of a selection agent. During this period, rapidly growing resistant callus islands developed. After transfer of this material to a regeneration medium and incubation in the light, the embryogenic potential was released and shoots developed in the next four to five weeks. Shoots were excised from the calli and incubated for 2 to 3 weeks on an auxin-containing medium from which they were transferred to soil. Hardened shoots were grown under high humidity and short days in a greenhouse.

Approximately 35 independent T0 rice transformants were generated for one construct. The primary transformants were transferred from a tissue culture chamber to a greenhouse. After a quantitative PCR analysis to verify copy number of the T-DNA insert, only single copy transgenic plants that exhibit tolerance to the selection agent were kept for harvest of T1 seed. Seeds were then harvested three to five months after transplanting. The method yielded single locus transformants at a rate of over 50% (Aldemita and Hodges 1996, Chan et al. 1993, Hiei et al. 1994).

Example 10

Phenotypic Evaluation Procedure 10.1 Evaluation Setup

Approximately 35 independent T0 rice transformants were generated. The primary transformants were transferred from a tissue culture chamber to a greenhouse for growing and harvest of T1 seed. Seven events, of which the T1 progeny segregated 3:1 for presence/absence of the transgene, were retained. For each of these events, approximately 10 T1 seedlings containing the transgene (hetero- and homo-zygotes) and approximately 10 T1 seedlings lacking the transgene (nullizygotes) were selected by monitoring visual marker expression. The transgenic plants and the corresponding nullizygotes were grown side-by-side at random positions. Greenhouse conditions were of shorts days (12 hours light), 28° C. in the light and 22° C. in the dark, and a relative humidity of 70%.

All T1 events were further evaluated in the T2 generation following the same evaluation procedure as for the T1 generation. From the stage of sowing until the stage of maturity the plants were passed several times through a digital imaging cabinet. At each time point, digital images (2048×1536 pixels, 16 million colours) were taken of each plant from at least 6 different angles.

Reduced Nutrient (Nitrogen) Availability Screen

Plants from six events (T2 seeds) were grown in potting soil under normal conditions except for the nutrient solution. The pots were watered from transplantation to maturation with a specific nutrient solution containing reduced N nitrogen (N) content, usually between 7 to 8 times less. The rest of the cultivation (plant maturation, seed harvest) was the same as for plants not grown under abiotic stress. Seed-related parameters were then measured 10.2 Statistical Analysis: F Test A two factor ANOVA (analysis of variants) was used as a statistical model for the overall evaluation of plant phenotypic characteristics. An F test was carried out on all the parameters measured of all the plants of all the events transformed with the gene of the present invention. The F test was carried out to check for an effect of the gene over all the transformation events and to verify for an overall effect of the gene, also known as a global gene effect. The threshold for significance for a true global gene effect was set at a 5% probability level for the F test. A significant F test value points to a gene effect, meaning that it is not only the mere presence or position of the gene that is causing the differences in phenotype.

10.3 Parameters Measured 10.3.1 Biomass-Related Parameter Measurement

From the stage of sowing until the stage of maturity the plants were passed several times through a digital imaging cabinet. At each time point digital images (2048×1536 pixels, 16 million colours) were taken of each plant from at least 6 different angles.

The plant aboveground area (or leafy biomass) was determined by counting the total number of pixels on the digital images from aboveground plant parts discriminated from the background. This value was averaged for the pictures taken on the same time point from the different angles and was converted to a physical surface value expressed in square mm by calibration. Experiments show that the aboveground plant area measured this way correlates with the biomass of plant parts above ground. The aboveground area is the time point at which the plant had reached its maximal leafy biomass. The early vigour is the plant (seedling) aboveground area three weeks post-germination.

An additional parameter was calculated from the digital images of plants: the greenness index. For each pixel belonging to the plant object on the image, the ratio of the green value versus the red value (in the RGB model for encoding color) is calculated. The greenness index is expressed as the percentage of pixels for which the green-to-red ratio exceeds a given threshold. Under reduced nutrient availability growth conditions, the greenness index of plants was measured in the last imaging before flowering.

To measure root-related parameters, plants were grown in specially designed pots with transparent bottoms to allow visualization of the roots. A digital camera recorded images through the bottom of the pot during plant growth. Root features such as total projected area (which can be correlated to total root volume), average diameter and length of roots above a certain thickness threshold (length of thick roots, or thick root length) were deduced from the picture using of appropriate software. Increase in root biomass is expressed as an increase in total root biomass (measured as maximum biomass of roots observed during the lifespan of a plant); or as an increase in the root/shoot index (measured as the ratio between root mass and shoot mass in the period of active growth of root and shoot).

10.3.2 Seed-Related Parameter Measurements

The mature primary panicles were harvested, counted, bagged, barcode-labelled and then dried for three days in an oven at 37° C. The panicles were then threshed and all the seeds were collected and counted. The filled husks were separated from the empty ones using an air-blowing device. The empty husks were discarded and the remaining fraction was counted again. The filled husks were weighed on an analytical balance. The number of filled seeds was determined by counting the number of filled husks that remained after the separation step. The total seed yield was measured by weighing all filled husks harvested from a plant. Total seed number per plant was measured by counting the number of husks harvested from a plant. Thousand Kernel Weight (TKW) is extrapolated from the number of filled seeds counted and their total weight. The Harvest Index (HI) in the present invention is defined as the ratio between the total seed yield and the above ground area ($mm^2$), multiplied by a factor 106. The total number of flowers per panicle as defined in the present invention is the ratio between the total number of seeds and the number of mature primary panicles. The seed fill rate as defined in the present invention is the proportion (expressed as a %) of the number of filled seeds over the total number of seeds (or florets).

Example 11

Results of Transgenic Rice Plants Expressing the Class I HDZip hox5 Nucleic Acid Sequence, Grown Under Reduced Nutrient Availability Conditions The results of the evaluation of transgenic rice plants expressing the nucleic acid sequence useful in performing the methods of the invention under grown reduced nutrient availability stress conditions are presented in Table F. The percentage difference between the transgenics and the corresponding nullizygotes is shown.

TABLE F

Results of the evaluation of transgenic rice plants expressing the nucleic acid sequence useful in performing the methods of the invention, grown under reduced nutrient availability conditions.

| Trait | % Difference in T1 |
| --- | --- |
| Total seed yield per plant | 20 |
| Number of filled seeds | 19 |
| Seed fill rate | 4 |
| Number of flowers per panicle | 9 |
| Harvest index | 12 |
| Greenness index before flowering | 11 |

Example 12

Transformation of Corn, Wheat, Soybean, Canola, Alfalfa, Cotton, with Sequences Useful in the Methods of the Invention Corn Transformation Transformation of maize (*Zea mays*) is performed with a modification of the method described by Ishida et al. (1996) Nature Biotech 14(6): 745-50. Transformation is genotype-dependent in corn and only specific genotypes are amenable to transformation and regeneration. The inbred line A188 (University of Minnesota) or hybrids with A188 as a parent are good sources of donor material for transformation, but other genotypes can be used successfully as well. Ears are harvested from corn plant approximately 11 days after pollination (DAP) when the length of the immature embryo is about 1 to 1.2 mm. Immature embryos are cocultivated with *Agrobacterium tumefaciens* containing the expression vector, and transgenic plants are recovered through organogenesis. Excised embryos are grown on callus induction medium, then maize regeneration medium, containing the selection agent (for example imidazolinone but various selection markers can be used). The Petri plates are incubated in the light at 25° C. for 2-3 weeks, or until shoots develop. The green shoots are transferred from each embryo to maize rooting medium and incubated at 25° C. for 2-3 weeks, until roots develop. The rooted shoots are transplanted to soil in the greenhouse. T1 seeds are produced from plants that exhibit tolerance to the selection agent and that contain a single copy of the T-DNA insert.

Wheat Transformation

Transformation of wheat is performed with the method described by Ishida et al. (1996) Nature Biotech 14(6): 745-50. The cultivar Bobwhite (available from CIMMYT, Mexico) is commonly used in transformation. Immature embryos are co-cultivated with *Agrobacterium tumefaciens* containing the expression vector, and transgenic plants are recovered through organogenesis. After incubation with *Agrobacterium*, the embryos are grown in vitro on callus induction medium, then regeneration medium, containing the selection agent (for example imidazolinone but various selection markers can be used). The Petri plates are incubated in the light at 25° C. for 2-3 weeks, or until shoots develop. The green shoots are transferred from each embryo to rooting medium and incubated at 25° C. for 2-3 weeks, until roots develop. The rooted shoots are transplanted to soil in the greenhouse. T1 seeds are produced from plants that exhibit tolerance to the selection agent and that contain a single copy of the T-DNA insert.

Soybean Transformation

Soybean is transformed according to a modification of the method described in the Texas A&M U.S. Pat. No. 5,164,310. Several commercial soybean varieties are amenable to transformation by this method. The cultivar Jack (available from the Illinois Seed foundation) is commonly used for transformation. Soybean seeds are sterilised for in vitro sowing. The hypocotyl, the radicle and one cotyledon are excised from seven-day old young seedlings. The epicotyl and the remaining cotyledon are further grown to develop axillary nodes. These axillary nodes are excised and incubated with *Agrobacterium tumefaciens* containing the expression vector. After the cocultivation treatment, the explants are washed and transferred to selection media. Regenerated shoots are excised and placed on a shoot elongation medium. Shoots no longer than 1 cm are placed on rooting medium until roots develop. The rooted shoots are transplanted to soil in the greenhouse. T1 seeds are produced from plants that exhibit tolerance to the selection agent and that contain a single copy of the T-DNA insert.

Rapeseed/Canola Transformation

Cotyledonary petioles and hypocotyls of 5-6 day old young seedling are used as explants for tissue culture and transformed according to Babic et al. (1998, Plant Cell Rep 17: 183-188). The commercial cultivar Westar (Agriculture Canada) is the standard variety used for transformation, but other varieties can also be used. Canola seeds are surface-sterilized for in vitro sowing. The cotyledon petiole explants with the cotyledon attached are excised from the in vitro seedlings, and inoculated with *Agrobacterium* (containing the expression vector) by dipping the cut end of the petiole explant into the bacterial suspension. The explants are then cultured for 2 days on MSBAP-3 medium containing 3 mg/l BAP, 3% sucrose, 0.7% Phytagar at 23° C., 16 hr light. After two days of co-cultivation with *Agrobacterium*, the petiole explants are transferred to MSBAP-3 medium containing 3 mg/l BAP, cefotaxime, carbenicillin, or timentin (300 mg/l) for 7 days, and then cultured on MSBAP-3 medium with cefotaxime, carbenicillin, or timentin and selection agent until shoot regeneration. When the shoots are 5-10 mm in length, they are cut and transferred to shoot elongation medium (MSBAP-0.5, containing 0.5 mg/l BAP). Shoots of about 2 cm in length are transferred to the rooting medium (MS0) for root induction. The rooted shoots are transplanted to soil in the greenhouse. T1 seeds are produced from plants that exhibit tolerance to the selection agent and that contain a single copy of the T-DNA insert.

Alfalfa Transformation

A regenerating clone of alfalfa (Medicago sativa) is transformed using the method of (McKersie et al., 1999 Plant Physiol 119: 839-847). Regeneration and transformation of alfalfa is genotype dependent and therefore a regenerating plant is required. Methods to obtain regenerating plants have been described. For example, these can be selected from the cultivar Rangelander (Agriculture Canada) or any other commercial alfalfa variety as described by Brown DCW and A Atanassov (1985. Plant Cell Tissue Organ Culture 4: 111-112). Alternatively, the RA3 variety (University of Wisconsin) has been selected for use in tissue culture (Walker et al., 1978 Am J Bot 65:654-659). Petiole explants are cocultivated with an overnight culture of *Agrobacterium tumefaciens* C58C1 pMP90 (McKersie et al., 1999 Plant Physiol 119: 839-847) or LBA4404 containing the expression vector. The explants are cocultivated for 3 d in the dark on SH induction medium containing 288 mg/L Pro, 53 mg/L thioproline, 4.35 g/L K2SO4, and 100 µm acetosyringinone. The explants are washed in half-strength Murashige-Skoog medium (Murashige and Skoog, 1962) and plated on the same SH induction medium without acetosyringinone but with a suitable selection agent and suitable antibiotic to inhibit *Agrobacterium* growth. After several weeks, somatic embryos are transferred to BOi2Y development medium containing no growth regulators, no antibiotics, and 50 g/L sucrose. Somatic embryos are subsequently germinated on half-strength Murashige-Skoog medium. Rooted seedlings were transplanted into pots and grown in a greenhouse. T1 seeds are produced from plants that exhibit tolerance to the selection agent and that contain a single copy of the T-DNA insert.

Cotton Transformation

Cotton (*Gossypium hirsutum L.*) transformation is performed using *Agrobacterium tumefaciens*, on hypocotyls explants. The commercial cultivars such as Coker 130 or Coker 312 (SeedCo, Lubbock, Tex.) are standard varieties used for transformation, but other varieties can also be used. The seeds are surface sterilized and germinated in the dark. Hypocotyl explants are cut from the germinated seedlings to lengths of about 1-1.5 centimeter. The hypotocyl explant is submersed in the *Agrobacterium tumefaciens* inoculum containing the expression vector, for 5 minutes then co-cultivated for about 48 hours on MS+1.8 mg/l KNO3+2% glucose at 24° C., in the dark. The explants are transferred the same medium containing appropriate bacterial and plant selectable markers (renewed several times), until embryogenic calli is seen. The calli are separated and subcultured until somatic embryos appear. Plantlets derived from the somatic embryos are matured on rooting medium until roots develop. The rooted shoots are transplanted to potting soil in the greenhouse. T1 seeds are produced from plants that exhibit tolerance to the selection agent and that contain a single copy of the T-DNA insert.

The invention claimed is:

1. A method for increasing yield in plants grown under reduced nitrogen availability relative to corresponding wild type plants, comprising increasing expression in a plant of a nucleic acid sequence encoding a class I homeodomain leucine zipper (HDZip) hox5 polypeptide or homologue thereof, and selecting for plants having increased yield, wherein said class I HDZip hox5 polypeptide or homologue thereof comprises from N-terminal to C-terminal: (i) an acidic box; (ii) a class I homeodomain; and (iii) a leucine zipper with more than 5 heptads, and said class I HDZip hox5 polypeptide or homologue thereof comprises an amino acid sequence having at least 95% sequence identity to the amino acid sequence of SEQ ID NO: 2, and
wherein said increased yield is one or more of: increased total seed yield per plant, increased number of filled seeds, increased seed fill rate, increased number of flowers per panicle, or increased harvest index.

2. The method of claim 1, wherein said class I HDZip hox5 polypeptide or homologue thereof further comprises one or both of the following: (i) a Trp tail; and (ii) a RPFF amino acid motif, where R is Arg, P is Pro and F is Phe, and within this motif, allowing one or more conservative change(s) at any position, and/or one or two non-conservative change(s) at any position.

3. The method of claim 1, wherein said nucleic acid sequence comprises a portion of SEQ ID NO: 1, which portion encodes a polypeptide comprising from N-terminal to C-terminal: (i) an acidic box; (ii) a class I homeodomain; and (iii) a leucine zipper with more than 5 heptads.

4. The method of claim 1, wherein said nucleic acid sequence comprises a sequence capable of hybridising to a class I HDZip hox5 nucleic acid sequence, which hybridising sequence encodes a polypeptide comprising from N-terminal to C-terminal: (i) an acidic box; (ii) a class I homeodomain; and (iii) a leucine zipper with more than 5 heptads.

5. The method of claim 1, wherein said class I HDZip hox5 nucleic acid sequence is of plant origin.

6. The method of claim 1, wherein the nucleic acid sequence encodes the class I HDZip hox5 polypeptide of SEQ ID NO: 2.

7. The method of claim 1, wherein the expression is increased by introducing and expressing in a plant a nucleic acid sequence encoding a class I HDZip hox5 polypeptide ol' a homologue thereof.

8. The method of claim 7, wherein the nucleic acid sequence is operably linked to a constitutive promoter.

9. The method of claim 8, wherein the constitutive promoter is a GOS2 promoter.

10. A method for increasing greenness index in plants grown under reduced nitrogen availability relative to corresponding wild type plants, which method comprises introducing and expressing in a plant a nucleic acid sequence encoding a class I HDZip hox5 polypeptide or a homologue thereof, wherein said class I HDZip hox5 polypeptide or homologue thereof comprises an amino acid sequence having at least 95% sequence identity to the amino acid sequence of SEQ ID NO: 2.

11. The method of claim 1, wherein the expression is modulated by introducing in a plant a construct comprising:
(i) the nucleic acid sequence encoding a class I HDZip hox5 polypeptide or homologue thereof,
(ii) one or more control sequences capable of driving expression of the nucleic acid sequence of (i), and optionally
(iii) a transcription termination sequence.

12. A method for the production of a transgenic plant having increased yield under reduced nitrogen availability relative to a corresponding wild type plant, which method comprises:
(i) introducing and expressing in a plant, plant part or plant cell a nucleic acid sequence encoding a class I HDZip hox5 polypeptide or homologue thereof, wherein said class I HDZip hox5 polypeptide or homologue thereof comprises an amino acid sequence having at least 95% sequence identity to the amino acid sequence of SEQ ID NO: 2;
(ii) cultivating the plant or plant cell under conditions promoting plant growth and development; and
(iii) selecting a plant having increased yield under reduced nitrogen availability relative to a corresponding wild type plant on the basis of said plant showing increased yield under reduced nitrogen availability relative to said wild type plant,
wherein said increased yield is one or more of: increased total seed yield per plant, increased number of filled seeds, increased seed fill rate, increased number of flowers per panicle, or increased harvest index.

13. The method of claim 1, wherein said class I HDZip hox5 nucleic acid sequence is from a monocotyledon plant.

14. The method of claim 13, wherein the monocotyledon plant is *Oryza sativa*.

15. The method of claim 8, wherein the constitutive promoter comprises the sequence of SEQ ID NO: 33 or SEQ ID NO: 52.

16. The method of claim 9, wherein the GOS2 promoter is a rice GOS2 promoter.

17. The method of claim 1, wherein the class I HDZip hox5 polypeptide or homologue thereof comprises an amino acid sequence having at least 95% sequence identity to the amino acid sequence of SEQ ID NO: 2.

18. The method of claim 1, wherein the class I HDZip hox5 polypeptide or homologue thereof comprises an amino acid sequence having at least 90% sequence identity to the amino acid sequence of SEQ ID NO: 2.

19. The method of claim 10, further comprising selecting a plant having increased greenness index under reduced nitrogen availability relative to a corresponding wild type plant on the basis of said plant showing increased greenness index under reduced nitrogen availability relative to said wild type plant.

\* \* \* \* \*

UNITED STATES PATENT AND TRADEMARK OFFICE
CERTIFICATE OF CORRECTION

PATENT NO. : 8,686,221 B2  
APPLICATION NO. : 12/598071  
DATED : April 1, 2014  
INVENTOR(S) : Ana Isabel Sanz Molinero Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 996 days.

Signed and Sealed this

Twenty-ninth Day of September, 2015

Michelle K. Lee
*Director of the United States Patent and Trademark Office*